United States Patent
Yu et al.

(10) Patent No.: US 11,884,683 B2
(45) Date of Patent: Jan. 30, 2024

(54) TRICYCLIC HETEROCYCLE COMPOUNDS USEFUL AS HIV INTEGRASE INHIBITORS

(71) Applicants: Merck Sharp & Dohme LLC, Rahway, NJ (US); Tao Yu, Edison, NJ (US); Alan Whitehead, Scotch Plains, NJ (US); Yili Chen, Hillsborough, NJ (US); Chunrui Sun, Westfield, NJ (US); Zhiyong Hu, Livingston, NJ (US); Kake Zhao, Westfield, NJ (US); Ronald M. Kim, Summit, NJ (US); John A. McCauley, Maple Glen, PA (US)

(72) Inventors: Tao Yu, Edison, NJ (US); Alan Whitehead, Scotch Plains, NJ (US); Yili Chen, Hillsborough, NJ (US); Chunrui Sun, Westfield, NJ (US); Zhiyong Hu, Livingston, NJ (US); Kake Zhao, Westfield, NJ (US); Ronald M. Kim, Summit, NJ (US); John A. McCauley, Maple Glen, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 648 days.

(21) Appl. No.: 17/057,875

(22) PCT Filed: May 31, 2019

(86) PCT No.: PCT/US2019/034783
§ 371 (c)(1),
(2) Date: Nov. 23, 2020

(87) PCT Pub. No.: WO2019/236396
PCT Pub. Date: Dec. 12, 2019

(65) Prior Publication Data
US 2021/0309671 A1    Oct. 7, 2021

Related U.S. Application Data

(60) Provisional application No. 62/680,794, filed on Jun. 5, 2018.

(51) Int. Cl.
C07D 498/22 (2006.01)
C07D 471/16 (2006.01)
C07D 491/22 (2006.01)
A61P 31/18 (2006.01)
A61K 45/06 (2006.01)

(52) U.S. Cl.
CPC ............ *C07D 498/22* (2013.01); *A61K 45/06* (2013.01); *A61P 31/18* (2018.01); *C07D 471/16* (2013.01); *C07D 491/22* (2013.01)

(58) Field of Classification Search
CPC .. C07D 498/22; C07D 471/16; C07D 491/22; A61P 31/18; A61K 45/06
See application file for complete search history.

(56) References Cited

U.S. PATENT DOCUMENTS

| | | | |
|---|---|---|---|
| 9,643,982 B2 | 5/2017 | Coleman et al. | |
| 9,714,243 B2 | 7/2017 | Embrey et al. | |
| 10,150,780 B2 | 12/2018 | Graham et al. | |
| 10,221,186 B2 | 3/2019 | Embrey | |
| 10,479,801 B2 | 11/2019 | Graham | |
| 10,829,499 B2 | 11/2020 | Graham et al. | |
| 2015/0329539 A1* | 11/2015 | Embrey | A61K 45/06 514/249 |
| 2017/0190701 A1 | 7/2017 | Yu et al. | |
| 2018/0099967 A1 | 4/2018 | Yu | |
| 2019/0322666 A1 | 10/2019 | Yu et al. | |
| 2020/0017524 A1 | 1/2020 | Graham et al. | |

FOREIGN PATENT DOCUMENTS

| | | |
|---|---|---|
| WO | 2014183532 A1 | 11/2014 |
| WO | 2016191239 A1 | 12/2016 |
| WO | 2017087257 A1 | 5/2017 |
| WO | 2017113288 A1 | 7/2017 |
| WO | 2018102634 A1 | 6/2018 |
| WO | 2019160783 A1 | 8/2019 |
| WO | 2019209667 A1 | 10/2019 |

* cited by examiner

*Primary Examiner* — Timothy R Rozof
(74) *Attorney, Agent, or Firm* — Eric Greenwald; John C. Todaro

(57) ABSTRACT

The present invention relates to Tricyclic Heterocycle Compounds of Formula (I): (I) and pharmaceutically acceptable salts or prodrug thereof, wherein $R^1$, $R^2$, $R^3$, $R^4$, $R^5$, $R^6$ and n are as defined herein. The present invention also relates to compositions comprising at least one Tricyclic Heterocycle Compound, and methods of using the Tricyclic Heterocycle Compounds for treating or preventing HIV infection in a subject.

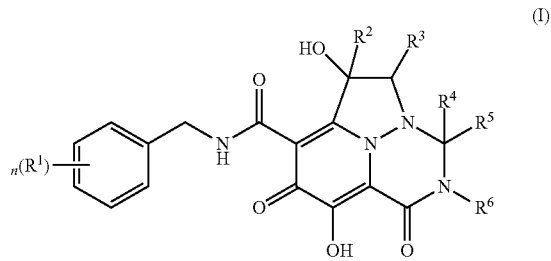

17 Claims, No Drawings

TRICYCLIC HETEROCYCLE COMPOUNDS USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2019/034783 filed May 31, 2019, which claims priority to U.S. Ser. No. 62/680,794 filed Jun. 5, 2018.

FIELD OF THE INVENTION

The present invention relates to Tricyclic Heterocycle Compounds, compositions comprising at least one Tricyclic Heterocycle Compound, and methods of using the Tricyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA, and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

SUMMARY OF THE INVENTION

In one aspect, the present invention provides Compounds of Formula (I):

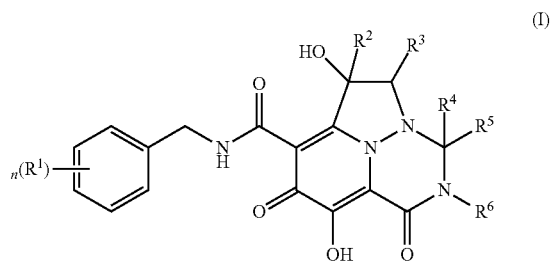

or a pharmaceutically acceptable salt thereof,
wherein:
  each occurrence of $R^1$ is independently halo or $C_{1-3}$ alkyl, wherein said alkyl groups are optionally substituted with one to three halo;
  $R^2$ is hydrogen, methyl or ethyl;
  $R^3$ is hydrogen, methyl or ethyl;
  $R^4$ is hydrogen, methyl or ethyl;
  $R^5$ is hydrogen, $C_{1-3}$ alkyl, ($C_{1-3}$ alkyl)$OR^7$ or phenyl;
  or $R^4$ and $R^5$ can be taken together with the carbon atom to which they are attached to form a 5- to 7-membered heterocyclyl group;
  $R^6$ is hydrogen, $C_{1-6}$ alkyl or ($C_{1-6}$ alkyl)$OR^7$;
  or $R^5$ and $R^6$ can be taken together with the atoms between them to form a 5- to 7-membered heterocyclyl group;
  $R^7$ is hydrogen or $C_{1-3}$ alkyl, which is optionally substituted with one to three halo;
  n is an integer between one and three.

The Compounds of Formula (I) (also referred to herein as the "Tricyclic Heterocycle Compounds") and pharmaceutically acceptable salts or prodrugs thereof may be useful, for example, for inhibiting HIV viral replication or replicon activity, or for treating or preventing HIV infection in a subject. Without being bound by any specific theory, it is believed that the Tricyclic Heterocycle Compounds inhibit HIV viral replication by inhibiting HIV Integrase.

Accordingly, the present invention provides methods for treating or preventing HIV infection in a subject, comprising administering to the subject an effective amount of at least one Tricyclic Heterocycle Compound.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Tricyclic Heterocycle Compounds, compositions comprising at least one Tricyclic Heterocycle Compound, and methods of using the Tricyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tricyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prohylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^1$) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tricyclic Heterocycle Compound or a pharmaceutically acceptable salt of the compound. The transformation may occur by various mechanisms (e.g., by metabolic or chemical processes), such as, for example, through hydrolysis in blood. For example, if a Tricyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_5$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as 3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Tricyclic Heterocycle Compound contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Tricyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl; carboxy ($C_1$-$C_6$)alkyl; amino($C_1$-$C_4$)alkyl or mono-N- or di-N,N-($C_1$-$C_6$)alkylaminoalkyl; —C($Y^4$)$Y^5$ wherein $Y^4$ is H or methyl and $Y^5$ is mono-N- or di-N,N-($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tricyclic Heterocycle Compounds can form salts which are also within the scope of this invention. Reference to a Tricyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tricyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tricyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. *Properties, Selection and Use.* (2002) Zurich: Wiley-VCH; S. Berge et al, *Journal of Pharmaceutical Sciences* (1977) 66(1) 1-19; P. Gould, International J of Pharmaceutics (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tricyclic Heterocycle Compounds may be atropisomers (e.g., substituted biaryls) and are considered as part of this invention. Enantiomers can also be directly separated using chiral chromatographic techniques.

It is also possible that the Tricyclic Heterocycle Compounds may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tricyclic Heterocycle Compound incorporates a double bond or a fused ring, both the cis- and trans-forms, as well as mixtures, are embraced within the scope of the invention.

When a subsituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

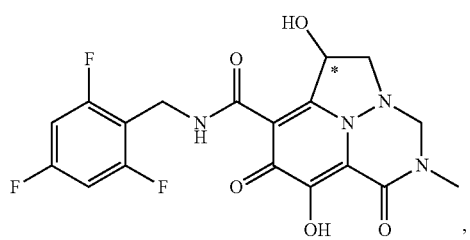 [SMILES: CN1CN2CC(O)c3c(C(=O)NCc4c(F)cc(F)cc4F)c(=O)c(O)c(n32)C1=O]

is understood to encompass both stereoisomers at the indicated chiral center, the structures of which are as follows:

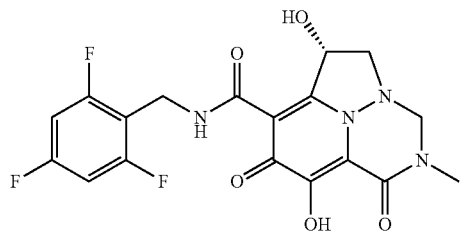 [SMILES: CN1CN2C[C@@H](O)c3c(C(=O)NCc4c(F)cc(F)cc4F)c(=O)c(O)c(n32)C1=O]

and

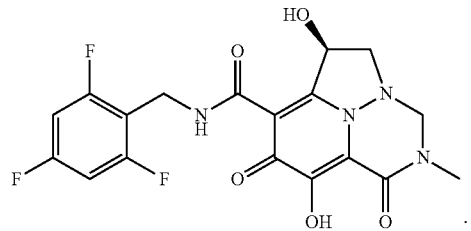 [SMILES: CN1CN2C[C@H](O)c3c(C(=O)NCc4c(F)cc(F)cc4F)c(=O)c(O)c(n32)C1=O]

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Tricyclic Heterocycle Compounds may be useful in human and veterinary medicine for treating or preventing HIV infection in a subject. In one embodiment, the Tricyclic Heterocycle Compounds can be inhibitors of HIV viral replication. In a specific embodiment, the Tricyclic Heterocycle Compounds are inhibitors of HIV-1. Accordingly, the Tricyclic Heterocycle Compounds may be useful for treating HIV infections and AIDS. In accordance with the invention, the Tricyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Tricyclic Heterocycle Compound or a pharmaceutically acceptable salt thereof. In a specific embodiment, the present invention provides methods for treating AIDS in a subject comprising administering to the subject an effective amount of at least one Tricyclic Heterocycle Compound or a pharmaceutically acceptable salt thereof.

The Compounds of Formula (I)

The present invention provides Tricyclic Heterocycle Compounds of Formula (I):

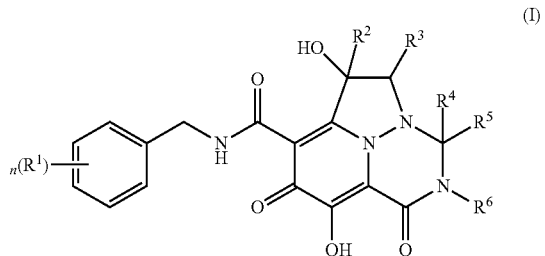

or a pharmaceutically acceptable salt thereof,
wherein:
   each occurrence of $R^1$ is independently halo or $C_{1-3}$ alkyl, wherein said alkyl groups are optionally substituted with one to three halo;
   $R^2$ is hydrogen, methyl or ethyl;
   $R^3$ is hydrogen, methyl or ethyl;
   $R^4$ is hydrogen, methyl or ethyl;
   $R^5$ is hydrogen, $C_{1-3}$ alkyl, ($C_{1-3}$ alkyl)$OR^7$ or phenyl;
   or $R^4$ and $R^5$ can be taken together with the carbon atom to which they are attached to form a 5- to 7-membered heterocyclyl group;
   $R^6$ is hydrogen, $C_{1-6}$ alkyl or ($C_{1-6}$ alkyl)$OR^7$;
   or $R^5$ and $R^6$ can be taken together with the atoms between them to form a 5- to 7-membered heterocyclyl group;
   $R^7$ is hydrogen or $C_{1-3}$ alkyl, which is optionally substituted with one to three halo;
   n is an integer between one and three.

The present invention also provides Tricyclic Heterocycle Compounds of Formula (I):

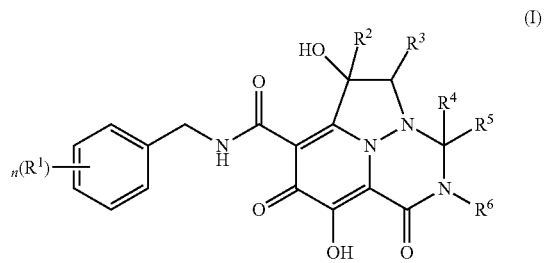

and pharmaceutically acceptable salts thereof, wherein:
   each occurrence of $R^1$ is independently halo or $C_{1-3}$ alkyl, wherein said alkyl group is optionally substituted with one to three halo;
   $R^2$ is hydrogen, methyl or ethyl;
   $R^3$ is hydrogen, methyl or ethyl;
   $R^4$ is hydrogen, methyl or ethyl;
   $R^5$ is hydrogen, $C_{1-3}$ alkyl, ($C_{1-3}$ alkyl)$OR^7$ or phenyl;
   $R^6$ is hydrogen, $C_{1-6}$ alkyl or ($C_{1-6}$ alkyl)$OR^7$;
   $R^7$ is hydrogen or $C_{1-3}$ alkyl, which is optionally substituted with one to three halo;
   n is an integer between one and three.

In an embodiment of the invention, $R^1$ is halo. In a class of the embodiment, $R^1$ is fluoro. In a class of the embodiment, $R^1$ is chloro. In another embodiment of the invention, $R^1$ is $CHF_2$. In another embodiment of the invention, $R^1$ is $CF_3$.

In an embodiment of the invention, $R^2$ is hydrogen.

In an embodiment of the invention, $R^3$ is hydrogen.

In an embodiment of the invention, $R^4$ is hydrogen or methyl. In a class of the invention, $R^4$ is hydrogen. In another class of the invention, $R^4$ is methyl.

In an embodiment of the invention, $R^5$ is hydrogen, methyl, ethyl, $CH_2OCH_3$ or phenyl. In a class of the invention, $R^5$ is hydrogen. In another class of the invention, $R^5$ is methyl. In another class of the invention, $R^5$ is ethyl. In another class of the invention, $R^5$ is $CH_2OCH_3$. In another class of the invention, $R^5$ is phenyl.

In an embodiment of the invention, $R^4$ and $R^5$ can be taken together with the carbon atom to which they are attached to form a 5- to 7-membered heterocyclyl group. In a class of the invention, $R^4$ and $R^5$ can be taken together with the carbon atom to which they are attached to form a 5- or 6-membered heterocyclyl group. In a subclass of the invention, $R^4$ and $R^5$ can be taken together with the carbon atom to which they are attached to form a 5-membered heterocyclyl group. In a further subclass of the invention, $R^4$ and $R^5$ can be taken together with the carbon atom to which they are attached to form a tetrahydrofuranyl group.

In an embodiment of the invention, $R^6$ is methyl, ethyl or $CH_2CH_2OCH_3$. In a class of the invention, $R^6$ is methyl. In another class of the invention, $R^6$ is ethyl. In another class of the invention, $R^6$ is $CH_2CH_2OCH_3$.

In an embodiment of the invention, $R^5$ and $R^6$ can be taken together with the atoms between them to form a 5- to 7-membered heterocyclyl group. In a class of the invention, $R^5$ and $R^6$ can be taken together with the atoms between them to form a 6-membered heterocyclyl group. In a subclass of the invention, $R^5$ and $R^6$ can be taken together with the atoms between them to form a morpholinyl group.

In an embodiment of the invention, n is one. In another embodiment of the invention, n is two. In another embodiment of the invention, n is three.

In another embodiment, the Compounds of Formula (I) are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors and HIV NNRTI inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors and HIV NNRTI inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HIV antiviral agents, immunomodulators, and anti-infective agents.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula (I) and (ii) a second therapeutic agent selected from the group consisting of HIV antiviral agents, immunomodulators, and anti-infective agents; wherein the pharmaceutically acceptable salt of the Compound of Formula (I) and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula (I).

(r) A method of treating HIV infection and/or reducing the likelihood or severity of symptoms of HIV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (1), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (1), (m) or (n) or the combination of (o) or (p).

Further embodiments of the present invention include the following:

(w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula (I) and (ii) or a pharmaceutically acceptable salt thereof, a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.
(aa) The combination of (z), wherein the HIV antiviral agent is an antiviral selected from the group consisting of HIV protease inhibitors and HIV NNRTI inhibitors.
(bb) A method of inhibiting HIV replication in a subject in need thereof which comprises administering to the subject an effective amount of a Compound of Formula (I) or a pharmaceutically acceptable salt thereof.
(cc) A method of treating HIV infection and/or reducing the likelihood or severity of symptoms of HIV infection in a subject in need thereof which comprises administering to the subject an effective amount of a Compound of Formula (I) or a pharmaceutically acceptable salt thereof.
(dd) The method of (cc), wherein the Compound of Formula (I) or pharmaceutically acceptable salt thereof, is administered in combination with an effective amount of at least one second therapeutic agent selected from the group consisting of HIV antiviral agents, immunomodulators, and anti-infective agents.
(ee) The method of (dd), wherein the HIV antiviral agent is an antiviral selected from the group consisting of HIV protease inhibitors and HIV NNRTI inhibitors.
(ff) A method of inhibiting HIV replication in a subject in need thereof which comprises administering to the subject the pharmaceutical composition of (w), (x) or (y) or the combination of (z) or (aa).
(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use (i) in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula (I) include compounds 1-122 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the Schemes below. Alternative synthetic pathways and analogous structures will be apparent to those skilled in the art of organic synthesis.

General List of Abbreviations
Abbreviations and acronyms employed herein include the following:

| | |
|---|---|
| Ac | Acetyl |
| Aq | Aqueous |
| ACN | Acetonitrile |
| AUC | Area under the curve |
| BAST | Bis(2-methoxyethyl)aminosulfur trifluoride |
| Bu | Butyl |
| Bz | Benzoyl |
| DBDMH | 1,3-Dibromo-5,5-dimethylhydantoin |
| DCM | Dichloromethane |
| DCE | 1,2-Dichloroethane |
| DHP | 3,4-dihydro-2H-pyran |
| DIEA, DIPEA or Hünig's base | N,N-diisopropylethylamine |
| DMAP | 4-dimethylaminopyridine |
| DME | dimethyoxyethane |
| DMF | dimethylformamide |
| DMP | Dess-Martin periodinane |
| Dppf | 1,1'-Bis(diphenylphosphino)ferrocene |
| DMSO | dimethyl sulfoxide |
| EDCI | N-ethyl-N'-(3-dimethylaminopropyl)carbodiimide hydrochloride |
| Et | Ethyl |
| EtOH | Ethanol |
| EtOAc | ethyl acetate |
| G | Grams |
| GI | Gastrointenstinal |
| H | Hour |
| HIV | human immunodeficiency virus |
| HPBCD | hydroxy propyl β-cyclodextrin |
| HPLC | high-performance liquid chromatography |
| mCPBA, CPBA | meta-Chloroperoxybenzoic |
| Hz | Hertz |
| IPA | Isopropanol |
| IV | Intravenous |
| iPr | Isopropyl |
| Ir[dF(CF$_3$)ppy]$_2$ (dtbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| L | Liter |
| LC | liquid chromatography |
| LC/MS | liquid chromatography mass spectrometry |
| LED | light-emitting diode |
| LiHMDS | lithium bis(trimethylsilyl)amide |
| Me | Methyl |
| MeOH | Methanol |
| Mg | Milligrams |
| MHZ | Megahertz |
| Min | Minute |
| μL | Microliters |
| mL | Milliliters |
| Mmol | Millimoles |
| MOM-Cl | chloromethyl methyl ether |
| MS | mass spectrometry |
| NBS | N-Bromosuccinimide |
| NHS | normal human serum |
| NIS | N-Iodosuccinimide |
| NMO | 4-methylmorpholine N-oxide |
| NMR | nuclear magnetic resonance spectroscopy |
| PBMC | peripheral blood mononuclear cell |
| Ph | Phenyl |
| P.O. | Oral |
| PTSA | para-toluenesulfonic acid |
| Pr | Propyl |
| Rpm | revolutions per minute |
| RT or rt | room temperature (ambient, about 25° C.) |
| sat or sat'd | Saturated |
| SFC | supercritical fluid chromatography |
| TBAF | Tetra-n-butylammonium fluoride |
| TBDPSCl | tert-Butyldiphenylchlorosilane |
| TBSCl | tert-Butyldimethylsilyl chloride |
| tBu | tert-butyl |
| TEA | triethylamine (Et$_3$N) |

-continued

General List of Abbreviations
Abbreviations and acronyms employed herein include the following:

| | |
|---|---|
| TEMED | tetramethylethy lenediamine |
| TFA | trifluoroacetic acid |
| TFV | Tenofovir |
| TFV-MP | Tenofovir monophosphoate |
| TFV-DP | Tenofovir diphosphate |
| THF | Tetrahydrofuran |
| TMS | Tetramethylsilane |
| UPLC | ultrahigh pressure liquid chromatography |
| UV | Ultraviolet |
| UV/VIS | ultraviolet/visible |
| W | Watt |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 µm or a Waters Acquity UPLC® BEH C18 1.0×50 mm, 1.7 µm. The flow rate was 1 mL/min, and the injection volume was 10 µL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC® BEH C18 1.0×50 mm, 1.7 µm. The flow rate was 0.3 mL/min, and the injection volume was 0.5 µL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or anonmass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 m/min for the Waters SUNFIRE™ column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CDCl$_3$ solutions, and residual CH$_3$OH peak or TMS was used as internal reference in CD$_3$OD solutions. Coupling constants (J) were reported in hertz (Hz). Chiral analytical chromatography was most commonly performed on one of CHIRALPAK© AS, CHIRALPAK®AD, CHIRALCEL© OD, CHIRALCEL©IA, or CHIRALCEL© OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% EtOH/CO2), or isopropanol in carbon dioxide (% IPA/CO2) as isocratic solvent systems. Chiral preparative chromatography was conducted on one of CHIRALPAK AS, of CHIRALPAK AD, CHIRALCEL® OD, CHIRALCEL®IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several methods for preparing the compounds of this invention are also described in the Examples. Starting materials and intermediates were purchased commercially from common catalog sources or were made using known procedures, or as otherwise illustrated.

Example 1

Preparation of Intermediate Compound Int-1

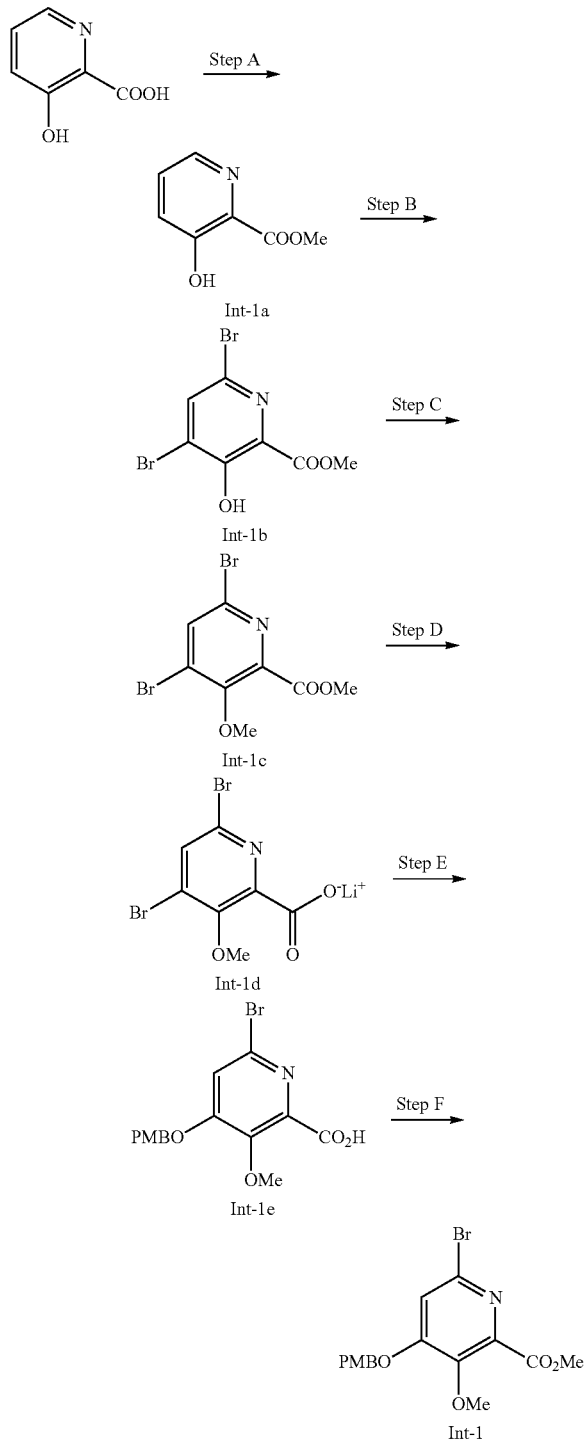

Step A—Synthesis of Compound Int-1a

To a solution of 3-hydroxypicolinic acid (340 g, 2.44 mol) in 2.8 L of MeOH stirred at 15° C., was added $H_2SO_4$ (720 g, 7.33 mol). The reaction was heated to 65° C. by an oil bath and stirred for 2 hours. After it was cooled to room temperature, the reaction content was neutralized to pH=7 by slow addition of saturated $Na_2CO_3$ aqueous solution. The resulting mixture was extracted with EtOAc. The combined organic layers were washed with brine, dried over anhydrous $Na_2SO_4$. After filtration, the filtrate was concentrated under vacuum to give compound int-1a. The crude material was used in the next reaction without further purification. $^1$HNMR (400 MHz, $CDCl_3$) δ 10.62 (s, 1H); 6.28 (d, J 4.4 Hz, 2H); 4.05 (s, 3H).

Step B—Synthesis of Compound Int-1b

To a mixture of compound int-1a (50 g, 327 mmol) in water (5.0 L) stirred at 15° C., bromine (157 g, 979 mmol) was added. The mixture was stirred at 15° C. for 5 hours. The resulting mixture was filtered, and the filter cake was washed with water and dried under vacuum to give compound int-1b. The crude material was used in the next reaction without further purification. $^1$H NMR (400 MHz, $CDCl_3$) δ 11.37 (s, 1H); 7.87 (s, 1H); 4.07 (s, 3H).

Step C—Synthesis of Compound Int-1c

To a solution of compound int-1b (200 g, 643 mmol) in acetone (4.0 L) stirred at 15° C., was added $Cs_2CO_3$ (377 g, 1.160 mol) followed by dropwise addition of iodomethane (274 g, 1930 mmol). The reaction was heated at 60° C. for 2 hours. After it was cooled to room temperature, the reaction mixture was filtered. The filter cake was washed with acetone, and the filtrate was concentrated under vacuum. The residue was purified by silica gel chromatography eluting with petroleum ether/EtOAc=25:1~10:1 to give compound int-1c. $^1$H NMR (400 MHz, $CDCl_3$) δ 7.85 (s, 1H); 3.99 (s, 3H); 3.98 (s, 3H).

Step D—Synthesis of Compound Int-1d

To a solution of compound int-1c (350 g, 1080 mmol) in THF (1.8 L) stirred at 15° C., was added water (350 mL) followed by lithium hydroxide monohydrate (54 g, 1300 mmol). The reaction mixture was stirred at 25° C. for 2 hours. The solvent was removed under vacuum to give compound int-1d. The crude material was used in the next reaction without further purification. $^1$H NMR (400 MHz, DMSO-d6) δ 7.73 (s, 1H); 3.83 (s, 3H).

Step E—Synthesis of Compound Int-1e

To a solution of compound int-1d (240 g, 757 mmol) in DMF (1.50 L) stirred at 0-5° C., was slowly added NaH (115 g, 2.88 mol, 60% wt.). It was stirred at 0~5° C. for 30 min, and then a solution of (4-methoxyphenyl)methanol (157 g, 1.14 mol) in DMF (1.50 L) was added. The reaction was stirred at 0~5° C. for 30 min, then warmed to 15° C. and stirred for 2 hours. The reaction was quenched by adding 1 L of saturated NH4Cl aqueous solution, and acidified with 4 N HCl aqueous solution until pH=4~5. The resulting mixture was extracted with EtOAc. The organic layer was washed with brine, dried over anhydrous $Na_2SO_4$, and concentrated under vacuum to give compound int-1e. Mass Calc'd for $C_{15}H_{14}NBrO_5$: 367.0, found 389.8 $(M+Na)^+$.

Step F—Synthesis of Compound Int-1

To a mixture of compound int-1e (290 g, 788 mmol) and $K_2CO_3$ (272 g, 1970 mmol) in DMF (2.5 L) stirred at 15° C., was slowly added iodomethane (355 g, 2360 mmol). The reaction was stirred at 15° C. for 12 h. The reaction mixture was diluted with 1.5 L of water and extracted with EtOAc. The organic layer was washed with brine, dried over anhydrous $Na_2SO_4$, then concentrated under vacuum. The residue was purified by silica gel chromatography eluting with petroleum ether:EtOAc:dichloromethane=10:1~2:1. The product containing fractions were combined and concentrated under vacuum. The residue was recrystallized from EtOAc/petroleum ether. The solid was collected by filtration, washed with petroleum ether, and dried under vacuum to give compound int-1. $^1$H NMR (400 MHz, CDCl$_3$): δ 7.35 (d, J 8.8 Hz, 2H); 7.16 (s, 1H); 6.95 (d, J 8.8 Hz, 2H); 5.10 (s, 2H); 3.95 (s, 3H); 3.91 (s, 3H); 3.84 (s, 3H).
Example 2
Preparation of Compounds 1 and 2
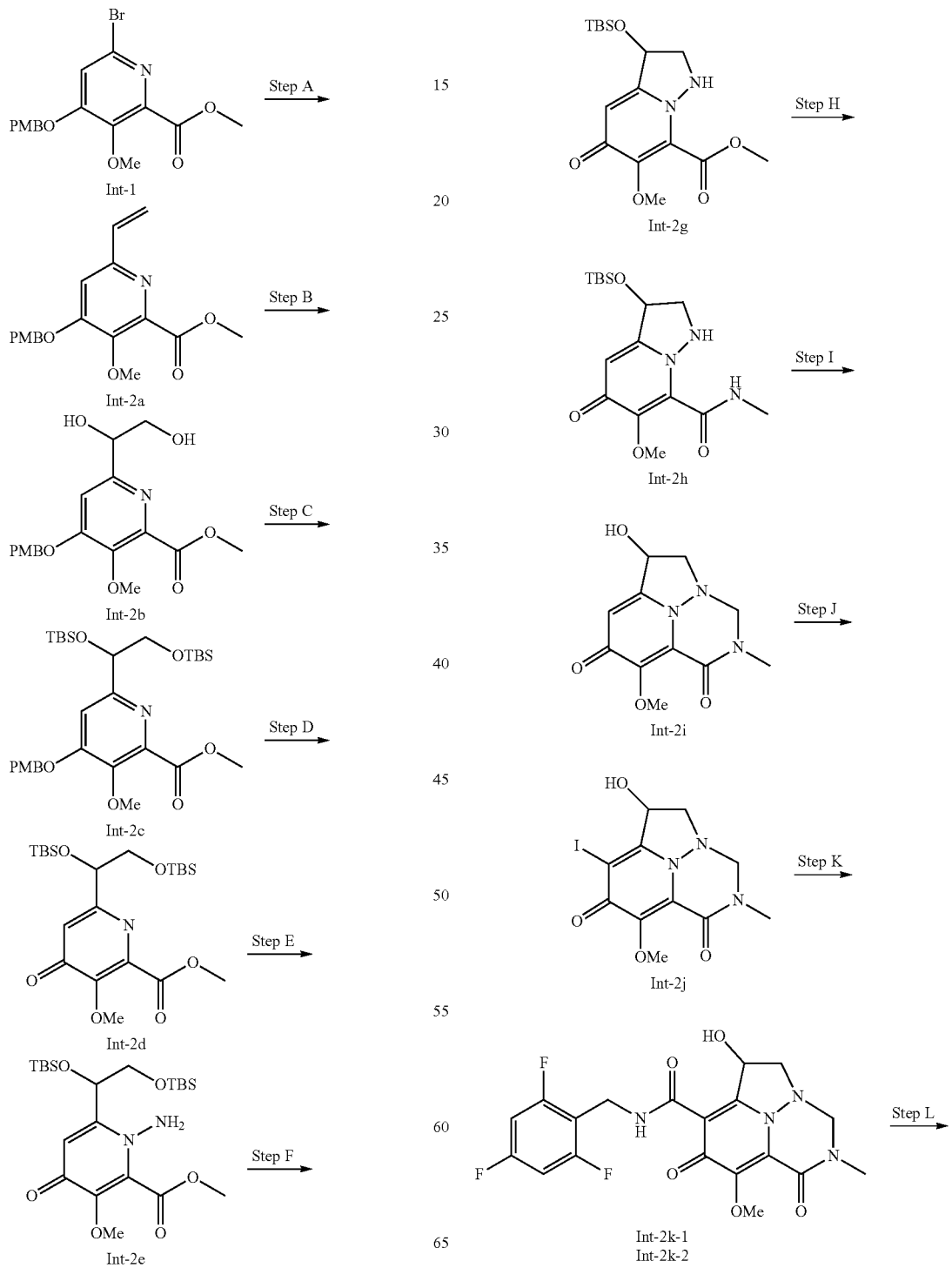

-continued

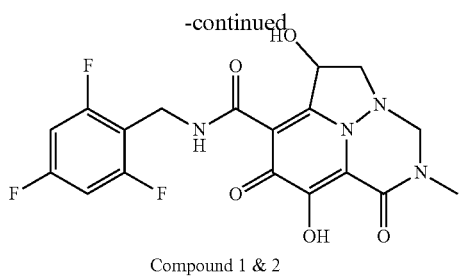

Compound 1 & 2

Step A—Synthesis of Compound Int-2a

To a solution of compound int-1 (10.53 g, 27.6 mmol) in dioxane (100 mL) and water (10 mL), was added K$_2$CO$_3$ (7.62 g, 55.1 mmol), potassium trifluoro(vinyl)borate (5.54 g, 41.3 mmol), and PdCl$_2$(dppf) (2.016 g, 2.76 mmol) sequentially. The resulting mixture was heated at 90° C. under N$_2$ for 4 hours. It was cooled to room temperature and diluted with 50 mL of water. The mixture was extracted with EtOAc (200 mL×3). The organic layer was dried over anhydrous Na$_2$SO$_4$ and concentrated. The residue was purified by silica gel chromatography (330 g column) eluting with 0-100% EtOAc/hexanes to afford compound int-2a. $^1$H NMR (400 MHz, CDCl$_3$) δ: 7.35 (d, J=8 Hz, 2H); 7.10 (s, 1H); 6.93 (d, J=8 Hz, 2H); 6.77 (m, 1H); 6.01 (m, 1H); 5.47 (m, 1H); 5.13 (s, 2H); 3.96 (s, 3H); 3.91 (s, 3H); 3.83 (s, 3H). LC/MS (m/z): 330.2 (M+H)$^+$.

Step B—Synthesis of Compound Int-2b

To a solution of compound int-2a (9 g, 27.3 mmol) in THF (100 mL), tert-BuOH (100 mL) and water (20 mL), was added a solution of 2.5% wt osmium tetroxide in tert-BuOH (17.15 mL, 1.366 mmol), followed by NMO (3.20 g, 27.3 mmol). It was stirred at rt under N$_2$ for 3 hours. To the reaction content was added 50 g of solid sodium metabisulfite, and the resulting mixture was stirred at rt for 30 min. The mixture was diluted with DCM (50 mL) and filtered. The solid cake was rinsed with DCM, and the filtrate was concentrated under vacuum. The residue was purified by silica gel chromatography (220 g column) eluting with 0-100% EtOAc/hexanes to afford compound int-2b. LC/MS (m/z): 364.2 (M+H)$^+$.

Step C—Synthesis of Compound Int-2c

To a slurring of compound int-2b (6.22 g, 17.12 mmol) in THF (100 mL), was added imidazole (4.66 g, 68.5 mmol) and tert-butylchlorodimethylsilane (7.41 mL, 42.8 mmol). The reaction was stirred at rt overnight. The resulting mixture was diluted with water (100 mL) and extracted with DCM (100 mL×3). The organic layer was dried over Na$_2$SO$_4$ and concentrated under vacuum. The residue was purified by silica gel chromatography (220 g column) eluting with 0-100% EtOAc/hexanes to afford compound int-2c. LC/MS (m/z): 592.5 (M+H)$^+$.

Step D—Synthesis of Compound Int-2d

To a solution of compound int-2c (10 g, 16.90 mmol) in MeOH (100 mL) was added Pd/C (10% wt.) (1.798 g, 1.690 mmol). The reaction was stirred at rt for 2 hours under a H$_2$ balloon. The resulting mixture was filtered through Celite and the filtrate was concentrated under vacuum to afford compound int-2d. The material was used in the next reaction without further purification. LC/MS (m/z): 472.3 (M+H)$^+$.

Step E—Synthesis of Compound Int-2e

To a solution of compound int-2d (7.5 g, 15.90 mmol) in DMF (100 mL) was added K$_2$CO$_3$ (6.59 g, 47.7 mmol) and O-(2,4-dinitrophenyl)hydroxylamine (6.33 g, 31.8 mmol). The reaction was stirred at rt overnight. The resulting mixture was filtered and the filtrate was concentrated under vacuum. The solid residue was suspended in 10 mL of DCM and filtered. The filtrate was purified by silica gel chromatography (80 g column) eluting with 0-100% EtOAc with EtOH (3:1)/hexanes to afford compound int-2e. $^1$H NMR (400 MHz, CDCl$_3$) δ: 6.48 (s, 1H); 5.55 (br, 2H); 4.88 (m, 1H); 3.93 (s, 3H); 3.91 (s, 3H); 3.89 (m, 1H); 3.66 (m, 1H); 0.89 (s, 9H); 0.86 (s, 9H); 0.10 (s, 3H); 0.05 (s, 3H); 0.01 (s, 3H); −0.01 (s, 3H). LC/MS (m/z): 487.4 (M+H)$^+$.

Step F—Synthesis of Compound Int-2f

To a solution of compound int-2e (6 g, 12.33 mmol) in DCM (50 mL) and MeOH (50 mL), was added 10-camphorsulfonic acid (2.86 g, 12.33 mmol). The reaction was stirred at rt overnight. The reaction was quenched with 3 g of triethylamine, and the solvent was removed under vacuum. The residue was purified by silica gel chromatography (120 g column) eluting with 0-100% EtOAc with EtOH (3:1)/hexanes to afford compound int-2f. LC/MS (m/z): 373.2 (M+H)$^+$.

Step G—Synthesis of Compound Int-2g

To a solution of compound int-2f (4.5 g, 12.08 mmol) in toluene (100 mL) was added 2-(tributylphosphoranylidene)acetonitrile (4.96 g, 20.54 mmol). The reaction mixture was stirred at 70° C. overnight. The solvent was removed under vacuum. The residue was purified by silica gel chromatography (220 g column) eluting with 0-100% EtOAc with EtOH (3:1)/hexanes to afford compound int-2g. $^1$H NMR (400 MHz, CDCl$_3$) δ: 6.50 (s, 1H); 5.19 (m, 1H); 3.99 (s, 3H); 3.95 (s, 3H); 3.94 (m, 1H); 3.88 (m, 1H); 0.90 (s, 9H); 0.15 (d, J=8 Hz, 6H). LC/MS (m/z): 355.2 (M+H)$^+$.

Step H—Synthesis of Compound Int-2h

To a solution of compound int-2g (1 g, 2.82 mmol) in MeOH (15 mL) was added a solution of 2.0 M methanamine in THF (14.11 mL, 28.2 mmol). The reaction was stirred at rt overnight. The solvent was removed under vacuum to afford compound int-2h. The crude material was used in the next reaction without further purification. LC/MS (m/z): 354.2 (M+H)$^+$.

Step I—Synthesis of Compound Int-2i

To a solution of compound int-2h (100 mg, 0.283 mmol) in DCE (2 mL) was added dimethoxymethane (0.250 mL, 2.83 mmol) and methanesulfonic acid (0.110 mL, 1.697 mmol). The reaction was stirred at 90° C. for 4 hours. After cooled to rt, the reaction content was concentrated under vacuum. The residue was purified by reverse phase HPLC (50 g, C18 column) eluting with 10-90% (ACN+0.05% TFA)/(water+0.05% TFA) to afford compound int-2i. LC/MS (m/z): 252.0 (M+H)$^+$.

Step J—Synthesis of Compound Int-2j

To a solution of compound int-2i (213 mg, 0.848 mmol) in MeOH (6 mL) was added NIS (381 mg, 1.696 mmol) and mCPBA (190 mg, 1.102 mmol). The reaction was stirred at 60° C. for 10 min. The solvent was removed under vacuum. The residue was purified by reverse phase HPLC (50 g, C18 column) eluting with 10-90% (ACN+0.05% TFA)/(water+0.05% TFA) to afford compound int-2j. $^1$H NMR (500 MHz, CD$_3$OD) δ: 5.46 (m, 1H); 4.67 (d, J=10 Hz, 1H); 4.53 (d, J=10 Hz, 1H); 3.95 (s, 3H); 3.67 (m, 1H); 3.47 (m, 1H); 3.17 (s, 3H). LC/MS (m/z): 378.0 (M+H)$^+$.

Step K—Synthesis of Compound Int-2k-1 and Compound Int-2k-2

A mixture of compound int-2j (101 mg, 0.268 mmol), Pd(Ph$_3$P)$_4$ (93 mg, 0.080 mmol) N,N-diethylpropan-2-amine (0.166 mL, 1.07 mmol) and (2,4,6-trifluorophenyl)methanamine (86 mg, 0.536 mmol) in DMSO (2 mL) was stirred at 80° C. under a balloon of CO for 1 hour. The reaction content was cooled to rt and filtered. The filtrate was purified by reverse phase HPLC (Waters Sunfire C18 OBD, 30×150 mm×10 μm column), eluting with 10-90% (CH₃CN+0.05% TFA)/(water+0.05% TFA). The product containing fractions were combined and concentrated under vacuum. The enantiomers of the product were further resolved by chiral preparative SFC (AS-H, 21×250 mm column; 50 g/min; 35% EtOH/CO$_2$; 210 nm) to afford compound int-2k-1 (1$^{st}$ eluting component) and compound int-2k-2 (2$^{nd}$ eluting component). LC/MS (m/z): 439.2 (M+H)$^+$.

Step L—Synthesis of Compound 1 and Compound 2

To a solution of compound int-2k-2 (47 mg, 0.107 mmol) in CH₃CN (1 mL) was added magnesium bromide (197 mg, 1.07 mmol). The mixture was stirred at 40° C. for 30 min. The mixture was filtered, and the filtrate was purified by reverse phase HPLC (Waters Sunfire C18 OBD, 10 μm, 30×150 mm column), eluting with 10-90% (ACN+0.05% TFA)/(water+0.05% TFA). The product containing fractions were collected and concentrated to remove CH₃CN, the aqueous layer was extracted with DCM (8 mL×3). The organic layer was collected and concentrated. The residue was dissolved into CH₃CN and water, followed by lyophilzation to give compound 1. $^1$H NMR (500 MHz, CDCl$_3$) δ: 11.10 (s, 1H); 6.68 (m, 2H); 5.85 (m, 1H); 4.68 (m, 2H); 4.52 (m, 2H); 3.86 (m, 1H); 3.37 (m, 1H); 3.21 (s, 3H). LC/MS (m/z): 425.2 (M+H)$^+$.

Following essentially the method employed to produce compound 1 in Step L of Example 2, compound 2 was prepared from compound int-2k-1. $^1$H NMR (500 MHz, CDCl$_3$) δ: 11.10 (s, 1H); 6.68 (m, 2H); 5.84 (m, 1H); 4.68 (m, 2H); 4.52 (m, 2H); 3.86 (br, 1H); 3.36 (br, 1H); 3.21 (s, 3H). LC/MS (m/z): 425.2 (M+H)$^+$.

Example 3

Preparation of Compounds 3-8

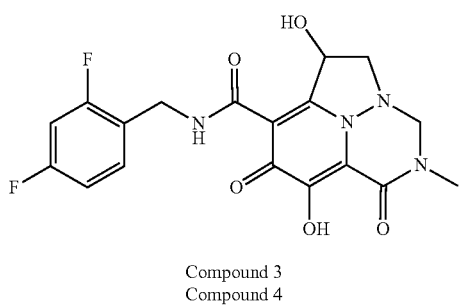

Compound 3
Compound 4

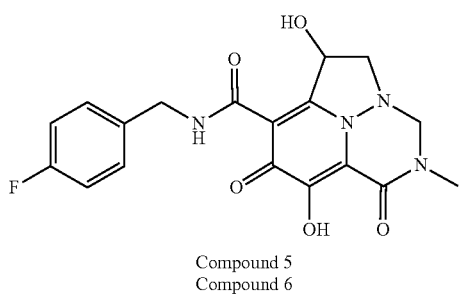

Compound 5
Compound 6

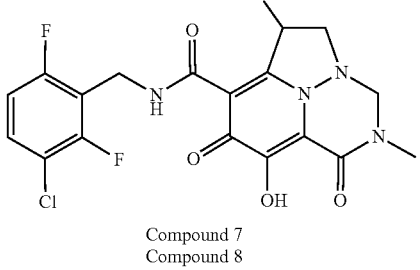

Compound 7
Compound 8

The following compounds of the present invention were made from compound int-2j using the methodology described in Example 2, and substituting the appropriate reactants and/or reagents in Step K and Step L.

Compound 3: $^1$H NMR (400 MHz, CDCl$_3$) δ: 11.14 (s, 1H); 7.35 (m, 1H); 6.82 (m, 2H); 5.84 (m, 1H); 4.64 (d, J=4 Hz, 2H); 4.51 (m, 2H); 3.84 (br, 1H); 3.37 (br, 1H); 3.21 (s, 3H). LC/MS (m/z): 407.2 (M+H)$^+$.

Compound 4: $^1$H NMR (400 MHz, CDCl$_3$) δ: 11.13 (s, 1H); 7.35 (m, 1H); 6.83 (m, 2H); 5.84 (m, 1H); 4.64 (d, J=4 Hz, 2H); 4.51 (m, 2H); 3.85 (m, 1H); 3.37 (br, 1H); 3.21 (s, 3H). LC/MS (m/z): 407.1 (M+H)$^+$.

Compound 5: $^1$H NMR (500 MHz, CDCl$_3$) δ: 11.18 (s, 1H); 7.33 (m, 2H); 7.02 (m, 2H); 5.84 (m, 1H); 4.62 (d, J=10 Hz, 2H); 4.53 (m, 2H); 3.86 (br, 1H); 3.37 (br, 1H); 3.21 (s, 3H). LC/MS (m/z): 389.2 (M+H)$^+$.

Compound 6: $^1$H NMR (500 MHz, CDCl$_3$) δ: 11.19 (s, 1H); 7.33 (m, 2H); 7.02 (m, 2H); 5.84 (m, 1H); 4.62 (d, J=10 Hz, 2H); 4.53 (m, 2H); 3.87 (br, 1H); 3.37 (br, 1H); 3.22 (s, 3H). LC/MS (m/z): 389.2 (M+H)$^+$.

Compound 7: $^1$H NMR (500 MHz, CDCl$_3$) δ: 11.14 (s, 1H); 7.31 (m, 1H); 6.88 (m, 1H); 5.84 (m, 1H); 4.73 (m, 2H); 4.51 (m, 2H); 3.84 (br, 1H); 3.36 (br, 1H); 3.20 (s, 3H). LC/MS (m/z): 441.2 (M+H)$^+$.

Compound 8: $^1$H NMR (500 MHz, CDCl$_3$) δ: 11.13 (s, 1H); 7.31 (m, 1H); 6.88 (m, 1H); 5.83 (m, 1H); 4.73 (m, 2H); 4.51 (m, 2H); 3.84 (br, 1H); 3.37 (br, 1H); 3.20 (s, 3H). LC/MS (m/z): 441.2 (M+H)$^+$.

Example 4

Preparation of Compounds 9-12

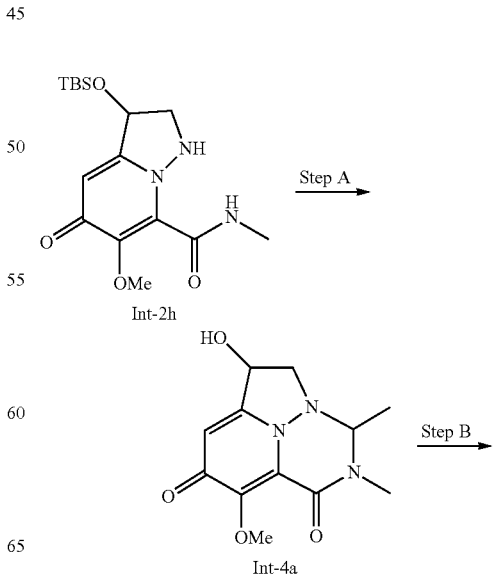

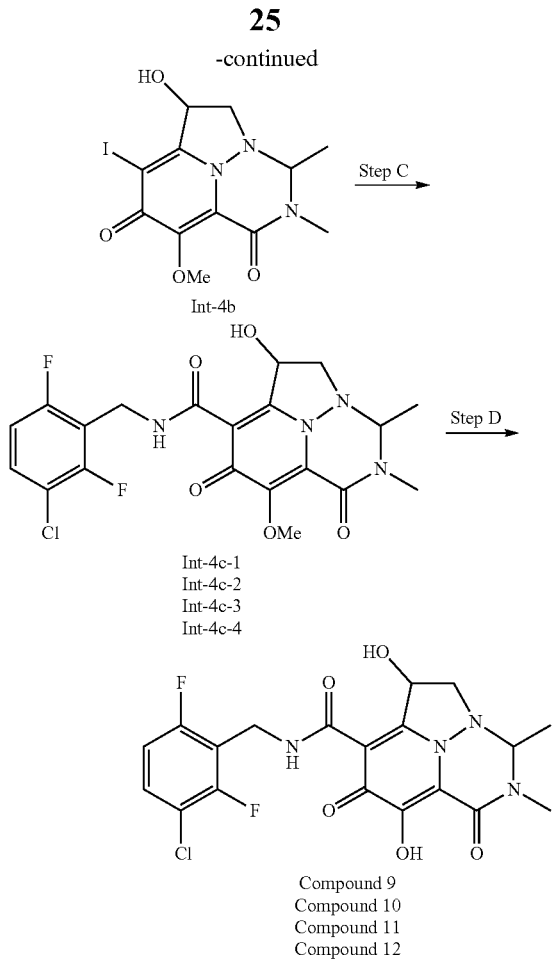

Int-4b

Int-4c-1
Int-4c-2
Int-4c-3
Int-4c-4

Compound 9
Compound 10
Compound 11
Compound 12

Step A Synthesis of Compound Int-4a

To a solution of compound int-2h (300 mg, 0.849 mmol) in DCE (4 mL) was added acetaldehyde (0.474 mL, 8.49 mmol) and methanesulfonic acid (0.331 mL, 5.09 mmol). The mixture was stirred at 90° C. for 1 h. The resulting mixture was concentrated under vacuum, the residue was purified by reverse phase HPLC (150 g, C18 column) eluting with 0-50% (ACN+0.05% TFA)/(water+0.05% TFA) to give compound int-4a. LC/MS (m/z): 266.1 (M+H)$^+$.

Step B Synthesis of Compound Int-4b

To a solution of compound int-4a (220 mg, 0.829 mmol) in MeOH (6 mL) was added NIS (373 mg, 1.659 mmol) and mCPBA (186 mg, 1.078 mmol). The mixture was stirred at 60° C. for 10 min. The solvent was removed under vacuum, the residue was purified by reverse phase HPLC (50 g, C18 column) eluting with 10-90% (ACN+0.05% TFA)/(water+ 0.05% TFA) to afford compound int-4b. LC/MS (m/z): 392.0 (M+H)$^+$.

Step C Synthesis of Compound Int-4c

A mixture of compound int-4b (70 mg, 0.179 mmol), Pd(Ph$_3$P)$_4$ (62.0 mg, 0.054 mmol), N,N-diethylpropan-2-amine (0.111 mL, 0.716 mmol) and (3-chloro-2,6-difluorophenyl)methanamine (63.6 mg, 0.358 mmol) in DMSO (2 mL) was stirred at 80° C. under a balloon of CO. The mixture was stirred at 80° C. for 1 h. The resulting mixture was cooled and filtered. The filtrate was purified by reverse phase HPLC (Waters Sunfire C18 OBD, 10 µm, 30×150 mm column), eluting with 20-100% (CH$_3$CN+0.05% TFA)/(water+0.05% TFA). The product containing fractions were combined and concentrated under vacuum. The four stereoisomers of the product were further separated by chiral preparative SFC (DAICEL CHIRALPAK AS-H, 21×250 mm column; 230 g/min; 45% EtOH/CO$_2$; 210 nm) to afford a mixture of compound int-4c-1 and compound int-4c-2 (1$^{st}$ eluting component), compound int-4c-3 (2$^{nd}$ eluting component), and compound int-4c-4 (3$^{rd}$ eluting component). The mixture of compound int-4c-1 and compound int-4c-2 was further purified by preparative chiral SFC (OJ-H, 21×250 mm column; 50 g/min; 50% EtOH/CO$_2$; 210 nm) to afford compound int-4c-1 of compound 12 (1st eluting component) and compound int-4c-2 (2$^{nd}$ eluting component). LC/MS (m/z): 469.2 (M+H)$^+$.

Step D—Synthesis of Compounds 9, 10, 11, 12

To a solution of compound int-4c-2 (10 mg, 0.023 mmol) in CH$_3$CN (0.8 mL) was added MgBr$_2$ (42.4 mg, 0.230 mmol). The mixture was stirred at 40° C. for 30 min. The mixture was filtered and the filtrate was purified with reverse phase HPLC (Waters Sunfire C18 OBD, 10 µm, 30×150 mm column) eluting with 30-90% CH$_3$CN+0.05% TFA/water+ 0.05% TFA. The product containing fractions were collected and concentrated under vacuum to remove CH$_3$CN. The remaining aqeuous mixture was extracted with DCM (8 mL×3). The organic layer was collected and concentrated. The residue was dissolved in CH$_3$CN and water, and lyophilzed to afford compound 9. $^1$H NMR (CDCl$_3$, 400 MHz) δ: 11.29 (s, 1H); 7.32 (m, 1H); 6.88 (m, 1H); 5.78 (m, 1H); 4.75 (m, 2H); 4.59 (m, 1H); 4.00 (m, 1H); 3.23 (m, 1H); 3.17 (s, 3H); 1.59 (d, J=4 Hz, 3H). LC/MS (m/z): 455.1 (M+H)$^+$.

Following essentially the method employed to produce compound 9 in Step D of Example 4, compounds 10, 11, and 12 were correspondingly prepared from compound int-2k-1, compound int-2k-3, and compound int-2k-4.

Compound 10: $^1$H NMR (400 MHz, CDCl$_3$) δ: 11.12 (s, 1H); 7.33 (m, 1H); 6.89 (m, 1H); 5.82 (m, 1H); 4.74 (m, 2H); 4.60 (m, 1H); 3.69 (m, 1H); 3.54 (m, 1H); 3.18 (s, 3H); 1.51 (d, J=4 Hz, 3H). LC/MS (m/z): 455.1 (M+H)$^+$.

Compound 11: $^1$H NMR (CDCl$_3$, 400 MHz) δ: 11.28 (s, 1H); 7.31 (m, 1H); 6.87 (m, 1H); 5.77 (m, 1H); 4.74 (m, 2H); 4.56 (m, 1H); 3.99 (m, 1H); 3.22 (m, 1H); 3.16 (s, 3H); 1.57 (d, J=4 Hz, 3H). LC/MS (m/z): 455.1 (M+H)$^+$.

Compound 12: $^1$H NMR (CDCl$_3$, 400 MHz) δ: 11.10 (s, 1H); 7.30 (m, 1H); 6.88 (m, 1H); 5.82 (m, 1H); 4.73 (m, 2H); 4.59 (m, 1H); 3.68 (m, 1H); 3.54 (m, 1H); 3.17 (s, 3H); 1.50 (d, J=4 Hz, 3H). LC/MS (m/z): 455.1 (M+H)$^+$.

Example 5

Preparation of Compounds 13-16

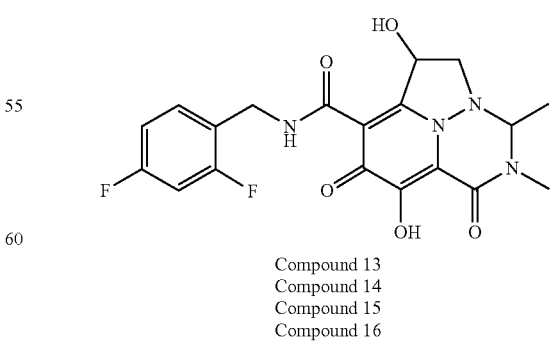

Compound 13
Compound 14
Compound 15
Compound 16

Starting from compound int-4b, using essentially the same method described in Step C and Step D in Example 4 with the exception of substituting (3-chloro-2,6-difluorophenyl)methanamine with 2,4-difluorobenzylamine, and purifying stereoisomers of the product by chiral preparative SFC (OJ-H, 21×250 mm column; 230 g/min; 40% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 35% EtOH/CO$_2$; 210 nm) to afford isomer A (1$^{st}$ eluting component) and isomer B (2$^{nd}$ eluting component) in Step C, compounds 13-16 were prepared:

Compound 13 from isomer A: $^1$H NMR (CDCl$_3$, 500 MHz) δ: 11.11 (s, 1H); 7.37 (m, 1H); 6.84 (m, 2H); 5.84 (m, 1H); 4.63 (m, 2H); 4.60 (m, 1H); 3.70 (m, 1H); 3.56 (m, 1H); 3.19 (s, 3H); 1.53 (d, J=5 Hz, 3H). LC/MS (m/z): 421.2 (M+H)$^+$.

Compound 14 from isomer B: $^1$H NMR (CDCl$_3$, 500 MHz) δ: 11.31 (s, 1H); 7.37 (m, 1H); 6.82 (m, 2H); 5.78 (m, 1H); 4.66 (m, 2H); 4.59 (m, 1H); 4.01 (m, 1H); 3.24 (m, 1H); 3.18 (s, 3H); 1.60 (d, J=5 Hz, 3H). LC/MS (m/z): 421.2 (M+H)$^+$.

Compound 15 from isomer C: $^1$H NMR (CDCl$_3$, 400 MHz) δ: 11.30 (s, 1H); 7.35 (m, 1H); 6.83 (m, 2H); 5.76 (m, 1H); 4.64 (m, 1H); 4.59 (m, 2H); 4.00 (m, 1H); 3.24 (m, 1H); 3.17 (s, 3H); 1.58 (d, J=5 Hz, 3H). LC/MS (m/z): 421.2 (M+H)$^+$.

Compound 16 from isomer D: $^1$H NMR (CDCl$_3$, 400 MHz) δ: 11.12 (s, 1H); 7.35 (m, 1H); 6.82 (m, 2H); 5.81 (m, 1H); 4.64 (m, 2H); 4.60 (m, 1H); 3.69 (m, 1H); 3.53 (m, 1H); 3.18 (s, 3H); 1.51 (d, J=5 Hz, 3H). LC/MS (m/z): 421.2 (M+H)$^+$.

Example 6

Preparation of Compounds 17-20

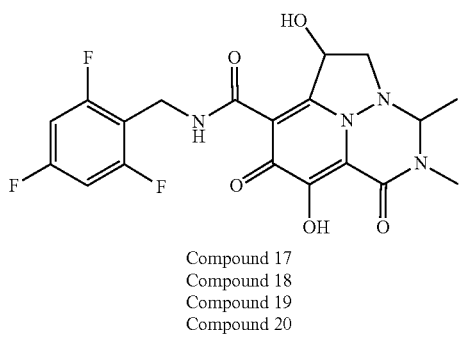 [SMILES: CC1N(C)C(=O)c2c(O)c(=O)c(C(=O)NCc3c(F)cc(F)cc3F)c3n2N1CC3O]

Compound 17
Compound 18
Compound 19
Compound 20

Starting from compound int-4b, using essentially the same method described in Step C and Step D in Example 4 with the exception of substituting (3-chloro-2,6-difluorophenyl)methanamine with 2,4,6-trifluorobenzylamine, and purifying stereoisomers of the product by chiral preparative SFC (DAICEL CHIRALPAK AS-H, 21×250 mm column; 230 g/min; 35% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 30% EtOH/CO$_2$; 210 nm) to afford isomer A (1st eluting component) and isomer B (2$^{nd}$ eluting component) in Step C, compounds 17-20 were prepared:

Compound 17 from isomer A: $^1$H NMR (CDCl$_3$, 400 MHz) δ: 11.08 (s, 1H); 6.68 (m, 2H); 5.83 (m, 1H); 4.68 (m, 2H); 4.59 (m, 1H); 3.69 (m, 1H); 3.54 (m, 1H); 3.18 (s, 3H); 1.51 (d, J=4 Hz, 3H). LC/MS (m/z): 439.1 (M+H)$^+$.

Compound 18 from isomer B: $^1$H NMR (CDCl$_3$, 400 MHz) δ: 11.25 (s, 1H); 6.68 (m, 2H); 5.78 (m, 1H); 4.69 (m, 2H); 4.57 (m, 1H); 4.00 (m, 1H); 3.23 (m, 1H); 3.18 (s, 3H); 1.59 (d, J=4 Hz, 3H). LC/MS (m/z): 439.1 (M+H)$^+$.

Compound 19 from isomer C: $^1$H NMR (CDCl$_3$, 400 MHz) δ: 11.25 (s, 1H); 6.68 (m, 2H); 5.78 (m, 1H); 4.69 (m, 2H); 4.58 (m, 1H); 4.00 (m, 1H); 3.23 (m, 1H); 3.18 (s, 3H); 1.59 (d, J=4 Hz, 3H). LC/MS (m/z): 439.1 (M+H)$^+$.

Compound 20 from isomer D: $^1$H NMR (CDCl$_3$, 400 MHz) δ: 11.08 (s, 1H); 6.68 (m, 2H); 5.83 (m, 1H); 4.68 (m, 2H); 4.60 (m, 1H); 3.70 (m, 1H); 3.54 (m, 1H); 3.18 (s, 3H); 1.51 (d, J=4 Hz, 3H). LC/MS (m/z): 439.1 (M+H)$^+$.

Example 7

Preparation of Compounds 21-24

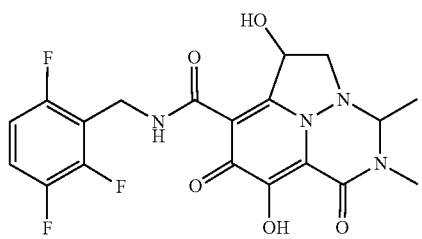

Compound 21
Compound 22
Compound 23
Compound 24

Starting from compound int-4b, using essentially the same method described in Step C and Step D in Example 4 with the exception of substituting (3-chloro-2,6-difluorophenyl)methanamine with 2,3,6-trifluorobenzylamine, and purifying stereoisomers of the product by chiral preparative SFC (DAICEL CHIRALPAK AS-H, 21×250 mm column; 50 g/min; 40% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 30% EtOH/CO$_2$; 210 nm) to afford isomer A (1st eluting component) and isomer B (2$^{nd}$ eluting component) in Step C, compounds 21-24 were prepared:

Compound 21 from isomer A: $^1$H NMR (CDCl$_3$, 500 MHz) δ: 11.08 (s, 1H); 7.09 (m, 1H); 6.86 (m, 1H); 5.82 (m, 1H); 4.74 (m, 2H); 4.66 (m, 1H); 3.68 (m, 1H); 3.56 (m, 1H); 3.17 (s, 3H); 1.52 (d, J=4 Hz, 3H). LC/MS (m/z): 439.1 (M+H)$^+$.

Compound 22 from isomer B: $^1$H NMR (CDCl$_3$, 500 MHz) δ: 11.29 (s, 1H); 7.09 (m, 1H); 6.85 (m, 1H); 6.69 (br, 1H); 5.76 (m, 1H); 4.74 (m, 2H); 4.62 (m, 1H); 4.00 (m, 1H); 3.20 (m, 1H); 3.17 (s, 3H); 1.59 (d, J=4 Hz, 3H). LC/MS (m/z): 439.1 (M+H)$^+$.

Compound 23 from isomer C: $^1$H NMR (CDCl$_3$, 500 MHz) δ: 11.30 (s, 1H); 7.07 (m, 1H); 6.84 (m, 1H); 6.68 (br, 1H); 5.75 (m, 1H); 4.74 (m, 2H); 4.60 (m, 1H); 3.99 (m, 1H); 3.23 (m, 1H); 3.16 (s, 3H); 1.57 (d, J=4 Hz, 3H). LC/MS (m/z): 439.1 (M+H)$^+$.

Compound 24 from isomer D: $^1$H NMR (CDCl$_3$, 500 MHz) δ: 11.05 (s, 1H); 7.08 (m, 1H); 6.85 (m, 1H); 5.78 (m, 1H); 4.69 (m, 2H); 4.66 (m, 1H); 3.66 (m, 1H); 3.56 (m, 1H); 3.16 (s, 3H); 1.51 (d, J=4 Hz, 3H). LC/MS (m/z): 439.1 (M+H)$^+$.

Example 8

Preparation of Compounds 25-28

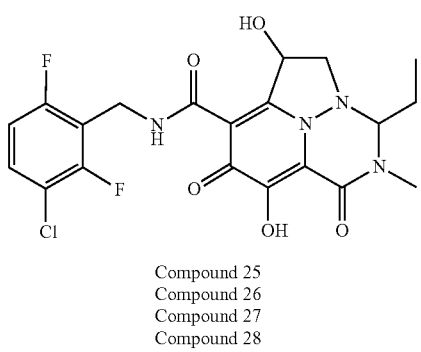 [SMILES: CCC1N(C)C(=O)c2c(O)c(=O)c(C(=O)NCc3c(F)ccc(Cl)c3F)c3n2N1CC3O]

Compound 25
Compound 26
Compound 27
Compound 28

Starting from compound int-2h, using essentially the same method described in Example 4 with the exception of substituting acetaldehyde with propionaldehyde in Step A, and purifying stereoisomers of the product in Step C by chiral preparative SFC (DAICEL CHIRALPAK AS-H, 21×250 mm column; 50 g/min; 50% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 35% EtOH/CO$_2$; 210 nm) to afford isomer A (1st eluting component) and isomer B (2$^{nd}$ eluting component), compounds 25-28 were prepared: Compound 25 from isomer A: $^1$H NMR (500 MHz, CDCl$_3$) δ: 11.00 (s, 1H); 7.31 (m, 1H); 6.88 (m, 1H); 5.83 (m, 1H); 4.72 (m, 2H); 4.49 (m, 1H); 3.62 (m, 2H); 3.20 (s, 3H); 2.12 (m, 1H); 1.82 (m, 1H); 1.08 (m, 3H). LC/MS (m/z): 469.1 (M+H)$^+$.

Compound 26 from isomer B: $^1$H NMR (500 MHz, CDCl$_3$) δ: 11.22 (s, 1H); 7.32 (m, 1H); 6.88 (m, 1H); 5.79 (m, 1H); 4.72 (m, 2H); 4.52 (m, 1H); 4.03 (m, 1H); 3.19 (m, 1H); 3.18 (s, 3H); 2.14 (m, 1H); 1.90 (m, 1H); 1.07 (m, 3H). LC/MS (m/z): 469.1 (M+H)$^+$.

Compound 27 from isomer C: $^1$H NMR (500 MHz, CDCl$_3$) δ: 11.33 (s, 1H); 7.27 (m, 1H); 6.88 (m, 1H); 5.78 (m, 1H); 4.75 (m, 2H); 4.50 (m, 1H); 4.04 (m, 1H); 3.20 (m, 1H); 3.19 (s, 3H); 2.13 (m, 1H); 1.90 (m, 1H); 1.09 (m, 3H). LC/MS (m/z): 469.1 (M+H)$^+$.

Compound 28 from isomer D: $^1$H NMR (500 MHz, CDCl$_3$) δ: 11.09 (s, 1H); 7.27 (m, 1H); 6.89 (m, 1H); 5.83 (m, 1H); 4.75 (m, 2H); 4.45 (m, 1H); 3.63 (m, 2H); 3.21 (s, 3H); 2.12 (m, 1H); 1.82 (m, 1H); 1.09 (m, 3H). LC/MS (m/z): 469.1 (M+H)$^+$.

Example 9

Preparation of Compounds 29-32

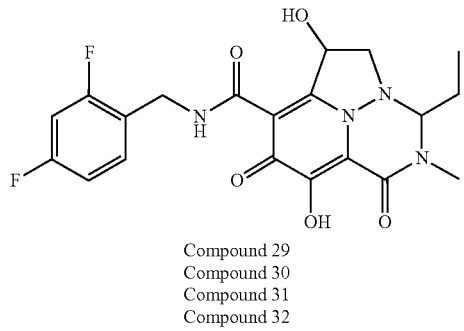 [SMILES: CCC1N(C)C(=O)c2c(O)c(=O)c(C(=O)NCc3ccc(F)cc3F)c3n2N1CC3O]

Compound 29
Compound 30
Compound 31
Compound 32

Starting from compound int-2h, using essentially the same method described in Example 4 with the exception of 1) substituting acetaldehyde with propionaldehyde in Step A, 2) substituting (3-chloro-2,6-difluorophenyl)methanamine with 2,4-difluorobenzylamine in step C, and purifying stereoisomers of the product in Step C by chiral preparative SFC (DAICEL CHIRALPAK AS-H, 21×250 mm column; 50 g/min; 50% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 30% EtOH/CO$_2$; 210 nm) to afford isomer A (1$^{st}$ eluting component) and isomer B (2$^{nd}$ eluting component), compounds 29-32 were prepared:

Compound 29 from isomer A: $^1$H NMR (500 MHz, CDCl$_3$) δ:10.99 (s, 1H); 7.37 (m, 1H); 6.84 (m, 2H); 5.75 (m, 1H); 4.62 (m, 2H); 3.60 (m, 2H); 3.22 (s, 3H); 2.13 (m, 1H); 1.84 (m, 1H); 1.09 (m, 3H). LC/MS (m/z): 435.2 (M+H)$^+$.

Compound 30 from isomer B: $^1$H NMR (500 MHz, CDCl$_3$) δ: 11.35 (s, 1H); 7.36 (m, 1H); 6.84 (m, 2H); 5.77 (m, 1H); 4.66 (m, 2H); 4.50 (m, 1H); 4.05 (m, 1H); 3.20 (m, 1H); 3.19 (s, 3H); 2.16 (m, 1H); 1.90 (m, 1H); 1.09 (m, 3H). LC/MS (m/z): 435.2 (M+H)$^+$.

Compound 31 from isomer C: $^1$H NMR (500 MHz, CDCl$_3$) δ: 11.30 (s, 1H); 7.35 (m, 1H); 6.82 (m, 2H); 5.76 (m, 1H); 4.64 (m, 2H); 4.53 (m, 1H); 4.03 (m, 1H); 3.19 (m, 1H); 3.18 (s, 3H); 2.15 (m, 1H); 1.89 (m, 1H); 1.07 (m, 3H). LC/MS (m/z): 435.1 (M+H)$^+$.

Compound 32 from isomer D: $^1$H NMR (400 MHz, CDCl$_3$) δ: 11.08 (s, 1H); 7.37 (m, 1H); 6.82 (m, 2H); 5.82 (m, 1H); 4.65 (m, 2H); 4.48 (m, 1H); 3.64 (m, 2H); 3.22 (s, 3H); 2.13 (m, 1H); 1.83 (m, 1H); 1.09 (m, 3H). LC/MS (m/z): 435.2 (M+H)$^+$.

Example 10

Preparation of Compounds 33-36

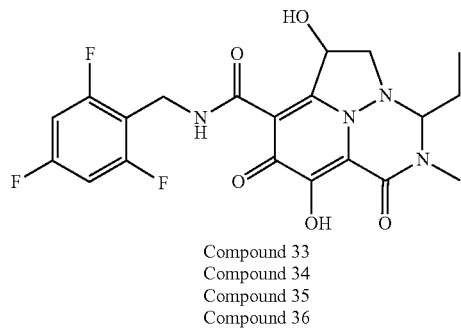 [SMILES: CCC1N(C)C(=O)c2c(O)c(=O)c(C(=O)NCc3c(F)cc(F)cc3F)c3n2N1CC3O]

Compound 33
Compound 34
Compound 35
Compound 36

Starting from compound int-2h, using essentially the same method described in Example 4 with the exception of 1) substituting acetaldehyde with propionaldehyde in Step A, 2) substituting (3-chloro-2,6-difluorophenyl)methanamine with 2,4,6-trifluorobenzylamine in step C, and purifying stereoisomers of the product in Step C by chiral preparative SFC (DAICEL CHIRALPAK AS-H, 21×250 mm column; 50 g/min; 45% EtOH/CO$_2$; 210 nm) to afford a mixture of isomer A and isomer B (1$^{st}$ eluting component), isomer C (2$^{nd}$ eluting component), and isomer D (3$^{rd}$ eluting component), and further purifying the mixture of isomer A and B by preparative chiral SFC (OJ-H, 21×250 mm column; 50 g/min; 30% EtOH/CO$_2$; 210 nm) to afford isomer A (1$^{st}$ eluting component) and isomer B (2$^{nd}$ eluting component), compounds 33-36 were prepared:

Compound 33 from isomer A: $^1$H NMR (500 MHz, CDCl$_3$) δ:11.03 (s, 1H); 6.69 (m, 2H); 5.80 (m, 2H); 4.67 (m, 2H); 4.47 (m, 1H); 3.63 (m, 2H); 3.21 (s, 3H); 2.12 (m, 1H); 1.82 (m, 1H); 1.09 (m, 3H). LC/MS (m/z): 453.1 (M+H)$^+$.

Compound 34 from isomer B: $^1$H NMR (500 MHz, CDCl$_3$) δ: 11.28 (s, 1H); 6.86 (m, 2H); 5.77 (m, 1H); 4.68 (m, 2H); 4.50 (m, 1H); 4.04 (m, 1H); 3.20 (m, 1H); 3.19 (s, 3H); 2.15 (m, 1H); 1.90 (m, 1H); 1.08 (m, 3H). LC/MS (m/z): 453.1 (M+H)$^+$.

Compound 35 from isomer C: $^1$H NMR (500 MHz, CDCl$_3$) δ:11.27 (s, 1H); 6.84 (m, 2H); 5.76 (m, 1H); 4.65 (m, 2H); 4.53 (m, 1H); 4.49 (br, 1H); 4.03 (m, 1H); 3.18 (s, 3H); 2.14 (m, 1H); 1.88 (m, 1H); 1.07 (m, 3H). LC/MS (m/z): 453.1 (M+H)$^+$.

Compound 36 from isomer D: $^1$H NMR (500 MHz, CDCl$_3$) δ: 10.99 (s, 1H); 6.68 (m, 2H); 5.80 (m, 1H); 5.69 (m, 1H); 4.66 (m, 2H); 4.50 (m, 1H); 3.62 (m, 2H); 3.19 (s, 3H); 2.11 (m, 1H); 1.81 (m, 1H); 1.07 (m, 3H). LC/MS (m/z): 453.1 (M+H)$^+$.

Example 11

Preparation of Compounds Int-11

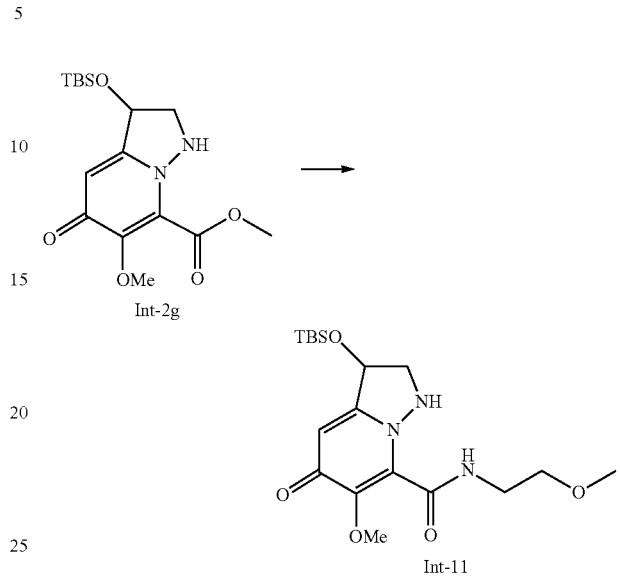

A mixture of compound int-2g (700 mg, 1.975 mmol) and 2-methoxyethanamine (2966 mg, 39.5 mmol) in THF (10 mL) was stirred at 20° C. for 12 h. The mixture was concentrated under reduced pressure, the residue was purified by flash silica gel chromatography (ISCO®; 12 g SepaFlash® Silica Flash Column; Mobile phase: 0~10% MeOH/EtOAc gradient; FlowRate: 20 mL/min) to give compound int-11. MS (M+H)$^+$: 398.2.

Example 12

Preparation of Compounds 37 and 38

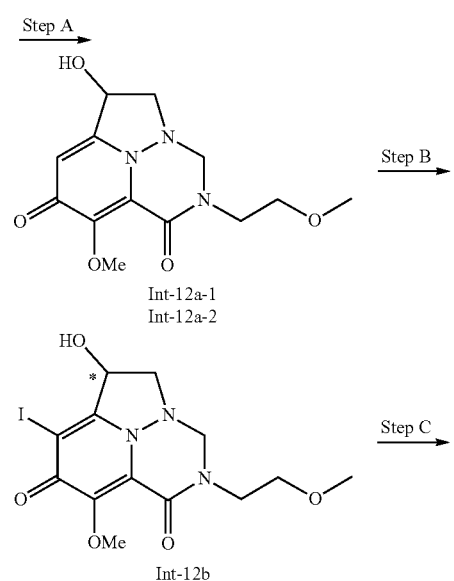

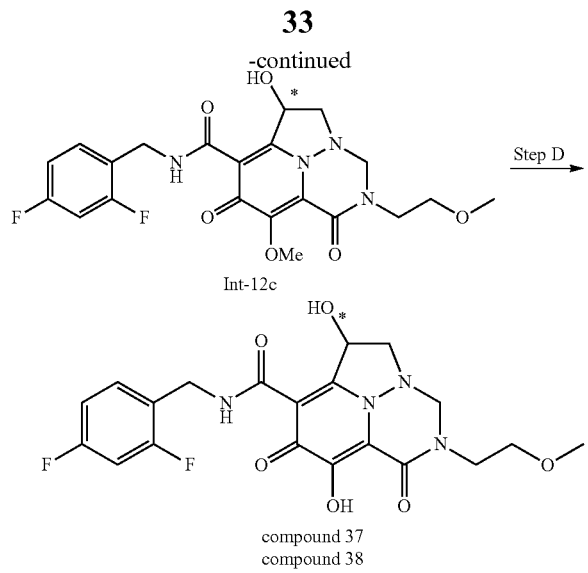

Int-12c compound 37
compound 38

Step a Synthesis of Compound Int-12a-1 and Compound Int-12a-2

A solution compound int-11 (600 mg, 1.509 mmol), dimethoxymethane (5 mL, 1.509 mmol) and MsOH (1.960 mL, 30.2 mmol) in 1,2-dichloroethane (5 mL) was stirred at 120° C. for 3 h. The mixture was concentrated under reduced pressure, the residue was purified by preparative HPLC (Column: Phenomenex Synergi Max-RP 150×50 mm×10 m; Condition: water (0.1% TFA)-MeCN, Begin B 0%, End B 30%; Gradient Time: 15 min; 100% B, Hold Time: 3 min; FlowRate: 120 mL/min). The product containing fractions were combined and concentrated (MS (M+H)$^+$: 296.1). The residue was further separated by chiral SFC (Column: Phenomenex-Cellulose-2 (250 mm×30 mm×10 µm); Mobile phase: 45% 0.1% NH3 H$_2$O+MeOH/CO$_2$; FlowRate: 80 mL/min; Injections: 100) to give compound int-12a-1 (the first eluting isomer) and compound int-12a-2 (the second eluting isomer).

Compound int-12a-1: $^1$H NMR (400 MHz, CDCl$_3$) δ: 6.57 (s, 1H); 5.34 (t, J=8.3 Hz, 1H); 4.78 (d, J=6.6 Hz, 1H); 4.44 (d, J=10.1 Hz, 1H); 3.90 (s, 4H); 3.73-3.83 (m, 1H); 3.60-3.71 (m, 1H); 3.51-3.59 (m, 2H); 3.37 (s, 4H).

Compound int-12a-2: $^1$H NMR (400 MHz, CDCl$_3$) δ: 6.52 (s, 1H); 5.33 (br d, J=8.3 Hz, 1H); 4.72-4.82 (m, 1H); 4.43 (d, J=10.5 Hz, 1H); 3.87-3.97 (m, 4H); 3.73-3.80 (m, 1H); 3.64-3.70 (m, 1H); 3.52-3.62 (m, 2H); 3.32-3.42 (m, 4H).

Step B—Synthesis of Compound Int-12b

A solution of compound int-12a-1 (100 mg, 0.339 mmol), NIS (152 mg, 0.677 mmol) and m-CPBA (68.8 mg, 0.339 mmol) in MeOH (1 mL) was stirred at 70° C. for 2 h. The mixture was concentrated in vacuum, and the residue was purified by preparative HPLC (Column: Phenomenex Synergi Max-RP 150 mm×50 mm×10 µm; Condition: water (0.1% TFA)-MeCN, Begin B 0%, End B 30%; Gradient Time: 20 min; 100% B, Hold Time: 3 min; FlowRate: 120 mL/min) to give compound int-12b. MS (M+H)$^+$: 421.8

Step C—Synthesis of Compound Int-12c

A mixture of compound int-12b (25 mg, 0.059 mmol), (2,4-difluorophenyl)methanamine (16.99 mg, 0.119 mmol), Pd(Ph$_3$P)$_4$ (34.3 mg, 0.030 mmol) and DIEA (0.031 mL, 0.178 mmol) in DMSO (1 mL) was stirred under a CO balloon (15 psi) at 80° C. for 1 h. The mixture was diluted with EtOAc (15 mL) and washed with water (3 mL) twice. The combined aqueous layer was back extracted with EtOAc (20 mL), and the combined organic layer was washed with water (3 mL). The organic layer was dried over anhydrous sodium sulfate and filtered. The filtrate was concentrated under reduced pressure, and the residue was purified by a silica gel preparative TLC plate eluting with EtOAc/MeOH (30:1) to give compound int-12c. $^1$H NMR (400 MHz, CDCl$_3$) δ: 11.31 (br s, 1H); 7.32-7.45 (m, 1H); 6.82-6.90 (m, 2H); 5.84 (dd, J=7.9, 6.5 Hz, 1H); 4.66 (d, J=5.7 Hz, 2H); 4.51-4.61 (m, 2H); 4.07-4.13 (m, 3H); 3.83 (br t, J=4.4 Hz, 1H); 3.71-3.86 (m, 2H); 3.59-3.65 (m, 2H); 3.36-3.41 (m, 4H). MS (M+H)$^+$: 465.1.

Step D—Synthesis of Compound 37 and 38

To a stirred solution of compound int-12c (15 mg, 0.032 mmol) in acetonitrile (1 mL) was added magnesium bromide (29.7 mg, 0.161 mmol) at 20° C., and the mixture was stirred at 20° C. for 12 h. The mixture was purified by preparative HPLC (Column: Boston Green ODS 150 mm×30 mm, 5 µm; Condition: water (0.1% TFA)-MeCN, Begin B 27%, End B 57%; Gradient Time: 10 min; 100% B, Hold Time: 2 min; FlowRate: 25 mL/min). The product containing fractions were co-evaporated with toluene (2×) to afford compound 37. $^1$H NMR (400 MHz, CDCl$_3$) δ: 11.14 (br s, 1H); 7.29-7.40 (m, 1H); 6.77-6.87 (m, 2H); 5.81 (t, J=7.3 Hz, 1H); 4.57-4.68 (m, 4H); 3.79-3.89 (m, 2H); 3.66-3.76 (m, 1H); 3.59-3.64 (m, 2H); 3.36 (s, 4H). MS (M+H)$^+$: 451.0.

Compound 38 was prepared from compound int-12a-2. Following essentially the method employed in Step B to Step D of Example 12. $^1$H NMR (400 MHz, CDCl$_3$) δ: 11.16 (br s, 1H); 7.31-7.39 (m, 1H); 6.77-6.88 (m, 2H); 5.82 (t, J=7.0 Hz, 1H); 4.59-4.67 (m, 4H); 3.83 (br s, 2H); 3.65-3.76 (m, 1H); 3.59-3.64 (m, 2H); 3.37 (s, 4H). MS (M+H)$^+$: 451.0.

Example 13

Preparation of Compounds 39-46

Example 13

Preparation of Compound 39-46

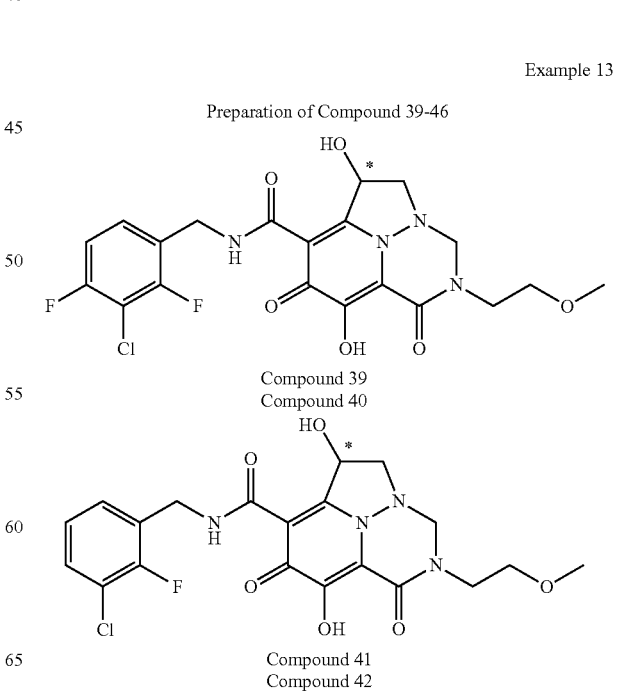

Compound 39
Compound 40

Compound 41
Compound 42

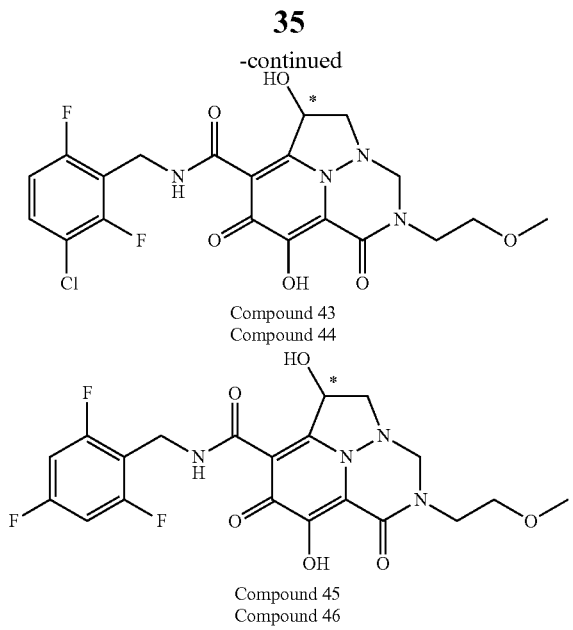

Compound 43
Compound 44

Compound 45
Compound 46

Using the methodology described in Example 12, compounds 39-46 of the present invention were made from either compound int-12a-1 or compound int-12a-2, and substituting (2,4-difluorophenyl)methanamine with the appropriate benzylamine in Step C.

Compound 39 (from compound int-12a-1): $^1$H NMR (400 MHz, CDCl$_3$) δ: 11.21 (br s, 1H); 7.26-7.30 (m, 1H); 6.93 (td, J=8.5, 1.8 Hz, 1H); 5.80 (t, J=7.5 Hz, 1H); 4.66 (br d, J=5.7 Hz, 2H); 4.61 (s, 2H); 3.79-3.88 (m, 2H); 3.66-3.76 (m, 1H); 3.59-3.64 (m, 2H); 3.30-3.38 (m, 4H). MS (M+H)$^+$: 485.0.

Compound 40 (from compound int-12a-2): $^1$H NMR (400 MHz, CDCl$_3$) δ: 11.20 (br s, 1H); 7.26-7.30 (m, 1H); 6.88-6.98 (m, 1H); 5.81 (t, J=7.3 Hz, 1H); 4.66 (br d, J=5.5 Hz, 2H); 4.61 (s, 2H); 3.78-3.89 (m, 2H); 3.66-3.76 (m, 1H); 3.59-3.64 (m, 2H); 3.30-3.39 (m, 4H). MS (M+H)$^+$: 484.9.

Compound 41 (from compound int-12a-1): $^1$H NMR (400 MHz, CDCl$_3$) δ: 11.18 (br s, 1H); 7.26-7.33 (m, 2H); 6.99-7.08 (m, 1H); 5.82 (t, J=7.4 Hz, 1H); 4.71 (br d, J=5.7 Hz, 2H); 4.61 (s, 2H); 3.80-3.88 (m, 2H); 3.68-3.75 (m, 1H); 3.60-3.63 (m, 2H); 3.36 (s, 4H). MS (M+H)$^+$: 466.9.

Compound 42 (from compound int-12a-2): $^1$H NMR (400 MHz, CDCl$_3$) δ: 11.17 (br s, 1H); 7.27-7.35 (m, 2H); 7.05 (br d, J=7.3 Hz, 1H); 5.82 (br s, 1H); 4.71 (br s, 2H); 4.61 (s, 2H); 3.83 (br s, 2H); 3.72 (br d, J=15.7 Hz, 1H); 3.62 (br s, 2H); 3.35-3.38 (m, 4H). MS (M+H)$^+$: 466.9.

Compound 43 (from compound int-12a-1): $^1$H NMR (400 MHz, CDCl$_3$) δ: 11.10 (br s, 1H); 7.27-7.35 (m, 1H); 6.87 (t, J=8.6 Hz, 1H); 5.83 (br t, J=6.8 Hz, 1H); 4.66-4.81 (m, 2H); 4.60 (s, 2H); 3.81 (br s, 2H); 3.67-3.74 (m, 1H); 3.61 (br d, J=4.6 Hz, 2H); 3.36 (s, 4H). MS (M+H)$^+$: 484.9.

Compound 44 (from compound int-12a-2): $^1$H NMR (400 MHz, CDCl$_3$) δ: 11.07 (br s, 1H); 7.21-7.30 (m, 1H); 6.81 (t, J=8.8 Hz, 1H); 5.77 (t, J=7.3 Hz, 1H); 4.60-4.74 (m, 2H); 4.53 (s, 2H); 3.71-3.83 (m, 2H); 3.60-3.69 (m, 1H); 3.52-3.59 (m, 2H); 3.30 (s, 4H). MS (M+H)$^+$: 484.9.

Compound 45 (from compound int-12a-1): $^1$H NMR (400 MHz, CDCl$_3$) δ: 11.05 (br s, 1H); 6.67 (t, J=8.2 Hz, 2H); 5.82 (t, J=7.3 Hz, 1H); 4.62-4.72 (m, 2H); 4.60 (s, 2H); 3.76-3.87 (m, 2H); 3.66-3.75 (m, 1H); 3.61 (br d, J=4.6 Hz, 2H); 3.36 (s, 4H). MS (M+H)$^+$: 469.0.

Compound 46 (from compound int-12a-2): $^1$H NMR (400 MHz, CDCl$_3$) δ: 11.07 (br s, 1H); 6.67 (t, J=8.2 Hz, 2H); 5.83 (t, J=7.4 Hz, 1H); 4.63-4.73 (m, 2H); 4.59 (s, 2H); 3.78-3.88 (m, 2H); 3.66-3.75 (m, 1H); 3.59-3.64 (m, 2H); 3.36 (s, 4H). MS (M+H)$^+$: 469.0.

Example 14

Preparation of Compound int-14b

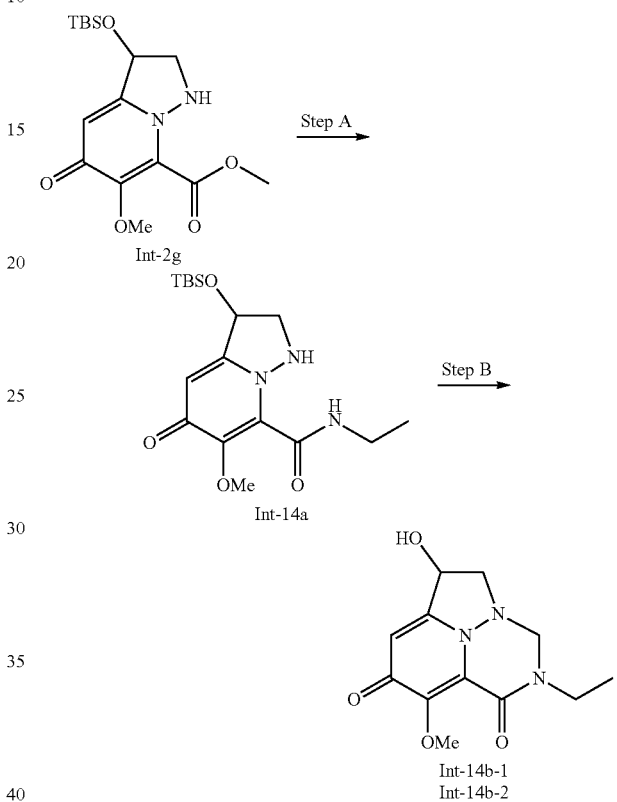

Step A—Synthesis of Compound Int-14a

A mixture of compound int-2g (1.2 g, 3.39 mmol) and ethanamine (5 mL, 25 mmol, 5 M in THF) in THF (10 mL) was stirred at 20° C. for 12 h. The reaction mixture was concentrated under reduced pressure, and the residue was purified by flash silica gel chromatography (ISCO®; 12 g SepaFlash® Silica Flash Column; Mobile phase: 0-10% MeOH/EtOAc, gradient) to give compound int-14a. $^1$HNMR (400 MHz, CDCl$_3$) δ: 7.45 (br s, 1H); 7.33 (t, J=6.4 Hz, 1H); 6.50 (s, 1H); 5.21 (t, J=6.1 Hz, 1H); 3.96 (s, 3H); 3.57-3.65 (m, 1H); 3.43-3.54 (m, 2H); 3.33 (dt, J=10.6, 6.3 Hz, 1H); 1.24-1.28 (m, 3H); 0.90 (s, 9H); 0.15 (d, J=0.9 Hz, 6H). MS (M+H)$^+$: 368.2.

Step B—Synthesis of Compound Int-14b

To a solution of compound int-14a (0.9 g, 2.449 mmol) in DCE (8 mL) was added dimethoxymethane (5.59 g, 73.5 mmol) and methanesulfonic acid (2.354 g, 24.49 mmol) at 25° C. The solution was stirred at 120° C. for 4 h under a balloon of nitrogen. The mixture was concentrated in vacuo, filtered and purified by preparative HPLC (Column: Phenomenex Synergi Max-RP 150 mm×50 mm×10 μm; Condition: water (0.1% TFA)-MeCN, Begin B 0%, End B 30%, Gradient Time: 15 min; 100% B; Hold: 3 min; FlowRate: 120 mL/min). The product containing fractions were combined and concentrated (MS (M+H)$^+$: 266.1). The residue was further separated by chiral SFC (Column: Phenomenex-Cellulose-2 (250 mm×30 mm×10 μm); Mobile phase: 55% 0.1% NH₃ H₂O+MeOH/CO₂; FlowRate: 80 mL/min) to give compound int-14b-1 (the first eluting isomer) and compound int-14b-2 (the second eluting isomer).

Compound int-14b-1: ¹HNMR (400 MHz, CDCl₃) δ: 6.59 (s, 1H); 5.29-5.41 (m, 1H); 4.75 (d, J=10.1 Hz, 1H); 4.26 (d, J=10.1 Hz, 1H); 3.87-3.96 (m, 3H); 3.72 (q, J=7.0 Hz, 1H); 3.57-3.67 (m, 1H); 3.49-3.56 (m, 2H); 1.24 (t, J=7.2 Hz, 3H). MS (M+H)⁺: 265.9.

Compound int-14b-2: ¹HNMR (400 MHz, CDCl₃) δ: 6.52 (s, 1H); 5.26-5.41 (m, 1H); 4.75 (d, J=10.1 Hz, 1H); 4.24 (d, J=10.1 Hz, 1H); 3.89 (s, 3H); 3.53-3.79 (m, 2H); 3.51 (s, 2H); 1.23 (t, J=7.2 Hz, 3H). MS (M+H)⁺: 265.9.

Example 15

Preparation of Compounds 47-64

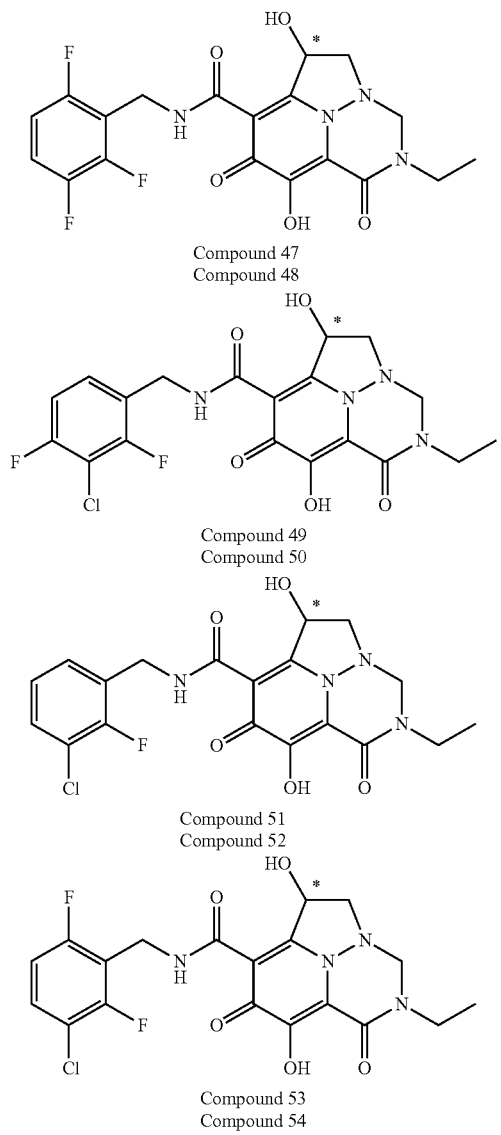

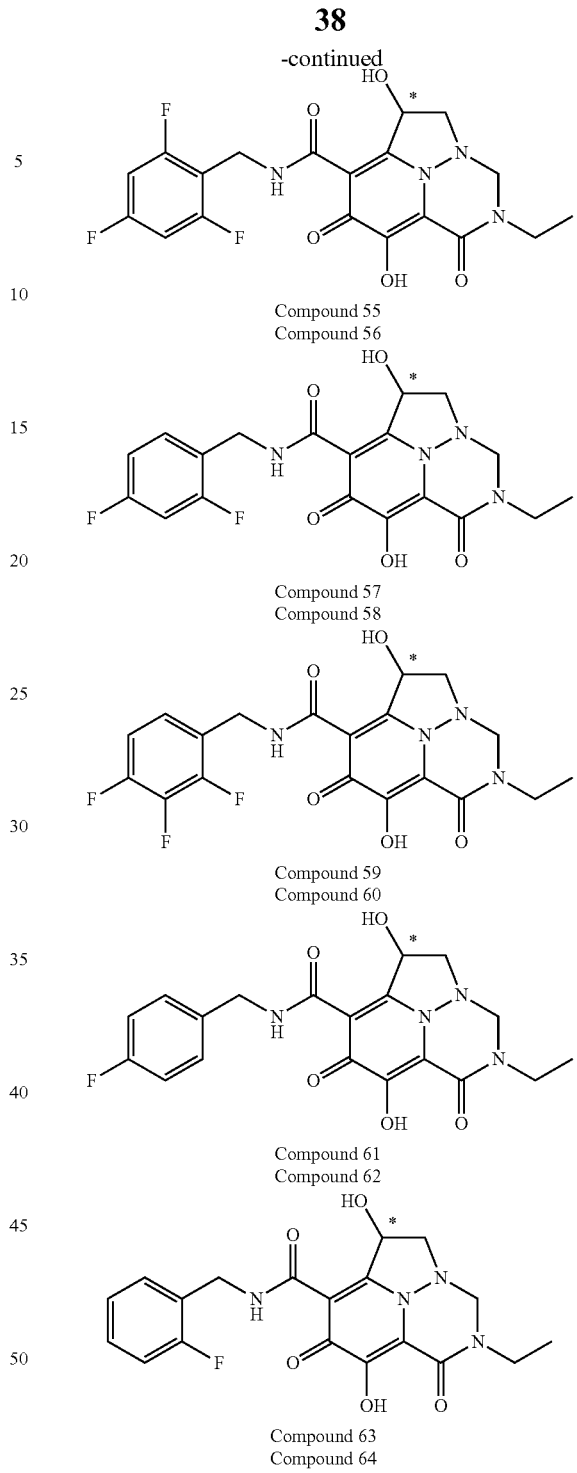

Using the methodology described in Example 12, compounds 47-64 of the present invention were made starting from either compound int-14b-1 or compound int-14b-2, and substituting (2,4-difluorophenyl)methanamine with the appropriate benzylamine in Step C.

Compound 47 (from compound int-14b-1): ¹HNMR (400 MHz, CDCl₃) δ: 11.06 (br s, 1H); 7.01 (qd, J=9.2, 5.0 Hz, 1H); 6.72-6.84 (m, 1H); 5.77 (br t, J=7.3 Hz, 1H); 4.60-4.77 (m, 2H); 4.38-4.50 (m, 2H); 3.77 (br d, J=8.8 Hz, 1H); 3.59 (q, J=7.3 Hz, 2H); 3.26-3.36 (m, 1H); 1.17-1.33 (m, 3H). MS (M+H)⁺: 439.1.

Compound 48 (from compound int-14b-2): ¹HNMR (400 MHz, CDCl₃) δ: 11.06 (br s, 1H); 7.01 (qd, J=9.2, 5.2 Hz, 1H); 6.72-6.83 (m, 1H); 5.77 (t, J=7.3 Hz, 1H); 4.61-4.74 (m, 2H); 4.37-4.49 (m, 2H); 3.78 (br t, J=8.2 Hz, 1H); 3.59 (q, J=7.1 Hz, 2H); 3.28-3.34 (m, 1H); 1.22 (t, J=7.3 Hz, 3H). MS (M+H)⁺: 439.1.

Compound 49 (from compound int-14b-1): ¹HNMR (400 MHz, CDCl₃) δ: 11.14 (br s, 1H); 7.26-7.31 (m, 1H); 6.90-6.99 (m, 1H); 5.85 (t, J=7.0 Hz, 1H); 4.67 (br s, 2H); 4.53 (q, J=9.8 Hz, 2H); 3.87-3.85 (m, 1H); 3.67 (q, J=7.0 Hz, 2H); 3.38-3.50 (m, 1H); 1.30 (t, J=7.2 Hz, 3H). MS (M+H)⁺: 454.9.

Compound 50 (from compound int-14b-2): ¹HNMR (400 MHz, CDCl₃) δ: 11.19 (br s, 1H); 7.27-7.32 (m, 1H); 6.86-7.00 (m, 1H); 5.83 (br t, J=6.8 Hz, 1H); 4.67 (br s, 2H); 4.40-4.58 (m, 2H); 3.86 (br s, 1H); 3.66 (q, J=7.3 Hz, 2H); 3.39 (br s, 1H); 1.30 (t, J=7.2 Hz, 3H). MS (M+H)⁺: 454.9.

Compound 51 (from compound int-14b-1): ¹HNMR (400 MHz, CDCl₃) δ: 11.13 (br s, 1H); 7.26-7.34 (m, 2H); 6.98-7.12 (m, 1H); 5.85 (t, J=7.0 Hz, 1H); 4.70 (br d, J=6.1 Hz, 2H); 4.50-4.57 (m, 2H); 3.84 (br t, J=8.6 Hz, 1H); 3.66 (q, J=7.2 Hz, 2H); 3.38-3.46 (m, 1H); 1.30 (t, J=7.2 Hz, 3H). MS (M+H)⁺: 436.9.

Compound 52 (from compound int-14b-2): ¹HNMR (400 MHz, CDCl₃) δ: 11.22 (br s, 1H); 7.27-7.38 (m, 2H); 6.99-7.12 (m, 1H); 5.83 (br t, J=7.5 Hz, 1H); 4.71 (br d, J=5.3 Hz, 2H); 4.42-4.58 (m, 2H); 3.86 (br s, 1H); 3.66 (q, J=7.0 Hz, 2H); 3.37 (br s, 1H); 1.29 (br t, J=7.2 Hz, 3H). MS (M+H)⁺: 436.9.

Compound 53 (from compound int-14b-1): ¹HNMR (400 MHz, CDCl₃) δ: 11.10 (br s, 1H); 7.31 (td, J=8.5, 5.8 Hz, 1H); 6.87 (td, J=8.8, 1.7 Hz, 1H); 5.84 (t, J=7.3 Hz, 1H); 4.67-4.81 (m, 2H); 4.44-4.56 (m, 2H); 3.83 (br t, J=8.6 Hz, 1H); 3.65 (q, J=7.3 Hz, 2H); 3.35-3.43 (m, 1H); 1.22-1.34 (m, 3H). MS (M+H)⁺: 454.9.

Compound 54 (from compound int-14b-2): ¹HNMR (400 MHz, CDCl₃) δ: 11.04 (br s, 1H); 7.20-7.28 (m, 1H); 6.81 (br t, J=8.3 Hz, 1H); 5.78 (br s, 1H); 4.67 (br s, 2H); 4.36-4.48 (m, 2H); 3.77 (br s, 1H); 3.59 (br d, J=6.8 Hz, 2H); 3.32 (br s, 1H); 1.22 (br t, J=7.1 Hz, 3H). MS (M+H)⁺: 455.1.

Compound 55 (from compound int-14b-1): ¹HNMR (400 MHz, CDCl₃) δ: 11.03 (br s, 1H); 6.67 (t, J=8.2 Hz, 2H); 5.85 (br t, J=7.1 Hz, 1H); 4.60-4.73 (m, 2H); 4.44-4.57 (m, 2H); 3.82 (br d, J=8.4 Hz, 1H); 3.65 (q, J=7.2 Hz, 2H); 3.38-3.43 (m, 1H); 1.28 (t, J=7.2 Hz, 3H). MS (M+H)⁺: 438.9.

Compound 56 (from compound int-14b-2): ¹HNMR (400 MHz, CDCl₃) δ: 10.99-11.12 (m, 1H); 6.67 (br t, J=7.9 Hz, 2H); 5.85 (br t, J=7.3 Hz, 1H); 4.66 (br s, 2H); 4.44-4.56 (m, 2H); 3.84 (br s, 1H); 3.65 (q, J=7.2 Hz, 2H); 3.38 (br s, 1H); 1.22-1.31 (m, 3H). MS (M+H)⁺: 438.9.

Compound 57 (from compound int-14b-1): ¹HNMR (400 MHz, CDCl₃) δ: 11.11 (br s, 1H); 7.31-7.41 (m, 1H); 6.77-6.90 (m, 2H); 5.85 (br t, J=7.2 Hz, 1H); 4.64 (br d, J=5.7 Hz, 2H); 4.44-4.57 (m, 2H); 3.85 (br s, 1H); 3.63-3.71 (m, 2H); 3.41 (br s, 1H); 1.29 (t, J=7.2 Hz, 3H). MS (M+H)⁺: 420.9.

Compound 58 (from compound int-14b-2): ¹HNMR (400 MHz, CDCl₃) δ: 11.08 (br s, 1H); 7.24-7.36 (m, 1H); 6.61-6.84 (m, 2H); 5.76 (t, J=7.4 Hz, 1H); 4.58 (br d, J=5.5 Hz, 2H); 4.34-4.51 (m, 2H); 3.78 (br d, J=7.9 Hz, 1H); 3.59 (q, J=7.4 Hz, 2H); 3.25-3.36 (m, 1H); 1.23 (t, J=7.2 Hz, 3H). MS (M+H)⁺: 421.0.

Compound 59 (from compound int-14b-1): ¹HNMR (400 MHz, CDCl₃) δ:11.14 (br s, 1H); 7.10 (br d, J=7.5 Hz, 1H); 6.89-7.00 (m, 1H); 5.85 (t, J=7.0 Hz, 1H); 4.67 (br s, 2H); 4.53 (d, J=10.1 Hz, 2H); 3.84 (br d, J=9.2 Hz, 1H); 3.67 (q, J=7.2 Hz, 2H); 3.43 (br d, J=8.8 Hz, 1H); 1.30 (t, J=7.2 Hz, 3H). MS (M+H)⁺: 439.0.

Compound 60 (from compound int-14b-2): ¹HNMR (400 MHz, CDCl₃) δ: 11.12 (br s, 1H); 7.03 (br d, J=6.2 Hz, 1H); 6.78-6.89 (m, 1H); 5.70-5.85 (m, 1H); 4.60 (br d, J=4.6 Hz, 2H); 4.33-4.51 (m, 2H); 3.79 (br s, 1H); 3.60 (q, J=7.3 Hz, 2H); 3.25-3.35 (m, 1H); 1.23 (t, J=7.2 Hz, 3H). MS (M+H)⁺: 439.0.

Compound 61 (from compound int-14b-1): ¹HNMR (400 MHz, CDCl₃) δ: 11.15 (br s, 1H); 7.30-7.43 (m, 2H); 7.02 (t, J=8.6 Hz, 2H); 5.86 (br t, J=7.0 Hz, 1H); 4.60 (br d, J=5.3 Hz, 2H); 4.47-4.57 (m, 2H); 3.84 (br s, 1H); 3.64-3.70 (m, 2H); 3.42 (br d, J=7.5 Hz, 1H); 1.30 (t, J=7.2 Hz, 3H). MS (M+H)⁺: 403.0.

Compound 62 (from compound int-14b-2): ¹HNMR (400 MHz, CDCl₃) δ: 11.07 (br s, 1H); 7.21-7.31 (m, 2H); 6.95 (t, J=8.6 Hz, 2H); 5.79 (t, J=7.3 Hz, 1H); 4.54 (br d, J=5.3 Hz, 2H); 4.36-4.49 (m, 2H); 3.77 (br t, J=8.5 Hz, 1H); 3.60 (q, J=7.4 Hz, 2H); 3.30-3.38 (m, 1H); 1.23 (t, J=7.2 Hz, 3H). MS (M+H)⁺: 403.0.

Compound 63 (from compound int-14b-1): ¹HNMR (400 MHz, CDCl₃) δ: 11.09 (br s, 1H); 7.36 (br t, J=7.7 Hz, 1H); 7.23 (br s, 1H); 7.01-7.14 (m, 2H); 5.86 (t, J=6.9 Hz, 1H); 4.69 (br d, J=5.5 Hz, 2H); 4.46-4.57 (m, 2H); 3.84 (br d, J=8.6 Hz, 1H); 3.66 (q, J=7.1 Hz, 2H); 3.41 (br s, 1H); 1.24-1.33 (m, 3H). MS (M+H)⁺: 403.1.

Compound 64 (from compound int-14b-2): ¹HNMR (400 MHz, CDCl₃) δ: 11.07 (br s, 1H); 7.28-7.35 (m, 1H); 7.09-7.18 (m, 1H); 6.97-7.06 (m, 2H); 5.77 (br t, J=7.2 Hz, 1H); 4.63 (br d, J=5.5 Hz, 2H); 4.39-4.48 (m, 2H); 3.78 (br s, 1H); 3.59 (q, J=7.1 Hz, 2H); 3.31 (br s, 1H); 1.17-1.25 (m, 3H). MS (M+H)⁺: 403.1.

Example 16

Preparation of Compounds 65-68

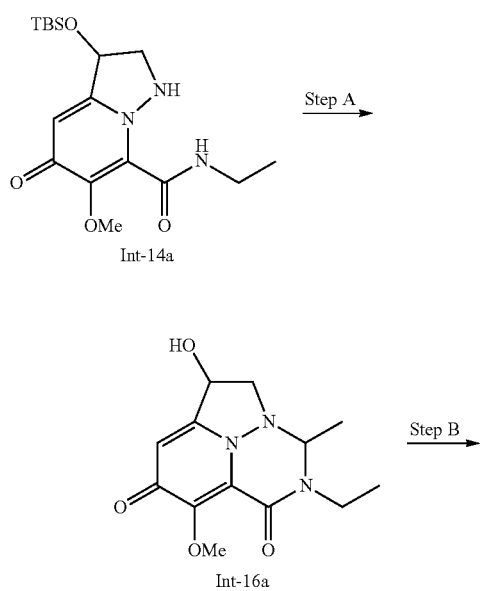

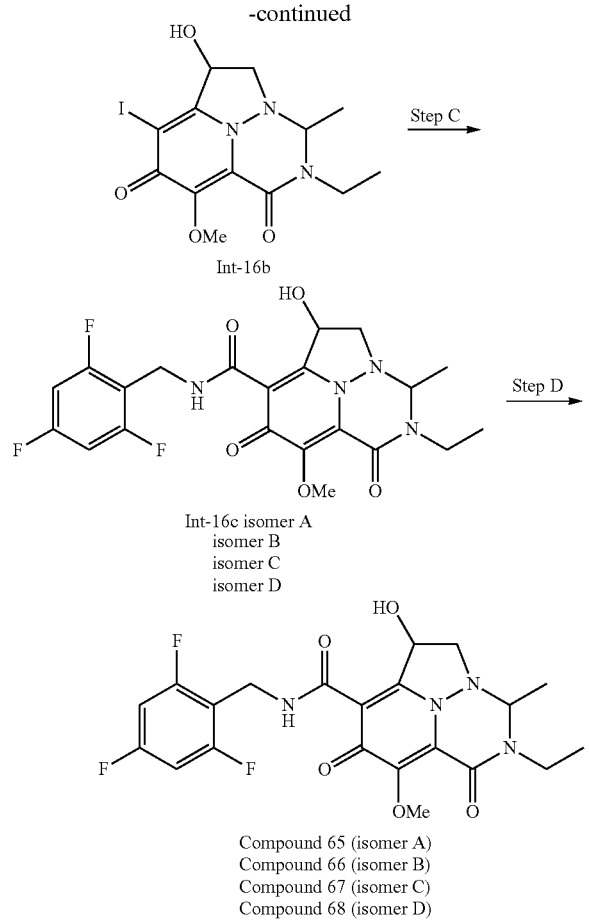

Int-16b

Int-16c isomer A
isomer B
isomer C
isomer D

Compound 65 (isomer A)
Compound 66 (isomer B)
Compound 67 (isomer C)
Compound 68 (isomer D)

Step A—Synthesis of Compound Int-16a

To a solution of compound int-14a (510 mg, 1.388 mmol) in DCE (6 mL) was added acetaldehyde (0.776 mL, 13.88 mmol) and methanesulfonic acid (0.541 mL, 8.33 mmol). The mixture was stirred at 90° C. for 1 h. The mixture was concentrated under reduced pressure and purified by reverse phase HPLC (150 g C18 aq. reverse phase column) eluting with 0-100% ACN+0.05% TFA/water+0.05% TFA to afford compound int-16a. LCMS anal. calcd. for $C_{13}H_{17}N_3O_4$: 279.29; Found: 280.17 (M+1)$^+$.

Step B—Synthesis of Compound Int-16b

To a stirred solution of compound int-16a (388 mg, 1.39 mmol) in MeOH (10 mL), NIS (625 mg, 2.78 mmol) and mCPBA (360 mg, 2.08 mmol) were added. The reaction mixture was stirred at 70° C. for 1 hour before being cooled to room temperature and evaporated under reduced pressure. The residue was purified by reverse phase HPLC (150 g C18 aq. reverse phase column), eluting with 0-100% ACN+0.05% TFA/water+0.05% TFA to afford compound int-16b. LCMS anal. calcd. for $C_{13}H_{16}IN_3O_4$: 405.18; Found: 406.08 (M+1)$^+$.

Step C—Synthesis of Compound Int-16c

Tetrakis(triphenylphosphine)palladium(0) (68 mg, 0.059 mmol), N,N-diisopropylethylamine (206 µl, 1.185 mmol) and 2,4,6-trifluorobenzylamine (95 mg, 0.592 mmol) were added to a stirred solution of compound int-16b (120 mg, 0.296 mmol) in DMSO (3 mL). The reaction mixture was degassed (3 x) and placed under a carbon monoxide balloon. The reaction mixture was stirred at 90° C. for 1 hour before being cooled to room temperature, filtered (0.45 µm syringe filter), diluted with MeOH, and purified by reverse phase HPLC (RediSep Rf C18 100 g column) eluting with 10-100% ACN+0.05% TFA/water+0.05% TFA. The product containing fractions were combined, frozen, and lyophilized to give a solid, which was further purified by chiral preparative SFC (ChiralPak AD-H, 21×250 mm column; 70 g/min; 120 bar; 30% MeOH/CO$_2$; 40° C.) to afford isomer A of compound int-16c (the 1$^{st}$ eluting component), isomer B of compound int-16c (the 2$^{nd}$ eluting component), isomer C of compound int-16c (the 3$^{rd}$ eluting component), and isomer D of compound int-16c (the 4$^{th}$ eluting component). LCMS anal. calcd. for $C_{21}H_{21}F_3N_4O_5$: 466.41; Found: 467.16 (M+1)$^+$.

Step D—Synthesis of Compound 65-68

Isomer A of compound int-16c (12.0 mg, 0.026 mmol), magnesium bromide (47 mg, 0.257 mmol), and acetonitrile (1 mL) were combined and stirred at room temperature. After 30 minutes, the reaction mixture was diluted with MeOH and filtered (0.45 µm syringe filter) before being purified by reverse phase HPLC (Waters Sunfire C18 OBD, 10 µm, 30×150 mm column) eluting with 10-90% ACN+0.05% TFA/water+0.05% TFA. Product fractions were combined and concentrated under reduced pressure until most of the ACN had been removed. The remaining aqueous solution was extracted with DCM (3×~5 mL). The combined organic layer was sequentially dried over Na$_2$SO$_4$, filtered, combined, and evaporated under reduced pressure. The resulting residue was dissolved in ACN (~5 mL), diluted with water (~5 mL), frozen, and lyophilized to afford compound 65. $^1$H NMR (500 MHz, CDCl$_3$): δ 11.10 (s, 1H); 6.70-6.65 (m, 2H); 5.84-5.81 (m, 2H); 4.68-4.65 (m, 3H); 4.01-3.88 (m, 2H); 3.40-3.33 (m, 2H); 1.56-1.54 (d, J=10 Hz, 3H); 1.27 (t, J=10 Hz, 3H). LCMS anal. calcd. for $C_{20}H_{19}F_3N_4O_5$: 452.38; Found: 453.14 (M+1)$^+$.

Following essentially the method employed to produce compound 65 in Step D of Example 16, compound 66 was prepared from isomer B of compound Int-16c. $^1$H NMR (500 MHz, CDCl$_3$): δ 11.01 (s, 1H); 6.68 (t, J=10, 2H); 5.84-5.81 (m, 1H); 4.71-4.65 (m, 3H); 4.01-3.96 (m, 1H); 3.79-3.75 (m, 1H); 3.53-3.49 (m, 1H); 3.34-3.25 (m, 1H); 1.50-1.49 (d, J=5 Hz, 3H); 1.27 (t, J=10 Hz, 3H). LCMS anal. calcd. for $C_{20}H_{19}F_3N_4O_5$: 452.38; Found: 453.13 (M+1)$^+$.

Following essentially the method employed to produce compound 65 in Step D of Example 16, compound 67 was prepared from isomer C of compound Int-16c. $^1$H NMR (500 MHz, CDCl$_3$): δ 11.10 (s, 1H); 6.70-6.66 (m, 2H); 5.85-5.81 (m, 1H); 4.68-4.66 (m, 3H); 4.01-3.88 (m, 2H); 3.38-3.32 (m, 2H); 1.56-1.54 (d, J=10 Hz, 3H); 1.27 (t, J=10 Hz, 3H). LCMS anal. calcd. for $C_{20}H_{19}F_3N_4O_5$: 452.38; Found: 453.14 (M+1)$^+$.

Following essentially the method employed to produce compound 65 in Step D of Example 16, compound 68 was prepared from isomer D of compound Int-16c. $^1$H NMR (500 MHz, CDCl$_3$): δ 10.99 (s, 1H); 6.68 (t, J=10 Hz, 2H); 5.85-5.82 (m, 1H); 4.71-4.65 (m, 3H); 4.03-3.94 (m, 1H); 3.79-3.74 (m, 1H); 3.55-3.51 (m, 1H); 3.35-3.26 (m, 1H); 1.51-1.49 (d, J=10 Hz, 3H); 1.27 (t, J=10 Hz, 3H). LCMS anal. calcd. for $C_{20}H_{19}F_3N_4O_5$: 452.38; Found: 453.14 (M+1)$^+$.

Example 17

Preparation of Compounds 69-72

Starting from compound Int-16b, using essentially the same method described in Step C and Step D of Example 16 with the exception of 1) substituting 2,4,6-trifluorobenzylamine with 3-chloro-2,6-difluorobenzylamine in Step C, 2) isolating the stereoisomers of the product in Step C by 1) chiral preparative SFC (ChiralPak AD-H, 21×250 mm column; 60 mL/min; 100 bar; 50% MeOH/CO$_2$) to afford isomers A (the 1$^{st}$ eluting component), isomer B (the 2$^{nd}$ eluting component), a mixture of isomer C (the 3$^{rd}$ eluting component)/isomer D (the 4$^{th}$ eluting component), and further purifying the mixture of isomer C and D by chiral preparative SFC (ChiralPak OJ-H, 20×250 mm column; 70 mL/min; 100 bar; 25% MeOH/CO$_2$) to afford pure isomer C and isomer D, the following compounds were prepared:

| Compound # | Structure | MS (M + H)$^+$ | $^1$H NMR |
|---|---|---|---|
| 69 (Isomer A) | 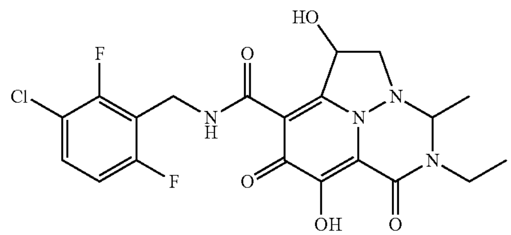 [SMILES: CCN1C(=O)c2c(O)c(=O)c(C(=O)NCc3c(F)ccc(Cl)c3F)c3n2N(CC3O)C1C] | 469.09 | (500 MHz, CDCl$_3$): δ 11.22 (s, 1H); 7.34-7.30 (m, 2H); 6.90-6.85 (m, 1H); 5.80 (t, J = 10 Hz, 1H); 4.76-4.64 (m, 3H); 4.01-3.89 (m, 2H); 3.41-3.28 (m, 2H); 1.56-1.54 (d, J = 10 Hz, 3H); 1.27 (t, J = 10 Hz, 3H). |
| 70 (Isomer B) | 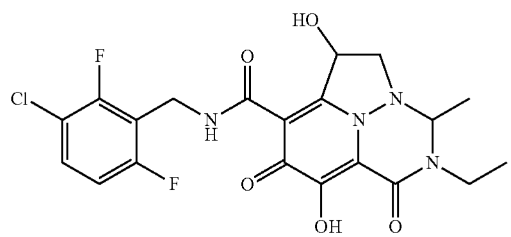 [SMILES: CCN1C(=O)c2c(O)c(=O)c(C(=O)NCc3c(F)ccc(Cl)c3F)c3n2N(CC3O)C1C] | 469.08 | (500 MHz, CDCl$_3$): δ 11.07 (s, 1H); 7.34-7.30 (m, 1H); 6.90-6.86 (m, 1H); 5.84-5.80 (m, 2H); 4.74-4.65 (m, 3H); 4.01-3.94 (m, 1H); 3.80-3.75 (m, 1H); 3.52-3.48 (m,1H); 3.34-3.25 (m, 1H); 1.51-1.49 (d, J = 10 Hz, 3H); 1.27 (t, J = 10 Hz, 3H). |
| 71 (Isomer C) | 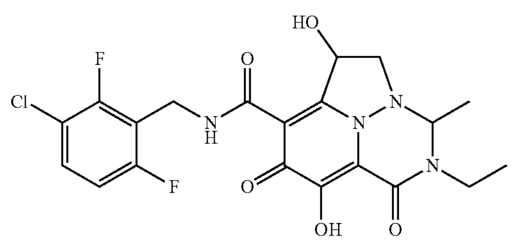 [SMILES: CCN1C(=O)c2c(O)c(=O)c(C(=O)NCc3c(F)ccc(Cl)c3F)c3n2N(CC3O)C1C] | 469.10 | (500 MHz, CDCl$_3$): δ 11.04 (s, 1H); 7.34-7.29 (m, 1H); 6.90-6.86 (m, 1H); 5.82-5.79 (m, 2H); 4.73-4.68 (m, 3H); 4.02-3.95 (m, 1H); 3.78-3.74 (m, 1H); 3.54-3.50 (m,1H); 3.33-3.27 (m, 1H); 1.51-1.49 (d, J = 10 Hz, 3H); 1.27 (t, J = 10 Hz, 3H). |
| 72 (Isomer D) | 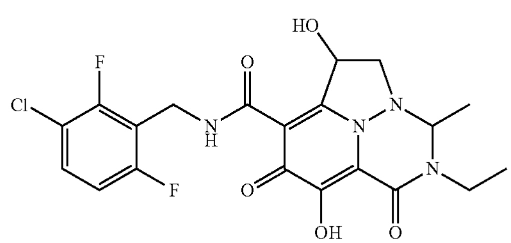 [SMILES: CCN1C(=O)c2c(O)c(=O)c(C(=O)NCc3c(F)ccc(Cl)c3F)c3n2N(CC3O)C1C] | 469.12 | 500 MHz, CDCl$_3$): δ 11.17 (s, 1H); 7.34-7.28 (m, 2H); 6.90-6.86 (m, 1H); 5.81 (t, J = 10 Hz, 1H); 4.80-4.64 (m, 3H); 4.01-3.88 (m, 2H); 3.40-3.30 (m, 2H); 1.56-1.54 (d, J = 10 Hz, 3H); 1.27 (t, J = 10 Hz, 3H). |

Example 18

Preparation of Compounds 73-76

Starting from compound Int-16b, using essentially the same method described in Step C and Step D in Example 16 with the exception of 1) substituting 2,4,6-trifluorobenzylamine with 4-difluoromethylbenzylamine in Step C, 2) isolating the stereoisomers of the product in Step C by chiral preparative SFC (ChiralPak AD-H, 21×250 mm column; 60 mL/min; 100 bar; 50% MeOH/CO$_2$) to afford isomers A (the 1$^{st}$ eluting component), isomer B (the 2$^{nd}$ eluting component), isomer C (the 3$^{rd}$ eluting component), and isomer D (the 4$^{th}$ eluting component), the following compounds were prepared:

| Compound # | Structure | MS (M + H)$^+$ | $^1$H NMR |
|---|---|---|---|
| 73 (Isomer A) | 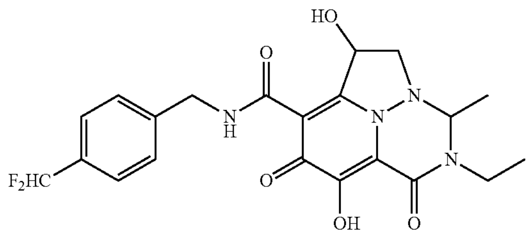 [SMILES: CCN1C(=O)c2c(O)c(=O)c(C(=O)NCc3ccc(C(F)F)cc3)c3n2N(CC3O)C1C] | 449.16 | (500 MHz, CDCl$_3$): δ 11.29 (s, 1H); 7.49-7.43 (m, 4H); 6.63 (t, J = 70 Hz, 2H); 5.81 (t, J = 10 Hz, 1H); 4.70-4.67 (m, 3H); 4.01-3.92 (m, 2H); 3.41-3.31 (m, 2H); 1.57-1.55 (d, J = 10 Hz, 3H); 1.26 (t, J = 10 Hz, 3H). |
| 74 (Isomer B) | 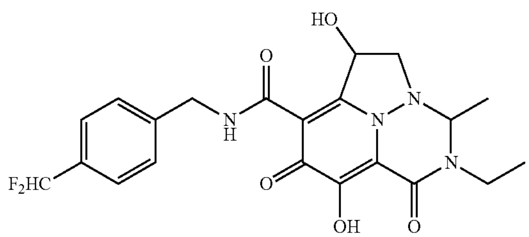 [SMILES: CCN1C(=O)c2c(O)c(=O)c(C(=O)NCc3ccc(C(F)F)cc3)c3n2N(CC3O)C1C] | 449.17 | (500 MHz, CDCl$_3$): δ 11.18 (s, 1H); 7.49-7.43 (m, 4H); 6.63 (t, J = 70 Hz, 2H); 5.82-5.79 (m, 2H); 4.72-4.68 (m, 3H); 4.02-3.96 (m, 1H); 3.78-3.73 (m, 1H); 3.52-3.49 (m, 1H); 3.33-3.28 (m, 1H); 1.51-1.50 (d, J = 5 Hz, 3H); 1.30 (t, J = 10 Hz, 3H). |
| 75 (Isomer C) | 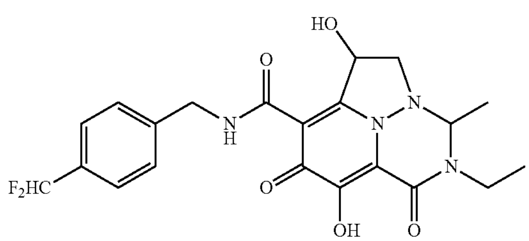 [SMILES: CCN1C(=O)c2c(O)c(=O)c(C(=O)NCc3ccc(C(F)F)cc3)c3n2N(CC3O)C1C] | 449.18 | (500 MHz, CDCl$_3$): δ 11.28 (s, 1H); 7.49-7.43 (m, 4H); 6.63 (t, J = 70 Hz, 2H); 5.83-5.79 (m, 2H); 4.70-4.68 (m, 3H); 4.02-3.89 (m, 2H); 3.43-3.31 (m, 2H); 1.57-1.55 (d, J = 10 Hz, 3H); 1.28 (t, J = 10 Hz, 3H). |
| 76 (Isomer D) | 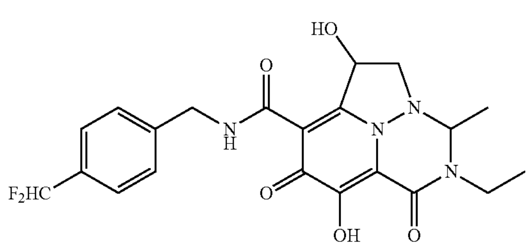 [SMILES: CCN1C(=O)c2c(O)c(=O)c(C(=O)NCc3ccc(C(F)F)cc3)c3n2N(CC3O)C1C] | 449.20 | (500 MHz, CDCl$_3$): δ 11.19 (s, 1H); 7.49-7.43 (m, 4H); 6.62 (t, J = 70 Hz, 2H); 5.82-5.80 (m, 2H); 4.69-4.68 (m, 3H); 4.02-3.96 (m, 1H); 3.79-3.74 (m, 1H); 3.52-3.49 (m, 1H); 3.32-3.31 (m, 1H); 1.51-1.49 (d, J = 10 Hz, 3H); 1.29 (t, J = 10 Hz, 3H). |

Example 19

Preparation of Compounds 77-80

Starting from compound Int-16b, using essentially the same method described in Step C and Step D in Example 16 with the exception of 1) substituting 2,4,6-trifluorobenzylamine with 4-trifluoromethylbenzylamine, 2) isolating the stereoisomers of the product in Step C by chiral preparative SFC (ChiralPak AD-H, 21×250 mm column; 60 mL/min; 100 bar; 50% MeOH/CO$_2$) to afford isomers A (the 1$^{st}$ eluting component), isomer B (the 2$^{nd}$ eluting component), isomer C (the 3$^{rd}$ eluting component), and isomer D (the 4$^{th}$ eluting component), the following compounds were prepared.

| Compound # | Structure | MS (M + H)$^+$ | $^1$H NMR |
|---|---|---|---|
| 77 (Isomer A) | 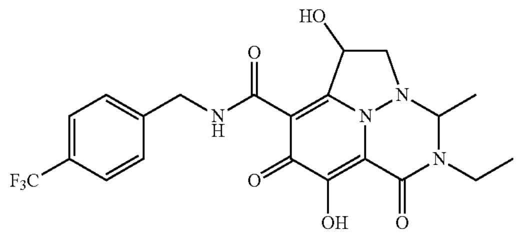 [SMILES: CCN1C(=O)c2c(O)c(=O)c(C(=O)NCc3ccc(C(F)(F)F)cc3)c3n2N(CC3O)C1C] | 467.15 | (500 MHz, CDCl$_3$): δ 11.30 (s, 1H); 7.59-7.45 (m, 4H); 5.81 (t, J = 10 Hz, 1H); 4.71-4.68 (m, 3H); 4.02-3.89 (m, 2H); 3.41-3.34 (m, 2H); 1.57-1.55 (d, J = 10 Hz, 3H); 1.28 (t, J = 10 Hz, 3H). |
| 78 (Isomer B) | 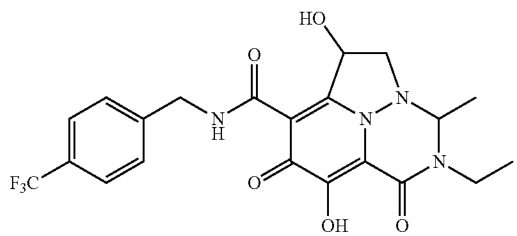 [SMILES: CCN1C(=O)c2c(O)c(=O)c(C(=O)NCc3ccc(C(F)(F)F)cc3)c3n2N(CC3O)C1C] | 467.21 | (500 MHz, CDCl$_3$): δ 11.19 (s, 1H); 7.60-7.46 (m, 4H); 5.82-5.81 (m, 2H); 4.71-4.69 (m, 3H); 4.04-3.95 (m, 1H); 3.79-3.74 (m, 1H); 3.54-3.50 (m, 1H); 3.35-3.26 (m, 1H); 1.52-1.50 (d, J = 10 Hz, 3H); 1.30 (t, J = 10 Hz, 3H). |
| 79 (Isomer C) | 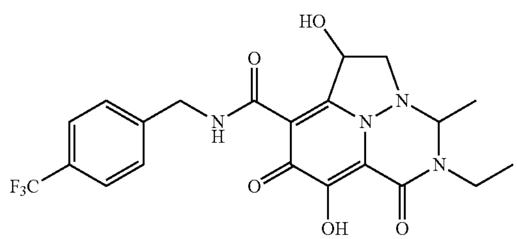 [SMILES: CCN1C(=O)c2c(O)c(=O)c(C(=O)NCc3ccc(C(F)(F)F)cc3)c3n2N(CC3O)C1C] | 467.20 | (500 MHz, CDCl$_3$): δ 11.28 (s, 1H); 7.60-7.45 (m, 4H); 5.83 (t, J = 10 Hz, 1H); 4.72-4.70 (m, 3H); 4.01-3.91 (m, 2H); 3.39-3.34 (m, 2H); 1.57-1.55 (d, J = 10 Hz, 3H); 1.28 (t, J = 10 Hz, 3H). |
| 80 (Isomer D) | 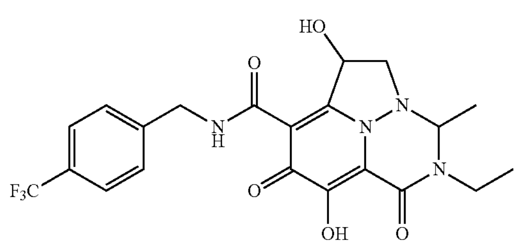 [SMILES: CCN1C(=O)c2c(O)c(=O)c(C(=O)NCc3ccc(C(F)(F)F)cc3)c3n2N(CC3O)C1C] | 467.22 | (500 MHz, CDCl$_3$): δ 11.20 (s, 1H); 7.60-7.46 (m, 4H); 5.82-5.78 (m, 1H); 4.74-4.66 (m, 3H); 4.04-3.95 (m, 1H); 3.79-3.74 (m, 1H); 3.53-3.49 (m, 1H); 3.35-3.26 (m, 1H); 1.51-1.50 (d, J = 5 Hz, 3H); 1.30 (t, J = 10 Hz, 3H). |

Example 20

Preparation of Compounds 81-84

Starting from compound Int-16b, using essentially the same method described in Step C and Step D in Example 16 with the exception of 1) substituting 2,4,6-trifluorobenzylamine with 2,3,6-trifluorobenzylamine, 2) isolating the stereoisomers of the product in Step C by chiral preparative SFC (ChiralPak AD-H, 21×250 mm column; 60 mL/min; 100 bar; 25% EtOH/CO$_2$) to afford isomers A (the 1$^{st}$ eluting component), isomer B (the 2$^{nd}$ eluting component), isomer C (the 3$^{rd}$ eluting component), and isomer D (the 4$^{th}$ eluting component), the following compounds were prepared:

| Compound # | Structure | MS (M + H)$^+$ | $^1$H NMR |
|---|---|---|---|
| 81 (Isomer A) | 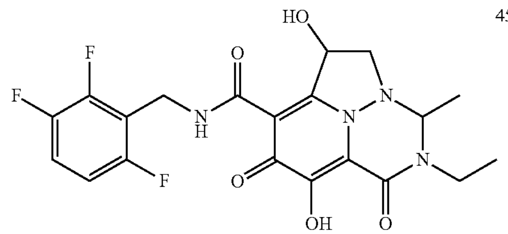 | 453.35 | (500 MHz, CDCl$_3$): δ 11.22 (s, 1H); 7.09-7.06 (m, 1H); 6.84 (s, 1H); 5.81-5.79 (m, 1H); 4.75-4.64 (m, 3H); 4.01-3.89 (m, 2H); 3.41-3.28 (m, 2H); 1.56-1.54 (d, J = 10 Hz, 3H); 1.27 (t, J = 10 Hz, 3H). |
| 82 (Isomer B) | 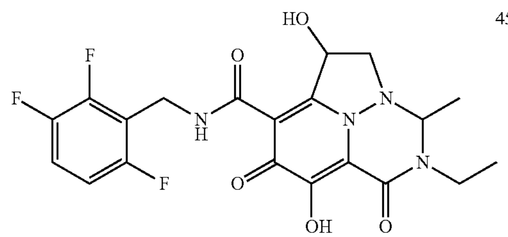 | 453.17 | (500 MHz, CDCl$_3$): δ 11.11 (s, 1H); 7.10-7.08 (m, 1H); 6.87-6.84 (m, 1H); 5.83-5.80 (m, 1H); 4.74-4.64 (m, 3H); 4.03-3.94 (m, 1H); 3.80-3.76 (m, 1H); 3.50-3.40 (m,1H); 3.33-3.24 (m, 1H); 1.56-1.54 (d, J = 10 Hz, 3H); 1.27 (t, J = 10 Hz, 3H). |
| 83 (Isomer C) | 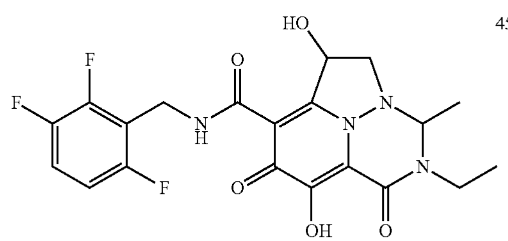 | 453.11 | (500 MHz, CDCl$_3$): δ 11.20 (s, 1H); 7.10-7.06 (m, 1H); 6.86-6.84 (m, 1H); 5.83-5.79 (m, 1H); 4.79-4.64 (m, 3H); 4.01-3.89 (m, 2H); 3.41-3.29 (m, 2H); 1.56-1.54 (d, J = 10 Hz, 3H); 1.27 (t, J = 10 Hz, 3H). |
| 84 (Isomer D) | 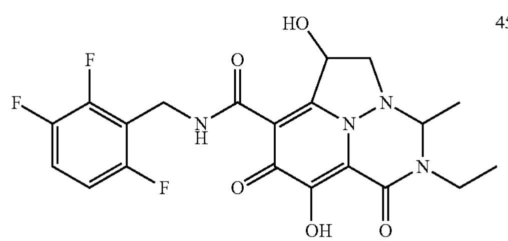 | 453.14 | (500 MHz, CDCl$_3$): δ 11.09 (s, 1H); 7.12-7.04 (m, 1H); 6.87-6.82 (m, 1H); 5.83-5.80 (m, 1H); 4.74-4.66 (m, 3H); 4.03-3.94 (m, 1H); 3.80-3.75 (m, 1H); 3.51-3.48 (m,1H); 3.34-3.27 (m, 1H); 1.56-1.54 (d, J = 10 Hz, 3H); 1.27 (t, J = 10 Hz, 3H). |

Example 21

Preparation of Compounds 85-88

Starting from compound Int-16b, using essentially the same method described in Step C and Step D in Example 16 with the exception of 1) substituting 2,4,6-trifluorobenzylamine with 4-trifluorolbenzylamine, 2) isolating the stereoisomers of the product in Step C by chiral preparative SFC (ChiralPak AS-H, 21×250 mm column; 60 mL/min; 100 bar; 15% EtOH/CO$_2$) to afford isomers A (the 1$^{st}$ eluting component), isomer B (the 2$^{nd}$ eluting component), isomer C (the 3$^{rd}$ eluting component), and isomer D (the 4$^{th}$ eluting component), the following compounds were prepared:

| Compound # | Structure | MS (M + H)$^+$ | $^1$H NMR |
|---|---|---|---|
| 85 (Isomer A) | 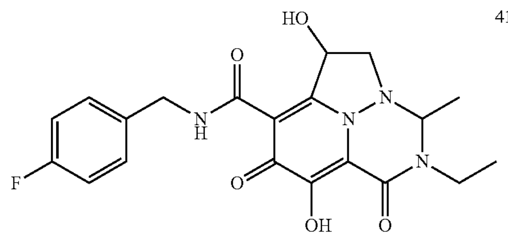 | 417.19 | (500 MHz, CDCl$_3$): δ 11.08 (s, 1H); 7.34-7.31(m, 2H); 7.04-7.00 (m, 2H); 5.79 (s, 1H); 4.73-4.60 (m, 3H); 4.01-3.96 (m, 1H); 3.76-3.67 (m, 1H); 3.53-3.49 (m,1H); 3.35-3.26 (m, 1H); 1.51-1.50 (d, J =5 Hz, 3H); 1.29 (t, J = 10 Hz, 3H). |
| 86 (Isomer B) | 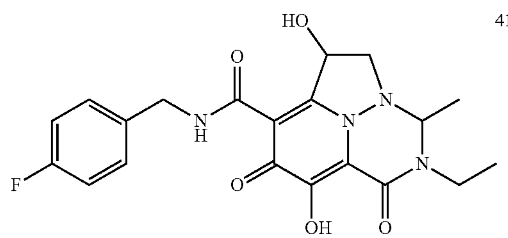 | 417.21 | (500 MHz, CDCl$_3$): δ 11.19 (s, 1H); 7.34-7.30 (m, 2H); 7.04-6.99 (m, 2H); 5.82 (t, J = 10 Hz, 1H); 4.72-4.60 (m, 3H); 4.02-3.89 (m, 2H); 3.41-3.32 (m, 2H); 1.56-1.55 (d, J = 5 Hz, 3H); 1.28 (t, J = 10 Hz, 3H). |
| 87 (Isomer C) | 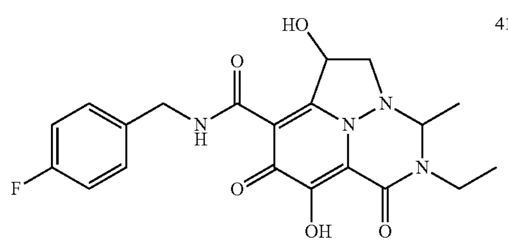 | 417.22 | (500 MHz, CDCl$_3$): δ 11.19 (s, 1H); 7.34-7.31 (m, 2H); 7.03-6.99 (m, 2H); 5.82 (t, J = 10 Hz, 1H); 4.72-4.60 (m, 3H); 4.04-3.89 (m, 2H); 3.43-3.32 (m, 2H); 1.56-1.55 (d, J = 5 Hz, 3H); 1.28 (t, J = 10 Hz, 3H). |
| 88 (Isomer D) | 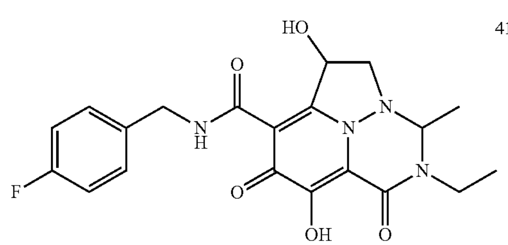 | 417.20 | (500 MHz, CDCl$_3$): δ 11.10 (s, 1H); 7.34-7.31 (m, 2H); 7.04-7.00 (m, 2H); 5.80 (t, J = 10 Hz, 1H); 4.72-4.57 (m, 3H); 4.03-3.95 (m, 1H); 3.78-3.73 (m, 1H); 3.53-3.49 (m,1H); 3.35-3.28 (m, 1H); 1.51-1.50 (d, J = 5 Hz, 3H); 1.30 (t, J = 10 Hz, 3H). |

Example 22

Preparation of Compounds 89-92

Starting from compound Int-16b, using essentially the same method described in Step C and Step D in Example 16 with the exception of 1) substituting 2,4,6-trifluorobenzylamine with 2,4-difluorobenzylamine, 2) isolating the stereoisomers of the product in Step C by 1) chiral preparative SFC (ChiralPak AS-H, 21×250 mm column; 70 g/min; 120 bar; 50% EtOH/$CO_2$) to afford a mixture of isomers A (the 1$^{st}$ eluting component)/isomer B (the 2$^{nd}$ eluting component), isomer C (the 3$^{rd}$ eluting component) and isomer D (the 4$^{th}$ eluting component), and further purifying the mixture of isomer A and B by chiral preparative SFC (ChiralPak OJ-H, 21×250 mm column; 50 g/min; 120 bar; 25% MeOH/$CO_2$) to afford pure isomer A and isomer B, the following compounds were prepared:

| Compound # | Structure | MS (M + H)$^+$ | $^1$H NMR |
|---|---|---|---|
| 89 (Isomer A) | 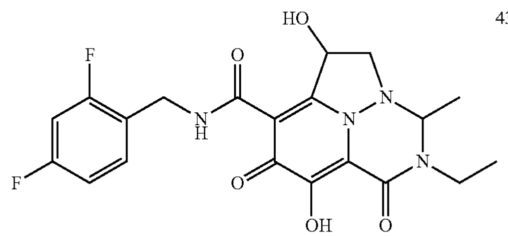 | 435.24 | (500 MHz, $CDCl_3$): δ 11.21 (s, 1H); 7.45-7.33 (m, 1H); 6.93-6.76 (m, 2H); 5.79 (t, J = 7.7 Hz, 1H); 4.74 (q, J = 5.9 Hz, 1H); 4.72-4.58 (m, 2H); 4.00 (dq, J = 14.6, 7.3 Hz, 1H); 3.94 (t, J = 8.8 Hz, 1H); 3.42 (dq, J = 14.1, 7.0 Hz, 1H); 3.37-3.26 (m, 1H); 1.58 (d, J = 6.0 Hz, 3H); 1.30 (t, J = 7.2 Hz, 3H) |
| 90 (Isomer B) | 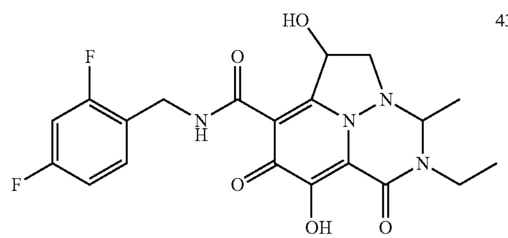 | 435.24 | (400 MHz, $CDCl_3$): δ 11.01 (s, 1H); 7.46-7.29 (m, 1H); 6.82 (m, 2H); 5.76 (dd, J = 7.7, 4.8 Hz, 1H); 4.74 (q, J = 6.0 Hz, 1H); 4.61 (dq, J = 15.3, 7.6, 5.6 Hz, 2H); 3.97 (dq, J = 14.5, 7.2 Hz, 1H); 3.73 (t, J = 9.1 Hz, 1H); 3.51 (dd, J = 10.2, 4.5 Hz, 1H); 3.31 (dq, J = 14.2, 7.1 Hz, 1H); 1.50 (d, J = 6.1 Hz, 3H); 1.28 (t, J = 7.2 Hz, 3H). |
| 91 (Isomer C) | 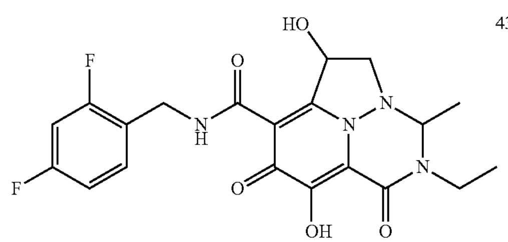 | 435.24 | (500 MHz, $CDCl_3$): δ 11.21 (s, 1H); 7.45-7.33 (m, 1H); 6.93-6.76 (m, 2H); 5.79 (t, J = 7.7 Hz, 1H); 4.74 (q, J = 5.9 Hz, 1H); 4.72-4.58 (m, 2H); 4.00 (dq, J = 14.6, 7.3 Hz, 1H); 3.94 (t, J = 8.8 Hz, 1H); 3.42 (dq, J = 14.1, 7.0 Hz, 1H); 3.37-3.26 (m, 1H); 1.58 (d, J = 6.0 Hz, 3H); 1.30 (t, J = 7.2 Hz, 3H). |
| 92 (Isomer D) | 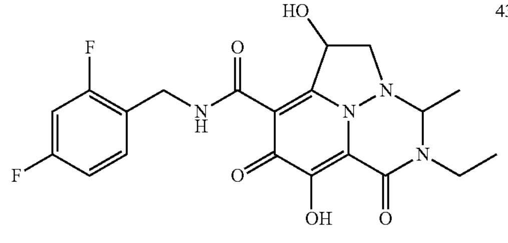 | 435.24 | (400 MHz, $CDCl_3$): δ 11.01 (s, 1H); 7.46-7.29 (m, 1H); 6.82 (m, 2H); 5.76 (dd, J = 7.7, 4.8 Hz, 1H); 4.74 (q, J = 6.0 Hz, 1H); 4.61 (dq, J = 15.3, 7.6, 5.6 Hz, 2H); 3.97 (dq, J = 14.5, 7.2 Hz, 1H); 3.73 (t, J = 9.1 Hz, 1H); 3.51 (dd, J = 10.2, 4.5 Hz, 1H); 3.31 (dq, J = 14.2, 7.1 Hz, 1H); 1.50 (d, J = 6.1 Hz, 3H); 1.28 (t, J = 7.2 Hz, 3H). |

Example 23

Preparation of Compounds 93-96

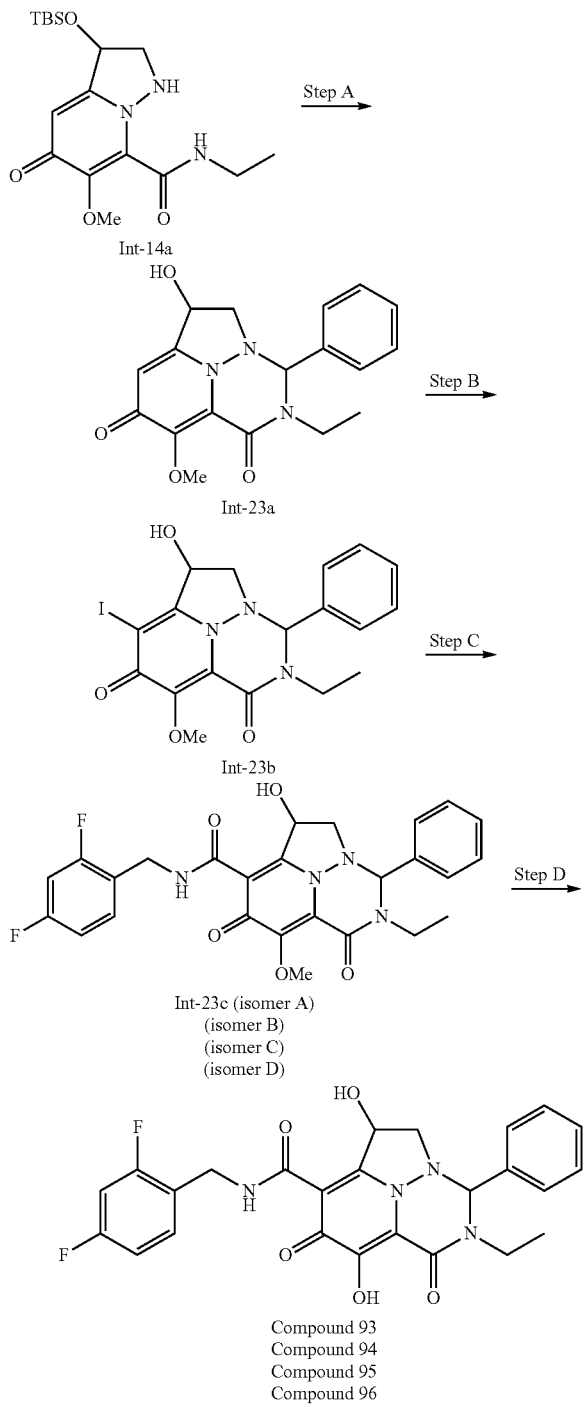

Step A—Synthesis of Compound Int-23a

To a solution of compound int-14a (50 mg, 0.136 mmol) in DCE (1.4 mL) was added benzaldehyde (0.083 mL, 0.816 mmol) and methanesulfonic acid (0.053 mL, 0.816 mmol). The mixture was stirred at 90° C. for 1 h. The mixture was concentrated under reduced pressure and purified with reverse phase HPLC (Waters Sunfire C18 OBD, 10 μm, 30×150 mm column) eluting with 10-90% ACN+0.05% TFA/water+0.05% TFA to afford the crude compound Int-23a. LCMS anal. calcd. for $C_{18}H_{19}N_3O_4$: 341.36; Found: 342.22 (M+1)$^+$.

Step B—Synthesis of Compound Int-23b

NIS (151 mg, 0.670 mmol) and mCPBA (98 mg, 0.436 mmol) were added to a stirred solution of compound int-23a (114 mg, 0.335 mmol) in MeOH (3.4 mL) at room temperature. The reaction mixture was heated to 90° C. for 1 h before being cooled to room temperature and evaporated under reduced pressure. The resulting solid was purified with reverse phase HPLC (Waters Sunfire C18 OBD, 10 μm, 30×150 mm column) eluting with 10-90% ACN+0.05% TFA/water+0.05% TFA to afford compound int-23b. LCMS anal. calcd. for $C_{18}H_{18}IN_3O_4$: 467.23; Found: 468.16 (M+1)$^+$.

Step C—Synthesis of Compound Int-23c

Tetrakis(triphenylphosphine)palladium(0) (30 mg, 0.026 mmol), N,N-diisopropylethylamine (91 μl, 0.522 mmol) and 2,4-difluorobenzylamine (37 mg, 0.261 mmol) were added to a stirred solution of compound int-23b (61 mg, 0.131 mmol) in DMSO (3 mL). The reaction mixture was purged with nitrogen (3×). Carbon monoxide balloon was attached and carbon monoxide gas was bubbled through a long needle to the mixture for 10 min. The reaction mixture was then stirred at 90° C. for 1 hour before being cooled to room temperature. The resulting mixture was filtered (0.45 μm syringe filter), the filter cake was rinsed with 1 mL of MeOH. The combined filtrate was purified by reverse phase HPLC (Waters Sunfire C18 OBD, 10 μm, 30×150 mm column) eluting with 10-90% ACN+0.05% TFA/water+0.05% TFA. Product containing fractions were combined, frozen, and lyophilized to give compound int-23c as a mixture of stereoisomers. To isolate each stereoisomer of the product, this material was further resolved by chiral preparative SFC (ChiralPak OJ-H, 21×250 mm column; 50 g/min, 120 bar; 25% (IPA+0.2% DIPA)/CO$_2$; 40° C.) to afford a mixture of isomers A (the 1$^{st}$ eluting component)/isomer B (the 2$^{nd}$ eluting component), isomer C (the 3$^{rd}$ eluting component) with impurities and isomer D (the 4$^{th}$ eluting component). Further purifying the mixture of isomer A and B by chiral preparative SFC (ChiralPak AS-H, 21×250 mm column; 50 mL/min; 120 bar; 60% MeOH/CO$_2$) to afford isomer A and isomer B with sufficient purity. Further purifying isomer C by chiral preparative SFC (ChiralPak OJ-H, 21×250 mm column; 70 g/min; 120 bar; 25% (IPA+0.2% DIPA)/CO$_2$; 40° C.) to afford pure isomer C. LCMS anal. calcd. for $C_{26}H_{24}F_2N_4O_5$: 510.49; Found: 511.28 (M+1)$^+$.

Step D—Synthesis of Compound 93-96

Isomer D of compound int-23c (16 mg, 0.031 mmol), magnesium bromide (58 mg, 0.313 mmol), and acetonitrile (1 mL) were combined and stirred at room temperature. After 30 minutes, the reaction mixture was diluted with 1 mL of MeOH and filtered (0.45 μm syringe filter) before being purified by reverse phase HPLC (Waters Sunfire C18 OBD, 10 μm, 30×150 mm column) eluting with 10-90% ACN+0.05% TFA/water+0.05% TFA. Product containing fractions were combined and concentrated under reduced pressure until most of the ACN had been removed. The remaining aqueous solution was extracted with DCM (3×~5 mL). The combined organic layer was sequentially dried over Na$_2$SO$_4$, filtered, and evaporated under reduced pressure. The resulting residue was dissolved in ACN (~5 mL), diluted with water (~5 mL), frozen, and lyophilized to afford compound 93. $^1$H NMR (500 MHz, CD$_3$OD) δ 7.65 (d, J=6.6 Hz, 2H); 7.59 (t, J=7.2 Hz, 3H); 7.46 (q, J=7.6 Hz, 1H); 6.95 (q, J=9.9, 9.4 Hz, 2H); 5.81 (m, 1H); 5.71 (s, 1H); 4.62 (s, 2H); 3.64 (dq, J=13.7, 6.8 Hz, 1H); 3.29 (s, 1H); 3.12-2.94 (m, 2H); 1.03 (t, J=6.9 Hz, 3H). LCMS anal. calcd. for $C_{25}H_{22}F_2N_4O_5$: 496.47; Found: 497.22 (M+1)$^+$.

Following essentially the method employed to produce compound 93 in Step D of Example 23, compound 94 was prepared from isomer C of compound int-23c. $^1$H NMR (500 MHz, CD$_3$OD) δ 11.23 (s, 1H); 7.65 (m, 5H); 7.44 (d, J=5.0 Hz, 1H); 6.93 (q, J=9.9, 9.4 Hz, 2H); 5.80 (m, 1H); 5.61 (s, 1H); 4.62 (d, J=11.0 Hz, 2H); 3.67 (dd, J=13.5, 6.5 Hz, 1H); 3.36 (s, 1H); 3.11 (s, 1H); 3.02 (d, J=6.3 Hz, 1H); 1.03 (t, J=6.9 Hz, 3H). LCMS anal. calcd. for $C_{25}H_{22}F_2N_4O_5$: 496.47; Found: 497.26 (M+1)$^+$.

Following essentially the method employed to produce compound 93 in Step D of Example 23, compound 95 was prepared from isomer B of compound int-23c. $^1$H NMR (500 MHz, CD$_3$OD) δ 7.65 (d, J=6.6 Hz, 2H); 7.59 (t, J=7.2 Hz, 3H); 7.46 (q, J=7.6 Hz, 1H); 6.95 (q, J=9.9, 9.4 Hz, 2H); 5.81 (m, 1H); 5.71 (s, 1H); 4.62 (m, 2H); 3.64 (dq, J=13.7, 6.8 Hz, 1H); 3.29 (s, 1H); 3.12-2.94 (m, 2H); 1.03 (t, J=6.9 Hz, 3H). LCMS anal. calcd. for $C_{25}H_{22}F_2N_4O_5$: 496.47; Found: 497.27 (M+1)$^+$.

Following essentially the method employed to produce compound 93 in Step D of Example 23, compound 96 was prepared from isomer A of compound int-23c. $^1$H NMR (500 MHz, CD$_3$OD) δ 11.23 (s, 1H); 7.65 (m, 5H); 7.44 (d, J=5.0 Hz, 1H); 6.93 (q, J=9.9, 9.4 Hz, 2H); 5.80 (m, 1H); 5.61 (s, 1H); 4.62 (d, J=11.0 Hz, 2H); 3.67 (dd, J=13.5, 6.5 Hz, 1H); 3.36 (s, 1H); 3.11 (s, 1H); 3.02 (d, J=6.3 Hz, 1H); 1.03 (t, J=6.9 Hz, 3H). LCMS anal. calcd. for $C_{25}H_{22}F_2N_4O_5$: 496.47; Found: 497.27 (M+1)$^+$.

Example 24

Preparation of Compounds 99-100

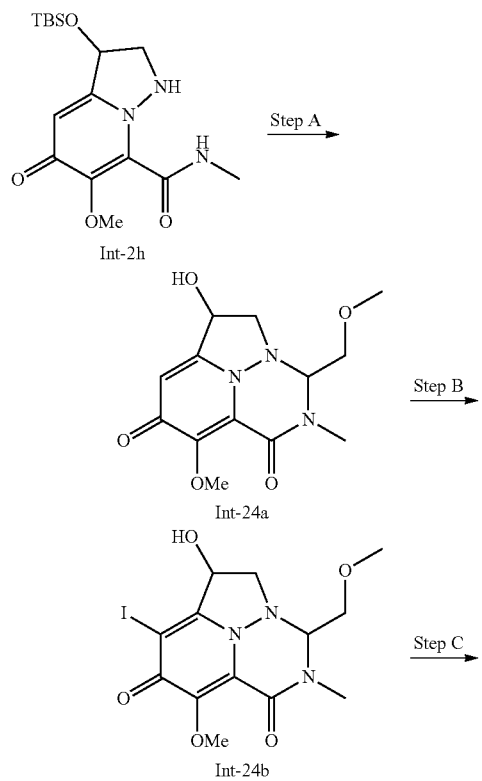

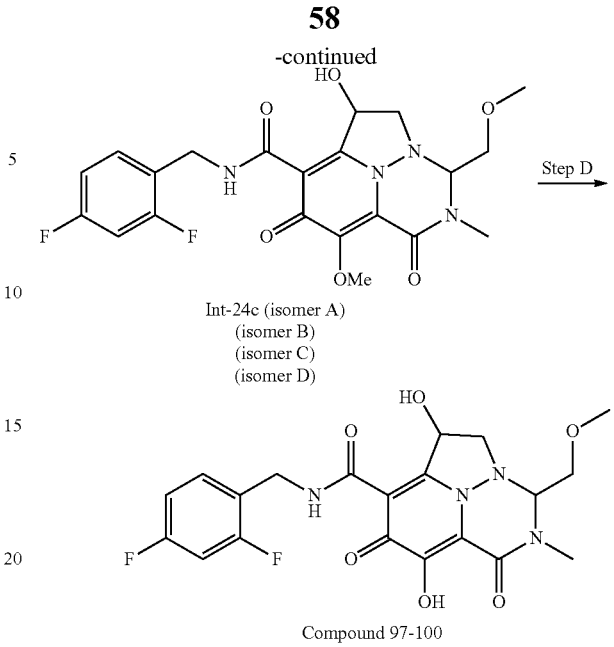

Compound 97-100

Step A—Synthesis of Compound Int-24a

A mixture of p-toluenesulfonic acid monohydrate (1388 mg, 7.30 mmol) and 1,1,2-trimethoxyethane (1462 mg, 12.16 mmol) (0.2 mL) in DCE (3.5 mL) was stirred at room temperature for 5 min. To the mixture was added compound int-2h (430 mg, 1.216 mmol). The resulting mixture was stirred at 90° C. for 4 h. The solvent was removed under vacuum, and the residue was purified by reverse phase HPLC (C18 aq. reverse phase 150 g column; 2 min, 100% water+0.05% TFA; 26 min, 0-50% CH$_3$CN+0.05% TFA/water+0.05% TFA; 5 min, 100% CH$_3$CN+0.05% TFA; 5 min, 50% CH$_3$CN+0.05% TFA/water+0.05% TFA) to afford compound int-24a. LC/MS (m/z): 296.1 (M+H)$^+$.

Step B—Synthesis of Compound Int-24b

To a solution of compound int-24a (290 mg, 0.982 mmol) in MeOH (5 mL) was added NIS (442 mg, 1.964 mmol) and mCPBA (220 mg, 1.277 mmol). The mixture was stirred at 60° C. for 30 min. The solvent was removed under vacuum, and the residue was purified by reverse phase HPLC(C18 aq. 150 g column; 2 min, 100% water+0.05% TFA; 26 min, 0-50% CH$_3$CN+0.05% TFA/water+0.05% TFA; 5 min, 100% CH$_3$CN+0.05% TFA; 5 min 50% CH$_3$CN+0.05% TFA/water+0.05% TFA) to afford compound int-24b. LC/MS (m/z): 421.9 (M+H)$^+$.

Step C—Synthesis of Compound Int-24c

A mixture of compound int-24b (150 mg, 0.356 mmol), Pd(PPh$_3$)$_4$ (123 mg, 0.107 mmol), N,N-diethylpropan-2-amine (0.221 mL, 1.425 mmol) and (2,4-difluorophenyl)methanamine (102 mg, 0.712 mmol) in DMSO (4 mL) was stirred at 80° C. for 1 hour under a CO balloon. The resulting mixture was filtered and the filtrate was purified by reverse phase HPLC (C18 reverse phase 150 g column; 10-90% CH$_3$CN+0.05% TFA/water+0.05% TFA). The product containing fractions were combined and concentrated under vacuum. The residue was further purified by silica gel chromatography (40 g red flash column; 0-100% EtOAC with EtOH (3:1)/hexanes) to afford compound int-24c as a mixture of stereoisomers. LC/MS (m/z): 465.2 (M+H)$^+$. This material was further purified by chiral preparative SFC (DAICEL CHIRALPAK OJ-H, 21×250 mm column; 50 g/min; 15% EtOH/CO$_2$; 210 nm) to afford stereoisomer A of compound int-24c (1$^{st}$ eluting component), isomer B of compound int-24c ($2^{nd}$ eluting component), and a mixture of stereoisomer C and D of compound int-24c ($3^{rd}$ eluting component). The mixture of isomer C and D of compound int-24c was further purified by preparative chiral SFC (OJ-H, 21×250 mm column; 50 g/min; 40% EtOH/CO$_2$; 210 nm) to afford sufficient pure isomer C of compound int-24c ($1^{st}$ eluting component) and isomer D of compound int-24c ($2^{nd}$ eluting component).

Step D—Synthesis of Compound 97-100

To a solution of stereoisomer A of compound int-24c (10 mg, 0.022 mmol) in CH$_3$CN (0.6 mL) was added MgBr$_2$ (31.7 mg, 0.172 mmol). The mixture was stirred at 40° C. for 30 min. The mixture was filtered and the filtrate was purified by reverse phase HPLC (Waters Sunfire C18 OBD, 10 μm, 30×150 mm column), eluting with 30-90% CH$_3$CN+0.05% TFA/water+0.05% TFA. The product containing fractions were collected and concentrated under vacuum to remove CH$_3$CN. The remaining aqeuous mixture was extracted with DCM (~ 8 mL×3). The combined organic layer was concentrated under vacuum. The residue was dissolved into CH$_3$CN and water, and lyophilzed to afford compound 97.
$^1$H NMR (CDCl$_3$, 400 MHz) δ: 11.24 (s, 1H); 7.36 (m, 1H); 6.82 (m, 2H); 5.76 (m, 1H); 4.64 (m, 3H); 3.94 (m, 1H); 3.75 (m, 3H); 3.32 (s, 3H); 3.22 (s, 3H). LC/MS (m/z): 451.2 (M+H)$^+$.

Following essentially the method employed to produce compound 97 in step D of Example 24, compound 98 was prepared from isomer B of compound int-24c. $^1$H NMR (400 MHz, CDCl$_3$) δ: 11.15 (s, 1H); 7.35 (m, 1H); 6.82 (m, 2H); 5.85 (m, 1H); 4.63 (m, 3H); 4.04 (m, 1H); 3.74 (m, 2H); 3.51 (m, 1H); 3.39 (s, 3H); 3.23 (s, 3H). LC/MS (m/z): 451.2 (M+H)$^+$.

Following essentially the method employed to produce compound 97 in step D of Example 24, compound 99 was prepared from isomer C of compound int-24c. $^1$H NMR (400 MHz, CDCl$_3$) δ: 11.09 (s, 1H); 7.36 (m, 1H); 6.83 (m, 2H); 5.90 (m, 1H); 4.65 (m, 3H); 4.01 (m, 1H); 3.76 (m, 2H); 3.56 (m, 1H); 3.37 (s, 3H); 3.23 (s, 3H). LC/MS (m/z): 451.2 (M+H)$^+$.

Following essentially the method employed to produce compound 97 in step D of Example 24, compound 100 was prepared from isomer D of compound int-24c. $^1$H NMR (400 MHz, CDCl$_3$) δ: 11.19 (s, 1H); 7.36 (m, 1H); 6.82 (m, 2H); 5.78 (m, 1H); 4.64 (m, 3H); 3.96 (m, 1H); 3.74 (m, 3H); 3.32 (s, 3H); 3.23 (s, 3H). LC/MS (m/z): 451.2 (M+H)$^+$.

Example 25

Preparation of Compounds 101-102

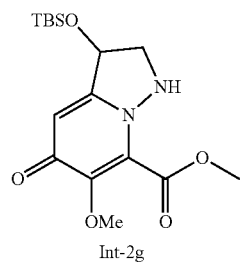
Int-2g

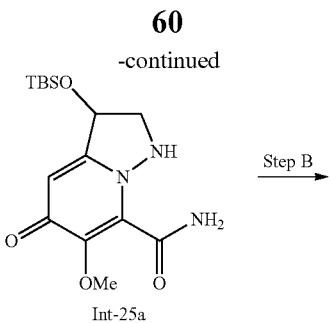
Int-25a

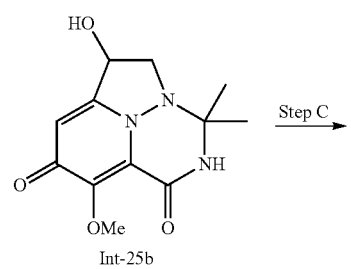
Int-25b

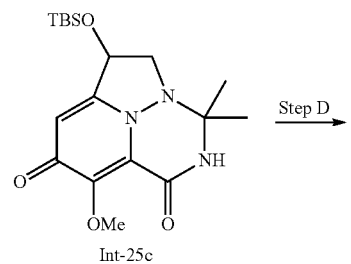
Int-25c

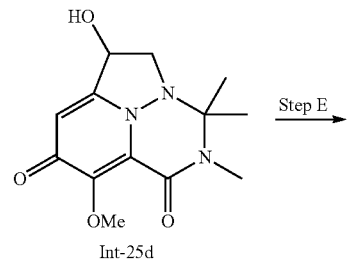
Int-25d

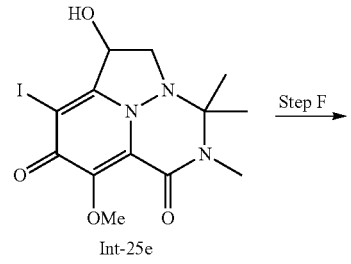
Int-25e

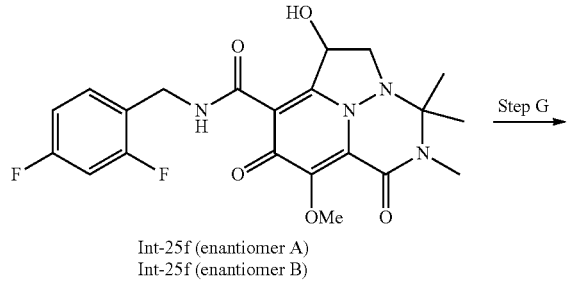
Int-25f (enantiomer A)
Int-25f (enantiomer B)

-continued

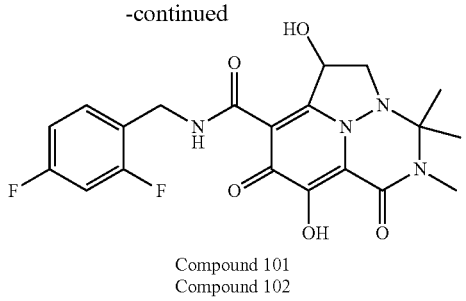

Compound 101
Compound 102

Step A—Synthesis of Compound Int-25a

To a mixture of compound int-2g (150 mg, 0.423 mmol) in MeOH (2 mL) was added a solution of 7 N ammonia in MeOH (0.605 mL, 4.23 mmol) at 25° C. The mixture was stirred at 25° C. for 10 h under a balloon of $N_2$. The solvent was removed in vacuo. The residue was purified by silica gel column chromatography (ISCO®, 12 g Agela Flash Column; 0-10% MeOH/EtOAc, gradient) to give compound int-25a. $^1$H NMR (400 MHz, $CDCl_3$) δ: 7.33 (br.s, 2H); 6.43 (s, 1H); 5.84 (t, J=6.4 Hz, 1H); 3.93 (s, 3H); 3.44-3.49 (m, 1H); 3.15-3.22 (m, 1H); 0.75 (s, 9H); 0.09 (s, 6H). MS (ESI) m/z: 340.0 $[M+H]^+$.

Step B—Synthesis of Compound Int-25b

To a mixture of compound int-25a (100 mg, 0.295 mmol) in DCE (2 mL) was added propan-2-one (342 mg, 5.89 mmol) and methanesulfonic acid (170 mg, 1.768 mmol) at 25° C. The mixture was stirred at 90° C. for 2 h. The solvent was removed in vacuo, and the residue was purified by a preparative silica gel TLC plate eluting with 10% MeOH/DCM to give compound int-25b. MS (ESI) m/z: 266.0 $[M+H]^+$.

Step C—Synthesis of Compound Int-25c

To a mixture of compound int-25b (60 mg, 0.226 mmol) in DMF (3 mL) was added imidazole (46.2 mg, 0.679 mmol) and TBSCl (68.2 mg, 0.452 mmol) at 25° C. The reaction was stirred at 25° C. for 2 h. The reaction was quenched with 8 mL of water, the resulting mixture was extracted with EtOAc (10 mL×3). The combined organic phase was dried over anhydrous $Na_2SO_4$, filtered and concentrated in vacuo. The residue was purified by a preparative silica gel TLC plate eluting with 10% MeOH/DCM to give compound int-25c. MS (ESI) m/z: 380.0 $[M+H]^+$.

Step D—Synthesis of Compound Int-25d

To a mixture of compound int-25c (120 mg, 0.316 mmol) in DMF (10 mL) was added iodomethane (0.040 mL, 0.632 mmol) and sodium hydride (18.97 mg, 0.474 mmol) at 0° C. The reaction was warmed to room temperature (25° C.) and stirred for 1 h. To the resulting mixture was added 1 M HCl (1.5 mL). It was stirred at room temperature for another 15 min. The solvent was removed in vacuo, the residue was diluted with DCM (5 mL) and filtered. The filtrate was concentrated under vacuum and the residue was purified by silica gel column chromatography (ISCO®, 12 g Agela Flash Column; 0-30% MeOH/EtOAc, gradient) to give compound int-25d. $^1$H NMR (400 Mz, $CD_3OD$) δ: 7.33 (br.s, 2H); 5.66 (br s, 1H); 3.93-4.14 (m, 4H); 3.44-3.49 (m, 1H); 3.29 (s, 3H); 1.44 (s, 6H). MS (ESI) m/z: 280.0 $[M+H]^+$.

Step E—Synthesis of Compound Int-25e

To a mixture of compound int-25d (30 mg, 0.107 mmol) in MeOH (2 mL) was added NIS (48.3 mg, 0.215 mmol) and m-CPBA (18.54 mg, 0.107 mmol) at 25° C. The reaction was stirred at 70° C. for 1 h. The mixture was quenched with aqueous $Na_2SO_3$ (0.5 mL) and concentrated in vacuo. The residue was purified by silica gel column chromatography (ISCO®, 4 g Agela Flash Colum; 0-10% MeOH/DCM, gradient) to give compound int-25e. $^1$H NMR (400 Mz, $CD_3OD$) δ: 5.38-5.42 (m, 1H); 5.38-5.42 (m, 1H); 3.91 (s, 3H); 3.86 (s, 1H); 3.64 (d, J=2.9 Hz, 1H); 3.13 (s, 3H); 1.57 (s, 3H); 1.34 (s, 3H). MS (ESI) m/z: 405.8 $[M+H]^+$.

Step F—Synthesis of Compound Int-25f

To a solution of compound int-25e (20 mg, 0.049 mmol) in DMSO (2 mL) was added N-ethyl-N-isopropylpropan-2-amine (19.14 mg, 0.148 mmol), (2,4-difluorophenyl)methanamine (14.13 mg, 0.099 mmol) and $Pd(PPh_3)_4$ (11.41 mg, 9.87 µmol) at 25° C. The mixture was degassed 3 times. The resulting solution was stirred at 80° C. for 1 h under a balloon of CO. Water (10 mL) was added and the resulting mixture was extracted with EtOAc (15 mL×3). The combined organic phase was dried over anhydrous $Na_2SO_4$, filtered and concentrated in vacuo. The residue was purified by a preparative silica gel TLC plate eluting with 5% MeOH/DCM to give compound int-25f. $^1$H NMR (400 Mz, $CD_3OD$) δ: 5.38-5.42 (m, 1H); 5.38-5.42 (m, 1H); 3.91 (s, 3H); 3.86 (s, 1H); 3.64 (d, J=2.9 Hz, 1H); 3.13 (s, 3H); 1.57 (s, 3H); 1.34 (s, 3H). MS (ESI) m/z: 405.8 $[M+H]^+$. The enantiomers of compound int-25f were resolved by preparative SFC (Column: DAICEL CHIRALCEL OJ-H, 250 mm×30 mm, 5 µm column; Mobile phase: 20% MeOH+ 0.10% $NH_3H_2O/CO_2$; FlowRate: 60 mL/min) to give enantiomer A of compound int-25f ($1^{st}$ eluting isomers), and enantiomer B of compound int-25f ($2^{nd}$ eluting isomers). MS (ESI) m/z: 405.8 $[M+H]^+$.

Step G—Synthesis of Compound 101 and Compound 102

To a mixture of enantiomer A of compound int-25f (8 mg, 0.018 mmol) in MeCN (2 mL), magnesium bromide (16.42 mg, 0.089 mmol) was added at 25° C. The reaction was stirred at 25° C. for 3 h. It was quenched with MeOH (0.5 mL) and the resulting mixture was filtered. The filtrate was purified by reverse phase HPLC (Column Boston Green ODS 150×30 mm, 5 µm column; Condition: 30-60% MeCN/water+0.1% TFA; Gradient Time: 10 min; FlowRate: 25 mL/min). The product containing fractions were combined and lyophilized, and the residue was co-evaporated with toluene (10 mL) twice to remove residual TFA and give compound 101. $^1$H NMR (400 MHz, $CDCl_3$) δ: 11.24 (br s, 1H); 7.30-7.44 (m, 1H); 6.71-6.90 (m, 2H); 5.78 (br t, J=7.5 Hz, 1H); 4.65 (br d, J=4.9 Hz, 2H); 3.87 (br t, J=9.2 Hz, 1H); 3.35-3.47 (m, 1H); 3.06-3.21 (m, 3H); 1.53 (s, 3H); 1.46 (s, 3H). MS (ESI) m/z: 435.0 $[M+H]^+$.

Following essentially the method employed to produce compound 101 in Step G of Example 25, compound 102 was prepared from isomer B of compound int-25f. $^1$H NMR (400 MHz, $CDCl_3$) δ: 11.25 (br s, 1H); 7.30-7.44 (m, 1H); 6.72-6.94 (m, 2H); 5.68-5.87 (m, 1H); 4.65 (br d, J=6.4 Hz, 2H); 3.87 (br t, J=9.5 Hz, 1H); 3.34-3.49 (m, 1H); 3.14 (s, 3H); 1.55 (s, 3H); 1.45 (s, 3H). MS (ESI) m/z: 435.0 $[M+H]^+$.

Example 26

Preparation of Compounds 103-106

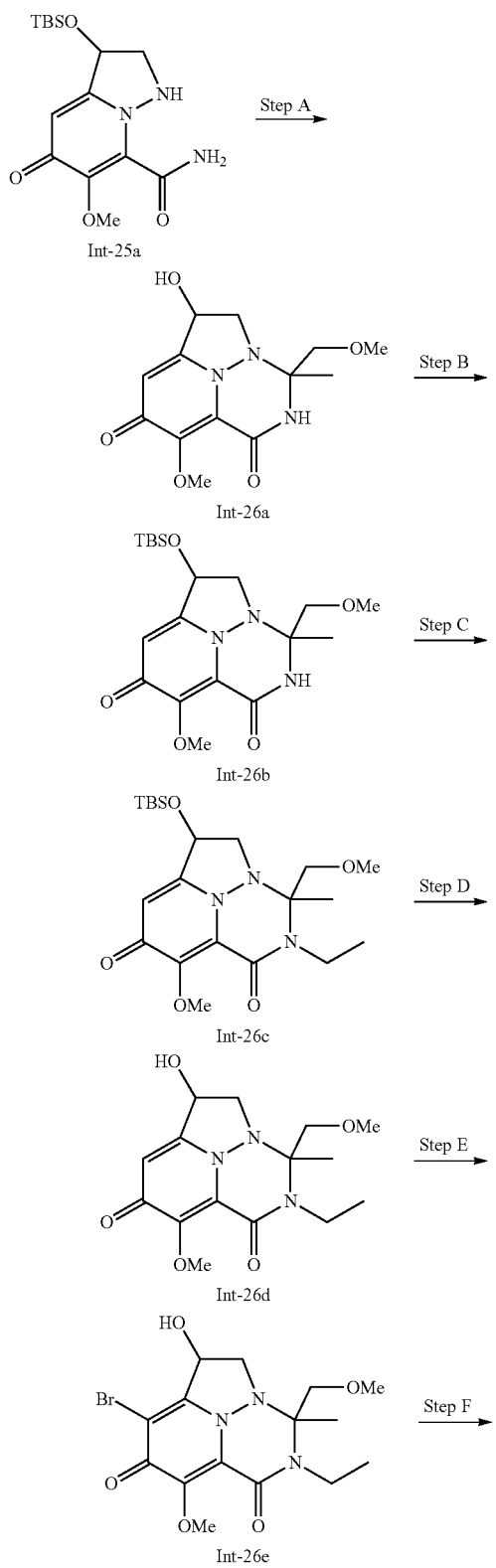

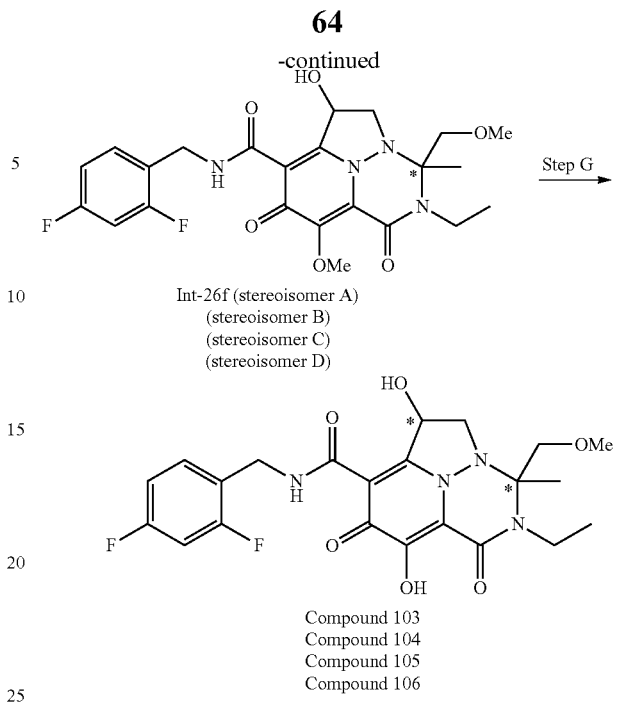

Int-26f (stereoisomer A)
(stereoisomer B)
(stereoisomer C)
(stereoisomer D)

Compound 103
Compound 104
Compound 105
Compound 106

Step A—Synthesis of Compound Int-26a

To a mixture of compound int-25a (800 mg, 2.357 mmol) in DCE (10 mL) was added 1-methoxypropan-2-one (4153 mg, 47.1 mmol) and methanesulfonic acid (1359 mg, 14.14 mmol) at 25° C. The reaction was stirred at 90° C. for 2 h. The resulting mixture was concentrated in vacuo, the residue was purified by reverse phase HPLC (column: Phenomenex Synergi C18 150 mm×30 mm×5 μm; condition: 0-26% MeCN/water+0.1% TFA; gradient time: 10 min; FlowRate: 25 mL/min) to give compound int-26a. MS (ESI) m/z: 296.1 [M+H]$^+$.

Step B—Synthesis of Compound Int-26b

To a mixture of compound int-26a (400 mg, 1.355 mmol) in DMF (3 mL) was added 1H-imidazole (277 mg, 4.06 mmol) and tert-butylchlorodimethylsilane (408 mg, 2.71 mmol) at 25° C. The reaction was stirred at 25° C. for 2 h. The resulting mixture was concentrated in vacuo. The residue was purified by a preparative silica gel TLC plate eluting with 10% MeOH/DCM to compound int-26b. MS (ESI) m/z: 410.2 [M+H]$^+$.

Step C—Synthesis of Compound Int-26c

To a solution of compound int-26b (110 mg, 0.269 mmol) in DMF (2 mL) was added Cs$_2$CO$_3$ (263 mg, 0.806 mmol) and iodoethane (126 mg, 0.806 mmol) at 0° C. The reaction mixture was stirred at 20° C. for 12 h. The solvent was removed under vacuum, the residue was purified by a preparative silica gel TLC plate eluting with 10% MeOH/DCM to give compound int-26c. MS (ESI) m/z: 438.2 [M+H]$^+$.

Step D—Synthesis of Compound Int-26d

To a stirred solution of compound int-26c (110 mg, 0.251 mmol) in THF (1 mL) was added a solution of 1 M TBAF in THF (0.503 mL, 0.503 mmol). The reaction was stirred at 15° C. for 1 h. The solvent was removed under vacuum, the residue was purified by a preparative silica gel TLC plate eluting with 10% MeOH/DCM to give compound int-26d. MS (ESI) m/z: 324.1 [M+H]$^+$.

Step E—Synthesis of Compound Int-26e

To a mixture of compound int-26d (80 mg, 0.247 mmol) in DCM (2 mL) was added NBS (88 mg, 0.495 mmol) at 0°

C. The reaction was stirred at 0° C. for 0.5 h. The reaction mixture was directly purified by by a preparative silica gel TLC plate eluting with 10% MeOH/DCM to give compound int-26e. MS (ESI) m/z: 402.1, 404.1 [M+H]⁺.

Step F—Synthesis of Compound Int-26f

To a solution of compound int-26e (135 mg, 0.336 mmol) in DMSO (3 mL) was added N-ethyl-N-isopropylpropan-2-amine (130 mg, 1.007 mmol), (2,4-difluorophenyl)methanamine (96 mg, 0.671 mmol) and Pd(dppf)Cl$_2$ (123 mg, 0.168 mmol) at 25° C. The resulting mixture was degassed 3 times before it was stirred at 90° C. for 3 h under a balloon of CO. The mixture was filtered and purified by reverse phase HPLC (Boston Green ODS 150 mm×30 mm×5 μm column; 40-60% MeCN/water+0.1% TFA; Gradient Time: 10 min; FlowRate: 25 mL/min) to afford diastereomer 1 of compound int-26f (first eluting isomer) and diastereomer 2 of compound int-26f (second eluting isomer).

Diastereomer 1 of compound int-26f: $^1$H NMR (400 MHz, CDCl$_3$) δ: 11.21 (br s, 1H); 7.33-7.37 (m, 1H); 6.78-6.85 (m, 2H); 5.82 (d, J=4.4 Hz, 1H); 4.61-4.64 (m, 2H); 4.00-4.01 (m, 4H); 3.79-3.83 (m, 1H); 3.44-3.61 (m, 4H); 3.27 (s, 3H); 1.58 (s, 3H); 1.29 (t, J=6.8 Hz, 3H). MS (ESI) m/z: 493.1 [M+H]⁺.

Diastereomer 2 of compound int-26f: $^1$H NMR (400 MHz, CDCl$_3$) δ: 11.40 (br s, 1H); 7.35-7.37 (m, 1H); 6.78-6.85 (m, 2H); 5.72 (t, J=7.2 Hz, 1H); 4.61-4.64 (m, 2H); 4.03 (s, 3H); 3.76-3.96 (m, 3H); 3.55 (s, 2H); 3.43-3.47 (m, 1H); 3.22 (s, 3H); 1.63 (s, 3H); 1.29 (t, J=6.8 Hz, 3H). MS (ESI) m/z: 493.1 [M+H]⁺.

The enantiomers of the diastereomer 1 of compound int-26f were further resolved by SFC (Column: Phenomenex-Amylose-1, 250 mm×30 mm×5 μm; Mobile phase: 40% EtOH+0.1% NH$_3$·H$_2$O)/CO$_2$; Flow rate: 50 mL/min; Wavelength: 220 nm) to afford stereoisomer A of compound int-26f (first eluting isomer), and stereoisomer B of compound int-26f (second eluting isomer).

The enantiomers of the diastereomer 2 of compound int-26f were further resolved by SFC (Column: Phenomenex-Amylose-1, 250 mm×30 mm×5 μm; Mobile phase: 40% EtOH+0.1% NH$_3$·H$_2$O/CO$_2$; Flow rate: 50 mL/min; Wavelength: 220 nm) to afford stereoisomer C of compound int-26f (first eluting isomer), and stereoisomer D of compound int-26f (second eluting isomer).

Step G—Synthesis of Compound 103-106

To a solution of stereoisomer A of compound int-26f (20 mg, 0.041 mmol) in MeCN (3 mL) was added magnesium bromide (37.4 mg, 0.203 mmol). The mixture was stirred at 20° C. for 12 h. The mixture was quenched with MeOH (0.5 mL) and purified by reverse phase HPLC (Boston Green ODS 150 mm×30 mm×5 μm column; Mobile phase: 33-63% MeCN/water+0.1% TFA; Gradient Time: 10 min; FlowRate: 25 mL/min), the product containing fractions were combined and lyophilized. The residue was co-evaporated with toluene 2 times to remove the residual TFA and afford compound 103. $^1$H NMR (400 MHz, CDCl$_3$) δ: 11.14 (br s, 1H); 7.33-7.37 (m, 1H); 6.78-6.85 (m, 2H); 5.85 (dd, J=4.4 Hz, J=8 Hz, 1H); 4.64 (d, J=5.6 Hz, 2H); 3.94-3.99 (m, 1H); 3.80-3.83 (m, 1H); 3.56-3.64 (m, 3H); 3.42-3.48 (m, 1H); 3.32 (s, 3H); 1.57 (s, 3H); 1.31 (t, J=7.6 Hz, 3H). MS (ESI) m/z: 479.2 [M+H]⁺.

Following essentially the method employed to produce compound 103 in Step G of Example 26, compound 104 was prepared from isomer B of compound int-26f. $^1$H NMR (400 MHz, CDCl$_3$) δ: 11.17 (br s, 1H); 7.35-7.37 (m, 1H); 6.78-6.85 (m, 2H); 5.82 (dd, J=4.4 Hz, J=8 Hz, 1H); 4.65 (d, J=6 Hz, 2H); 3.95-3.99 (m, 1H); 3.79-3.84 (m, 1H); 3.56-3.64 (m, 3H); 3.42-3.48 (m, 1H); 3.32 (s, 3H); 1.56 (s, 3H); 1.31 (t, J=7.2 Hz, 3H). MS (ESI) m/z: 479.2 [M+H]⁺.

Following essentially the method employed to produce compound 103 in Step G of Example 26, compound 105 was prepared from isomer C of compound int-26f. $^1$H NMR (400 MHz, CDCl$_3$) δ: 11.35 (br s, 1H); 7.33-7.39 (m, 1H); 6.78-6.89 (m, 2H); 5.70-5.72 (m, 1H); 4.64 (d, J=5.2 Hz, 2H); 3.97-4.01 (m, 1H); 3.84-3.90 (m, 1H); 3.56-3.72 (m, 3H); 3.37-3.44 (m, 1H); 3.24 (s, 3H); 1.64 (s, 3H); 1.30 (t, J=7.6 Hz, 3H). MS (ESI) m/z: 479.2 [M+H]⁺.

Following essentially the method employed to produce compound 103 in Step G of Example 26, compound 106 was prepared from isomer D of compound int-26f. $^1$H NMR (400 MHz, CDCl$_3$) δ: 11.35 (br s, 1H); 7.33-7.39 (m, 1H); 6.78-6.89 (m, 2H); 5.70-5.72 (m, 1H); 4.64 (d, J=5.2 Hz, 2H); 3.97-4.01 (m, 1H); 3.83-3.90 (m, 1H); 3.56-3.72 (m, 3H); 3.37-3.44 (m, 1H); 3.24 (s, 3H); 1.64 (s, 3H); 1.30 (t, J=7.2 Hz, 3H). MS (ESI) m/z: 479.2 [M+H]⁺.

Example 27

Preparation of Compounds 107-110

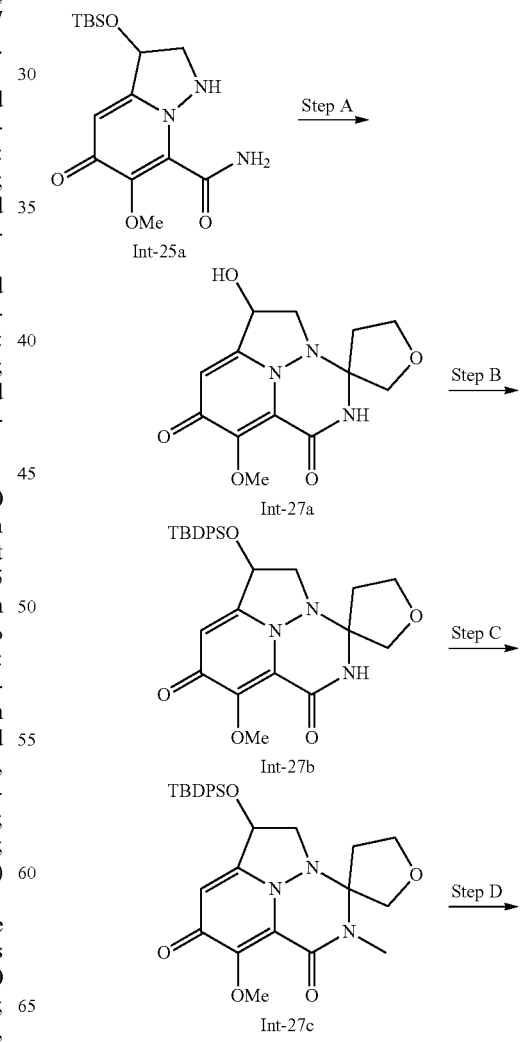

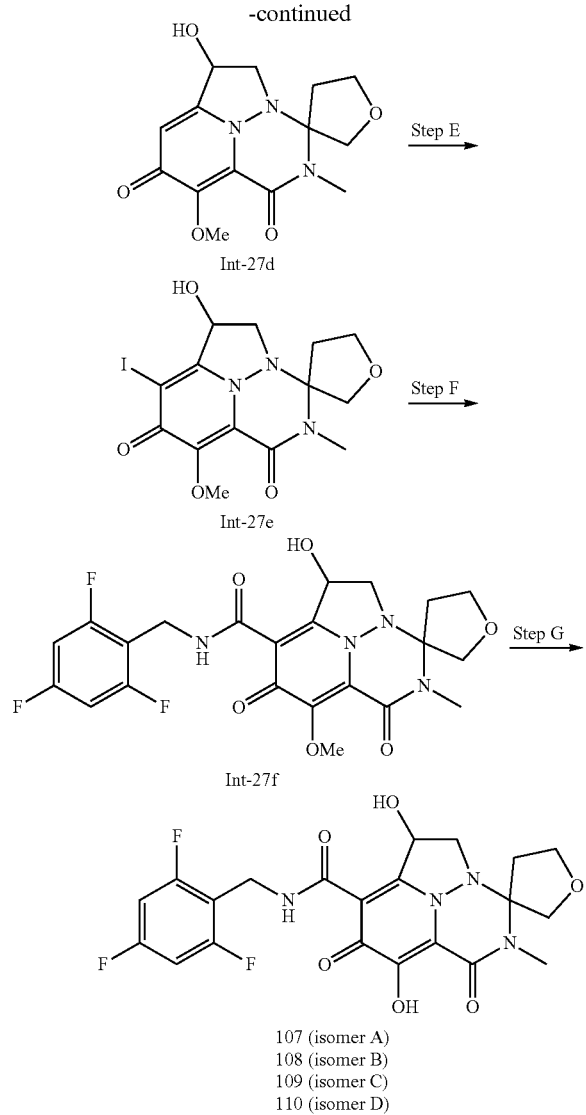

Int-27d

Int-27e

Int-27f 107 (isomer A)
108 (isomer B)
109 (isomer C)
110 (isomer D)

Step A—Synthesis of Compound Int-27a

To a solution of Compound Int-25a (1 g, 2.95 mmol) in DCE (20 mL) was added dihydrofuran-3(2H)-one (2.54 g, 29.5 mmol) and methanesulfonic acid (1.148 mL, 17.68 mmol). The mixture was stirred at 90° ° C. for 1 h. The mixture was concentrated under reduced pressure and purified with ISCO (275 g C18 aqueous reverse phase column, eluting with 0-100% ACN+0.05% TFA/water+0.05% TFA to afford the crude compound Int-27a as an off-white solid. This material was used in the next step without further purification. LCMS anal. calcd. for $C_{13}H_{15}N_3O_5$: 293.27; Found: 294.09 (M+1)$^+$.

Step B—Synthesis of Compound Int-27b

To a slurring of compound Int-27a (850 mg, 2.90 mmol) in DMF (20 mL) were added 1H-imidazole (987 mg, 14.49 mmol) and TBDPSCl (2.261 ml, 8.69 mmol). The mixture was stirred at rt for 2 h. The mixture was diluted with EtOAc, and washed with saturated NH4Cl. The organic phase was dried over anhydrous MgSO4 and concentrated under reduced pressure. The residue was purified with ISCO (80 g column, 10% MeOH in DCM) to afford compound Int-27b. LCMS anal. calcd. for $C_{29}H_{33}N_3O_5Si$: 531.67; Found: 532.36 (M+1)$^+$.

Step C—Synthesis of Compound Int-27c

To a solution of compound Int-27b (935 mg, 1.759 mmol) in DMF (15 mL) was added cesium carbonate (1146 mg, 3.52 mmol) and iodomethane (499 mg, 3.52 mmol). The mixture was stirred at RT for 1 h. The mixture was diluted with EtOAc, and washed with saturated NH4Cl. The organic phase was dried over anhydrous MgSO4 and concentrated under reduced pressure. The residue was purified with ISCO (80 g column, 10% MeOH in DCM) to afford compound Int-27c. LCMS anal. calcd. for $C_{30}H_{35}N_3O_5Si$: 545.70; Found: 546.36 (M+1)$^+$.

Step D—Synthesis of Compound Int-27d

To a solution of compound Int-27c (850 mg, 1.558 mmol) in THF (15 mL) was added tetrabutylammonium fluoride (3.12 mL 1.0 M THF solution, 3.12 mmol). It was stirred at RT for 1 h. The mixture was purified by reverse C18 (275 g aqueous C18 cartridge, eluting with ACN in water, from 0 to 100%) to afford compound Int-27d. LCMS anal. calcd. for $C_{14}H_{17}N_3O_5$: 307.30; Found: 308.18 (M+1)$^+$.

Step E—Synthesis of Compound Int-27e

NIS (688 mg, 3.06 mmol) and mCPBA (396 mg, 2.29 mmol) were added to a stirred solution of compound Int-27d (470 mg, 1.53 mmol) in MeOH (15 mL). The reaction mixture was heated to 70° C. for 1 hour before it was cooled to room temperature and evaporated under reduced pressure. The resulting solid was purified by ISCO (275 g C18 aqueous reverse phase column, eluting with 0-100% ACN+0.05% TFA/water+0.05% TFA) to afford compound Int-27e. LCMS anal. calcd. for $C_{14}H_{16}IN_3O_5$: 433.20; Found: 434.08 (M+1)$^+$.

Step F—Synthesis of Compound Int-27f

To a stirred solution of compound Int-27e (140 mg, 0.323 mmol) in DMSO (3.5 mL), was added Pd(PPh$_3$)$_4$ (75 mg, 0.065 mmol), N,N-diisopropylethylamine (225 µL, 1.293 mmol) and 2,4,6-trifluorobenzylamine (104 mg, 0.646 mmol). The reaction mixture was degassed (3×) and placed placed under a carbon monoxide balloon. It was stirred at 90° C. for 1 hour. After it was cooled to RT, the mixture was filtered (0.45 µm syringe filter), the filtrate was diluted with 1 mL of MeOH, and it was purified by reverse phase HPLC (RediSep Rf C18 100 g column) eluting with 10-100% ACN+0.05% TFA/water+0.05% TFA. Product fractions were combined, frozen, and lyophilized, which was further purified by chiral preparative SFC (ChiralPak OJ-H, 21×250 mm column, 70 g/min, 120 bar, 30% IPA/CO$_2$, 40° C.) to afford isomer A of compound Int-27f (first eluting component), isomer B of compound Int-27f (2nd fastest eluting component), isomer C of compound Int-27f (3$^{rd}$ eluting component), and isomer D of compound Int-27f (4$^{th}$ eluting component). LCMS anal. calcd. for $C_{22}H_{21}F_3N_4O_6$: 494.42; Found: 495.20 (M+1)$^+$.

Step G—Synthesis of Compound Int-107

Isomer A of compound Int-27f (20.0 mg, 0.04 mmol), magnesium bromide (74 mg, 0.4 mmol), and acetonitrile (3 mL) were combined and stirred at room temperature. After 30 minutes, the reaction mixture was diluted with MeOH and filtered (0.45 µm syringe filter) before being purified by reverse phase HPLC (Waters Sunfire C18 OBD, 10 µm, 30×150 mm column) eluting with 10-90% ACN+0.05% TFA/water+0.05% TFA. Product fractions were combined and concentrated under reduced pressure until most of the ACN had been removed. The remaining aqueous mixture was extracted with DCM (~5 mL×3). The organic layers were sequentially dried over Na$_2$SO$_4$, filtered, combined, and evaporated under reduced pressure. The resulting residue was dissolved in ACN (~5 mL), diluted with water (~5 mL), frozen, and lyophilized to afford compound 107. $^1$H NMR (500 MHz, CDCl₃): δ 11.03 (s, 1H), 6.67 (t, J=10 Hz, 2H); 5.83-5.79 (m, 1H); 4.71-4.66 (m, 2H); 4.14-3.90 (m, 5H); 3.55-3.51 (m, 1H); 3.22 (s, 3H); 2.57-2.50 (m, 1H); 2.27-2.22 (m, 1H). LCMS anal. calcd. for $C_{21}H_{19}F_3N_4O_6$: 480.40; Found: 481.20 (M+1)⁺.

Following essentially the method employed to produce compound 107 in step H of example 27, compound 108 was prepared from isomer B of compound Int-27f. ¹H NMR (500 MHz, CDCl₃): δ 11.00 (s, 1H), 6.67 (t, J=10 Hz, 2H); 5.83 (s, 1H); 4.66 (s, 2H); 4.15-3.77 (m, 6H); 3.22 (s, 3H); 2.45-2.37 (m, 2H). LCMS anal. calcd. for $C_{21}H_{19}F_3N_4O_6$: 480.40; Found: 481.20 (M+1)⁺.

Following essentially the method employed to produce compound 107 in step H of example 27, compound 109 was prepared from isomer C of compound Int-27f. ¹H NMR (500 MHz, CDCl₃): δ 11.05 (s, 1H); 6.67 (t, J=10 Hz, 2H); 5.80-5.78 (m, 1H); 4.66 (s, 2H); 4.12-3.89 (m, 5H); 3.54-3.50 (m, 1H); 3.22 (s, 3H); 2.57-2.50 (m, 1H); 2.25-2.21 (m, 1H). LCMS anal. calcd. for $C_{21}H_{19}F_3N_4O_6$: 480.40; Found: 481.20 (M+1)⁺.

Following essentially the method employed to produce compound 107 in step H of example 27, compound 110 was prepared from isomer D of compound Int-27f. ¹H NMR (500 MHz, CDCl₃): δ 10.99 (s, 1H), 6.67 (t, J=10 Hz, 2H); 5.83 (s, 1H); 4.66 (s, 2H); 4.15-3.77 (m, 6H); 3.22 (s, 3H); 2.47-2.33 (m, 2H). LCMS anal. calcd. for $C_{21}H_{19}F_3N_4O_6$: 480.40; Found: 481.21 (M+1)⁺.

Example 28

Preparation of Compounds 111-114

Starting from compound Int-27e, compounds 111-114 were prepared using essentially the same method described in Step F and Step G in example 27 with the exception of substituting 2,4,6-trifluorobenzylamine with 2,4-difluorobenzylamine, and purifying by chiral preparative SFC (ChiralPak OD-H, 21×250 mm column, 60 mL/min, 100 bar, 50% MeOH/CO₂) to afford Isomers A, Isomer B, Isomer C and Isomer D in Step F.

| Compound # | Structure | MS (M + H)⁺ | ¹H NMR |
|---|---|---|---|
| 111 (Isomer A) | 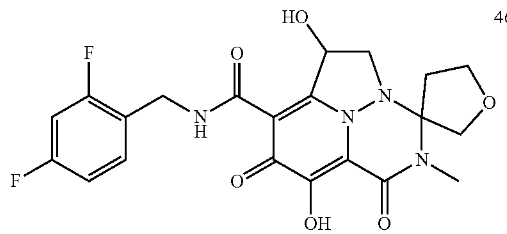 | 463.18 | (500 MHz, CDCl₃): δ 11.07 (s, 1H), 7.38-7.32 (m, 1H); 6.85-6.79 (m, 2H), 5.83-5.79 (m, 1H); 4.65-4.64 (d, J = 5 Hz, 2H); 4.17-3.74 (m, 6H); 3.23 (s, 3H); 2.49-2.34 (m, 2H). |
| 112 (Isomer B) | 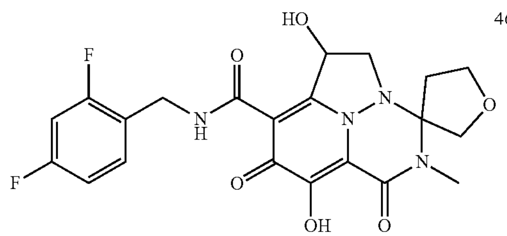 | 463.19 | (500 MHz, CDCl₃): δ 11.06 (s, 1H), 7.38-7.32 (m, 1H); 6.85-6.79 (m, 2H), 5.82 (s, 1H); 4.65-4.64 (d, J = 5 Hz, 2H); 4.16-3.76 (m, 6H); 3.23 (s, 3H); 2.48-2.33 (m, 2H). |
| 113 (Isomer C) | 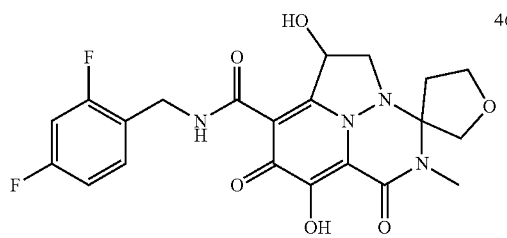 | 463.17 | (500 MHz, CDCl₃): δ 11.09 (s, 1H), 7.38-7.32 (m, 1H); 6.85-6.79 (m, 2H), 5.80 (m, 1H); 4.65-4.64 (d, J = 5 Hz, 2H); 4.15-3.84 (m, 5H); 3.56-3.52 (m, 1H); 3.23 (s, 3H); 2.58-2.51 (m, 1H), 2.28-2.21 (m, 1H). |
| 114 (Isomer D) | 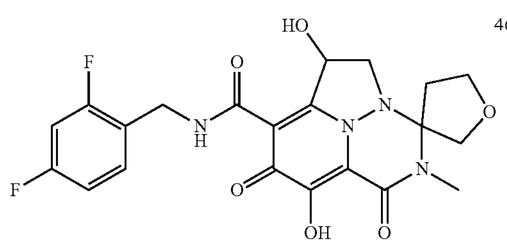 | 463.19 | 500 MHz, CDCl₃): δ 11.09 (s, 1H), 7.38-7.32 (m, 1H); 6.85-6.79 (m, 2H), 5.80 (m, 1H); 4.65-4.64 (d, J = 5 Hz, 2H); 4.15-3.90 (m, 5H); 3.56-3.52 (m, 1H); 3.22 (s, 3H); 2.58-2.51 (m, 1H), 2.28-2.21 (m, 1H) |

Example 29

Preparation of Compounds 115-118

Starting from compound Int-27e, compounds 115-118 were prepared using essentially the same method described in Step F and Step G in example 27 with the exception of substituting 2,3,6-trifluorobenzylamine with 3-chloro-2,6-difluorobenzylamine, and purifying stereoisomers of the product in Step F by chiral preparative SFC under following conditions: 1) ChiralPak OJ-H, 21×250 mm column, 60 m/m, 100 bar, 30C$_8$ MeOH/CO$_2$ to afford fraction 1 containing a mixture of isomer A and B (1$^{st}$ eluting component), and fraction 2 containing a mixture of isomer C and D (2$^{nd}$ eluting component); 2) Fraction 1 was further purified by ChiralPak OJ-H, 21×250 mm column, 65 mL/mH, 100 bar, 20I i-PrOH (0.1% NH$_3$·MeOH)/CO$_2$ to afford isomer A (1$^{St}$ eluting component) and isomer B (2$^{nd}$ eluting component); 3) Fraction 2 was further purified by ChiralPak AS-H, 21×250 mm column, 65 mL/min, 100 bar, 15% MeOH/CO$_2$ to afford isomer C (1$^{st}$ eluting component) and isomer D (2$^{nd}$ eluting component).

| Compound # | Structure | MS (M + H)$^+$ | $^1$H NMR |
|---|---|---|---|
| 115 (Isomer A) | 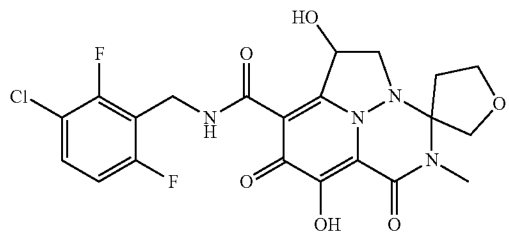 [SMILES: CN1C(=O)c2c(O)c(=O)c(C(=O)NCc3c(F)ccc(Cl)c3F)c3n2N(CC3O)C12CCOC2] | 497.21 | (500 MHz, CDCl$_3$): δ 11.06 (s, 1H), 7.34-7.28 (m, 1H); 6.90-6.75 (m, 1H); 5.83-5.80 (m, 1H); 4.73-4.69 (m, 2H); 4.14-3.90 (m, 5H); 3.56-3.52 (m, 1H); 3.22 (s, 3H); 2.57-2.50 (m, 1H), 2.28-2.21 (m, 1H) |
| 116 (Isomer B) | 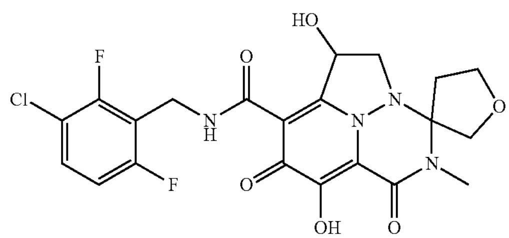 [SMILES: CN1C(=O)c2c(O)c(=O)c(C(=O)NCc3c(F)ccc(Cl)c3F)c3n2N(CC3O)C12CCOC2] | 497.21 | (500 MHz, CDCl$_3$): δ 11.06 (s, 1H), 7.34-7.28 (m, 1H); 6.90-6.85 (m, 1H); 5.82 (s, 1H); 4.73 (s, 2H); 4.15-3.74 (m, 6H); 3.22 (s, 3H); 2.45-2.35 (m, 2H). |
| 117 (Isomer C) | 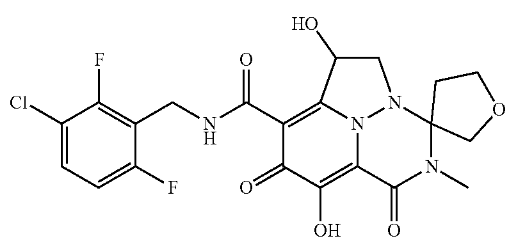 [SMILES: CN1C(=O)c2c(O)c(=O)c(C(=O)NCc3c(F)ccc(Cl)c3F)c3n2N(CC3O)C12CCOC2] | 497.20 | (500 MHz, CDCl$_3$): δ 11.06 (s, 1H), 7.34-7.28 (m, 1H); 6.90-6.85 (m, 1H), 5.83-5.80 (m, 1H); 4.78-4.68 (m, 2H); 4.14-3.90 (m, 5H); 3.56-3.52 (m, 1H); 3.22 (s, 3H); 2.57-2.50 (m, 1H), 2.28-2.21 (m, 1H) |
| 118 (Isomer D) | 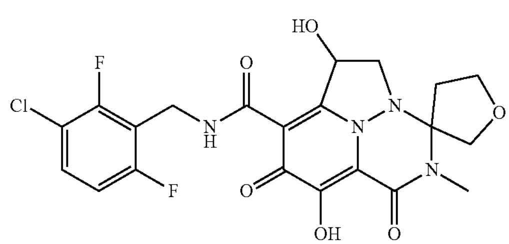 [SMILES: CN1C(=O)c2c(O)c(=O)c(C(=O)NCc3c(F)ccc(Cl)c3F)c3n2N(CC3O)C12CCOC2] | 497.24 | (500 MHz, CDCl$_3$): δ 11.03 (s, 1H), 7.34-7.28 (m, 1H); 6.90-6.85 (m, 1H); 5.83 (s, 1H); 4.78-4.73 (m, 2H); 4.15-3.74 (m, 6H); 3.21 (s, 3H); 2.48-2.33 (m, 2H). |

Example 30

Preparation of Compounds 119-122

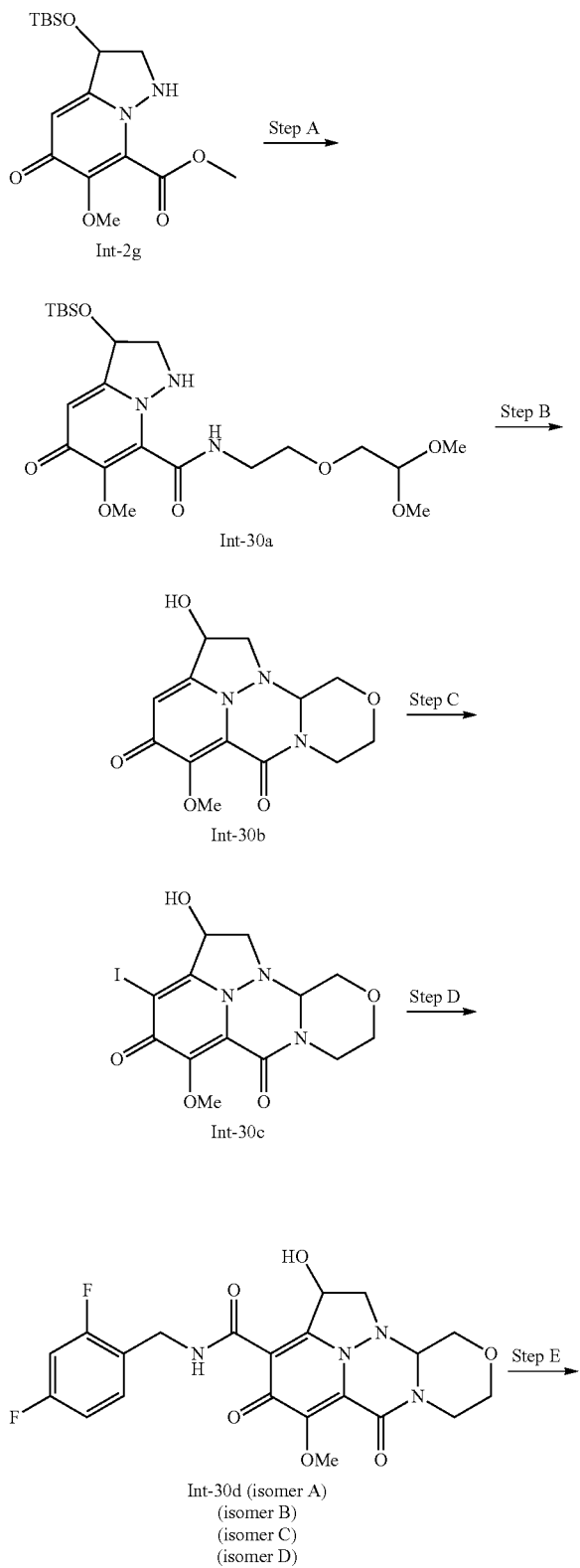

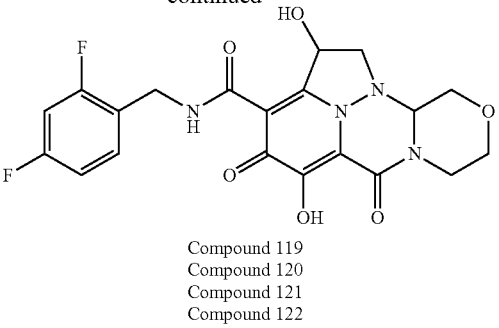

Compound 119
Compound 120
Compound 121
Compound 122

Step A—Synthesis of Compound Int-30a

In a microwave vial, a solution of compound int-2g (1188 mg, 3.35 mmol) in 3.35 mL of MeOH was added and treated with 2-(2,2-dimethoxyethoxy)ethanamine (500 mg, 3.35 mmol). The vial was then sealed and stirred at 60° C. for 3 days. The solvent was removed under vacuum and the crude residue was purified by ISCO (120 g SiO$_2$) eluting with EtOAc/EtOH (3/1) to give compound int-30a. LCMS anal. calcd. for C$_{21}$H$_{37}$N$_3$O$_7$Si: 471.62; Found: 473.28 (M+1)$^+$.

Step B—Synthesis of Compound Int-30b

To a solution of compound int-30a (0.047 g, 0.1 mmol) in 1 mL of DCE was added methanesulfonic acid (0.039 mL, 0.600 mmol). The reaction was stirred at rt for 15 min before it was heated to 90° C. for 1 h. After it was cooled to room temperature, the mixture was concentrated in vacuo and the residue was dissolved in MeOH and filtered. The crude solution was purified with Gilson (10%~90%) ACN+0.05% TFA/water+0.05% TFA to give compound int-30b, which was used in the next reaction without further purification. LCMS anal. calcd. for C$_{13}$H$_{15}$N$_3$O$_5$: 293.27; Found: 294.20 (M+1)$^+$.

Step C—Synthesis of Compound Int-30c

To a solution of compound int-30b (363 mg, 1.238 mmol) and 1-iodopyrrolidine-2,5-dione (557 mg, 2.476 mmol) in MeOH (6190 µL), was added 3-chlorobenzoperoxoic acid (361 mg, 1.609 mmol). The reaction mixture was heated at 60° C. for 15 min. After it was cooled to ambient temperature, the mixture was purified with Gilson (10~90% ACN+0.05% TFA/water+0.05% TFA) to give compound int-30c. LCMS anal. calcd. for C$_{13}$H$_{14}$IN$_3$O$_5$: 419.17; Found: 420.06 (M+1)$^+$.

Step D—Synthesis of Compound Int-30d

A solution of compound int-30c (214 mg, 0.511 mmol), (2,4-difluorophenyl)methanamine (121 µL, 1.021 mmol) and N-ethyl-N-isopropylpropan-2-amine (356 µL, 2.042 mmol) in 5 mL of DMSO was bubbled with a stream of N2 for 5 min. Tetrakis(triphenylphosphine)palladium (118 mg, 0.102 mmol) was then added. A CO balloon was attached and CO gas was bubbled through a long needle to the mixture for 10 min. The mixture was heated at 90° C. under a CO balloon for 20 min. The solution was filtered and the mixture was purified with Gilson (10~90% ACN+0.05% TFA/water+0.05% TFA) to give compound int-30d as a mixture of four stereoisomers. LCMS anal. calcd. for C$_{21}$H$_{20}$F$_2$N$_4$O$_6$: 462.41; Found: 463.17 (M+1)$^+$. This material was further resolved by chiral preparative SFC (Chiral-Pak AS-H, 21×250 mm column; 50 g/min; 120 bar; 30% MeOH+0.2% DIPA) to afford isomers A (the 1$^{st}$ eluting component), isomer B (the 2$^{nd}$ eluting component), isomer C (the 3$^{rd}$ eluting component) and isomer D (the 4$^{th}$ eluting component) of compound int-30d.

Step E—Synthesis of Compound 119-122

Isomer A of compound int-30d (7.8 mg, 0.017 mmol), magnesium bromide (31 mg, 0.169 mmol), and acetonitrile (1 mL) were combined and stirred at 40° C. for 1 hr. The reaction mixture was diluted with 1 mL of MeOH and filtered (0.45 μm syringe filter) before being purified by preparative HPLC eluting with 10-90% ACN+0.05% TFA/water+0.05% TFA. Product containing fractions were combined and concentrated under reduced pressure until most of ACN had been removed. The remaining aqueous solution was extracted with DCM (3x~5 mL). The combined organic layer were sequentially dried over $Na_2SO_4$, filtered, and evaporated under reduced pressure. The resulting residue was dissolved in ACN (~5 mL), diluted with water (~5 mL), frozen, and lyophilized to afford compound 119. $^1$H NMR (500 MHz, Methanol-d4) δ 7.55-7.42 (m, 1H), 7.06-6.89 (m, 2H), 6.06 (d, J=6.6 Hz, 1H), 4.65 (s, 2H), 4.55 (dd, J=9.6, 3.9 Hz, 1H), 4.26 (ddd, J=15.9, 12.6, 3.1 Hz, 2H), 4.12 (dd, J=11.8, 4.2 Hz, 1H), 3.75 (d, J=10.5 Hz, 1H), 3.68 (td, J=12.1, 2.9 Hz, 1H), 3.53 (dd, J=11.2, 9.8 Hz, 1H), 3.33 (m, 2H), 3.13 (td, J=13.2, 12.7, 4.2 Hz, 1H). LCMS anal. calcd. for $C_{20}H_{18}F_2N_4O_6$: 448.38; Found: 449.21 $(M+1)^+$.

Following essentially the method employed to produce compound 119 in Step D of example 30, compound 120 was prepared from isomer B of compound int-30c. $^1$H NMR (500 MHz, Chloroform-d) δ 7.38 (q, J=8.3 Hz, 1H), 6.85 (q, J=9.5, 8.9 Hz, 2H), 5.77 (t, J=8.5 Hz, 1H), 4.67 (qd, J=15.3, 5.5 Hz, 2H), 4.53 (dd, J=9.5, 3.7 Hz, 1H), 4.42-4.32 (m, 2H), 4.17 (dq, J=10.7, 6.1, 5.1 Hz, 2H), 4.04 (t, J=8.3 Hz, 1H), 3.67 (td, J=12.1, 2.6 Hz, 1H), 3.57-3.47 (m, 1H), 3.23-3.06 (m, 2H). LCMS anal. calcd. for $C_{20}H_{18}F_2N_4O_6$: 448.38; Found: 449.18 $(M+1)^+$.

Following essentially the method employed to produce compound 119 in Step D of example 30, compound 121 was prepared from isomer C of compound int-30c. $^1$H NMR (500 MHz, Methanol-d4) δ 7.47 (dd, J=14.8, 8.5 Hz, 1H), 7.04-6.90 (m, 2H), 5.75 (m, 1H), 4.67 (m, 2H), 4.33-4.22 (m, 2H), 4.21-4.08 (m, 2H), 3.65 (m, 1H), 3.50 (dd, J=20.9, 11.1 Hz, 2H), 3.22-3.09 (m, 2H). LCMS anal. calcd. for $C_{20}H_{18}F_2N_4O_6$: 448.38; Found: 449.18 $(M+1)^+$.

Following essentially the method employed to produce compound 119 in Step D of example 30, compound 122 was prepared from isomer D of compound int-30c. $^1$H NMR (500 MHz, Methanol-d4) δ 7.53-7.42 (m, 1H), 6.97 (dtd, J=13.1, 8.6, 8.1, 2.5 Hz, 2H), 6.04 (d, J=6.6 Hz, 1H), 4.65 (s, 2H), 4.56 (dd, J=9.6, 4.0 Hz, 1H), 4.25 (ddd, J=15.5, 12.7, 3.2 Hz, 2H), 4.12 (dd, J=11.9, 4.1 Hz, 1H), 3.74 (d, J=10.5 Hz, 1H), 3.68 (td, J=12.1, 2.9 Hz, 1H), 3.52 (dd, J=11.2, 9.8 Hz, 1H), 3.33 (dt, J=3.3, 1.6 Hz, 2H), 3.13 (td, J=13.8, 4.3 Hz, 1H). LCMS anal. calcd. for $C_{20}H_{18}F_2N_4O_6$: 448.38; Found: 449.21 $(M+1)^+$.

Assessing Antiviral Potency in a Multiple Round HIV-1 Infection Assay

The antiviral activity of the Examples herein was assessed in an assay that measures the rate of replication of HIV in cell culture, and performed according to the following procedure. HIV-1 replication was monitored using MT4-gag-GFP clone D3 (hereafter designated MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection. MT4-GFP cells were maintained at 37° C./5% $CO_{2/90}$% relative humidity in RPMI 1640 supplemented with 10% fetal bovine serum, 100 U/ml penicillin/streptomycin, and 400 μg/ml G418 to maintain the reporter gene. For infections, MT4-GFP cells were placed in the same medium lacking G418 and infected overnight with HIV-1 (H9/IIIB strain) virus at an approximate multiplicity of infection of 0.01 in the same incubation conditions. Cells were then washed and re-suspended in either RPMI 1640 at $2\times10^5$ cells/mL (0% NHS condition) or 100% normal human serum (NHS) at $2\times10^5$ cells/mL (100% NHS condition). Compound plates were prepared by dispensing compounds dissolved in DMSO into wells of 384 well poly-D-lysine-coated plates (0.2 μl/well) using an ECHO acoustic dispenser. Each compound was tested in a 10-point serial 3-fold dilution (typical final concentrations: 1050 nM-0.05 nM for 0% NHS condition or 42 pM-2.13 nM for 100% NHS condition). Controls included no inhibitor (DMSO only) and a combination of three antiviral agents (efavirenz, indinavir, an in-house integrase strand transfer inhibitor at final concentrations of 4 pM each). Cells were added (50p/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, R0, which is typically 5-15 and has been shown experimentally to be in logarithmic phase (data not shown). Inhibition of R0 is calculated for each well, and $IC_{50}$s determined by non-linear 4-parameter curve fitting. Assay $IC_{50}$ results are shown in the table below.

| Compound No. | WILD TYPE CELL ASSAY Viking IP (0% NHS) (nM) |
|---|---|
| 1 | 1.7 |
| 2 | 1.6 |
| 3 | 3.2 |
| 4 | 3.5 |
| 5 | 3.5 |
| 6 | 3.0 |
| 7 | 1.6 |
| 8 | 1.9 |
| 9 | 1.4 |
| 10 | 1.9 |
| 11 | 2.8 |
| 12 | 1.7 |
| 13 | 1.7 |
| 14 | 1.4 |
| 15 | 2.6 |
| 16 | 1.9 |
| 17 | 1.5 |
| 18 | 1.6 |
| 19 | 2.7 |
| 20 | 1.7 |
| 21 | 1.4 |
| 22 | 2.3 |
| 23 | 2.3 |
| 24 | 1.5 |
| 25 | 2.0 |
| 26 | 3.4 |
| 27 | 2.9 |
| 28 | 3.3 |
| 29 | 0.76 |
| 30 | 1.6 |
| 31 | 4.9 |
| 32 | 2.5 |
| 33 | 1.4 |
| 34 | 2.8 |
| 35 | 2.1 |
| 36 | 1.5 |
| 37 | 2.5 |
| 38 | 3.5 |
| 39 | 2.2 |
| 40 | 2.1 |
| 41 | 2.8 |
| 42 | 1.9 |

-continued

| Compound No. | WILD TYPE CELL ASSAY Viking IP (0% NHS) (nM) |
|---|---|
| 43 | 3.4 |
| 44 | 3.1 |
| 45 | 2.5 |
| 46 | 3.7 |
| 47 | 2.8 |
| 48 | 2.3 |
| 49 | 2.0 |
| 50 | 4.2 |
| 51 | 2.1 |
| 52 | 8.1 |
| 53 | 1.1 |
| 54 | 4.7 |
| 55 | 1.6 |
| 56 | 2.9 |
| 57 | 2.4 |
| 58 | 4.0 |
| 59 | 2.5 |
| 60 | 2.8 |
| 61 | 1.9 |
| 62 | 5.2 |
| 63 | 1.6 |
| 64 | 5.9 |
| 65 | 2.0 |
| 66 | 2.0 |
| 67 | 1.6 |
| 68 | 1.7 |
| 69 | 1.9 |
| 70 | 1.8 |
| 71 | 3.7 |
| 72 | 2.3 |
| 73 | 80 |
| 74 | 66 |
| 75 | 35 |
| 76 | 88 |
| 77 | 258 |
| 78 | 87 |
| 79 | 103 |
| 80 | 219 |
| 81 | 2.8 |
| 82 | 2.2 |
| 83 | 2.5 |
| 84 | 2.1 |
| 85 | 2.6 |
| 86 | 1.3 |
| 87 | 4.2 |
| 88 | 2.9 |
| 89 | 1.9 |
| 90 | 1.9 |
| 91 | 3.3 |
| 92 | 1.7 |
| 93 | 9.3 |
| 94 | 14 |
| 95 | 7.5 |
| 96 | 26 |
| 97 | ND |
| 98 | ND |
| 99 | ND |
| 100 | ND |
| 101 | 2.5 |
| 102 | 3.5 |
| 103 | ND |
| 104 | 3.9 |
| 105 | ND |
| 106 | ND |
| 107 | 2.3 |
| 108 | 2.8 |
| 109 | 2.6 |
| 110 | 1.7 |
| 111 | 2.1 |
| 112 | 1.7 |
| 113 | 1.5 |
| 114 | 1.9 |
| 115 | 2.0 |
| 116 | 3.1 |
| 117 | 1.8 |
| 118 | 1.6 |
| 119 | 2.9 |
| 120 | ND |
| 121 | 2.0 |
| 122 | 2.2 |

ND: Not determined.

Treatment or Prevention of HIV Infection

The Tricyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Tricyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Tricyclic Heterocycle Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Tricyclic Heterocycle Compounds are also useful in the preparation and execution of screening assays for antiviral compounds. For example the Tricyclic Heterocycle Compounds may be useful for identifying resistant HIV cell lines harboring mutations, which are excellent screening tools for more powerful antiviral compounds. Furthermore, the Tricyclic Heterocycle Compounds may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Tricyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Tricyclic Heterocycle Compound (which may include two or more different Tricyclic Heterocycle Compounds), or a pharmaceutically acceptable salt or prodrug thereof, and (ii) at least one additional therapeutic agent that is other than a Tricyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Tricyclic Heterocycle Compound is administered during a time when the additional therapeutic agent(s) exert their prophylactic or therapeutic effect, or vice versa.

In another embodiment, at least one Tricyclic Heterocycle Compound and the additional therapeutic agent(s) are administered in doses commonly employed when such agents are used as monotherapy for treating a viral infection.

In another embodiment, at least one Tricyclic Heterocycle Compound and the additional therapeutic agent(s) are administered in doses lower than the doses commonly employed when such agents are used as monotherapy for treating a viral infection.

In still another embodiment, at least one Tricyclic Heterocycle Compound and the additional therapeutic agent(s) act synergistically and are administered in doses lower than the doses commonly employed when such agents are used as monotherapy for treating a viral infection.

In one embodiment, at least one Tricyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Tricyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tricyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
| --- | --- |
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | |
| efavirenz, EFV | Sustiva ®, Stocrin ® |
| efavirenz + emtricitabine + tenofovir DF | Atripla ® |
| EFdA (4'-ethynyl-2-fluoro-2'-deoxyadenosine) | |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine, doravirine, EFdA and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with EFdA.

In another embodiment, the compound of formula (I) is used in combination with emtricitabine and tenofovir.

In still another embodiment, the compound of formula (I) is used in combination doravirine.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof, (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Tricyclic Heterocycle Compounds may be administered as a component of a composition that comprises a pharmaceutically acceptable carrier or vehicle. The present invention provides pharmaceutical compositions comprising an effective amount of at least one Tricyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tricyclic Heterocycle Compounds are administered orally.

In another embodiment, the one or more Tricyclic Heterocycle Compounds are administered intravenously.

In one embodiment, a pharmaceutical preparation comprising at least one Tricyclic Heterocycle Compound is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Tricyclic Heterocycle Compound(s) by weight or volume. In various embodiments, the present compositions can contain, in one embodiment, from about 1% to about 70% or from about 5% to about 60% of the Tricyclic Heterocycle Compound(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Tricyclic Heterocycle Compounds may be administered at varying frequencies. In one embodiment, a unit dosage of a Tricyclic Heterocycle Compound may be administered once daily. In another embodiment, a unit dosage of a Tricyclic Heterocycle Compound may be administered twice weekly. In another embodiment, a unit dosage of a Tricyclic Heterocycle Compound may be administered once weekly. In still another embodiment, a unit dosage of a Tricyclic Heterocycle Compound may be administered once biweekly. In another embodiment, a unit dosage of a Tricyclic Heterocycle Compound may be administered once monthly. In yet another embodiment, a unit dosage of a Tricyclic Heterocycle Compound may be administered once bimonthly. In another embodiment, a unit dosage of a Tricyclic Heterocycle Compound may be administered once every 3 months. In a further embodiment, a unit dosage of a Tricyclic Heterocycle Compound may be administered once every 6 months. In another embodiment, a unit dosage of a Tricyclic Heterocycle Compound may be administered once yearly.

The amount and frequency of administration of the Tricyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Tricyclic Heterocycle Compound, or a pharmaceutically acceptable salt or prodrug of said compound and a pharmaceutically acceptable carrier, vehicle or diluent.

In another aspect the present invention provides a kit comprising an amount of at least one Tricyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Tricyclic Heterocycle Compounds and the one or more additional therapeutic agents are provided in the same container. In one embodiment, the one or more Tricyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound of the formula:

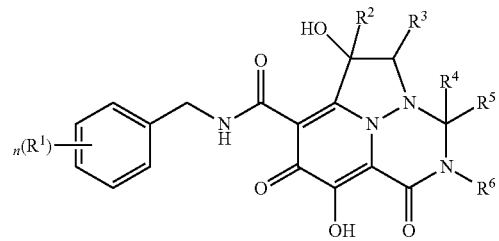

or a pharmaceutically acceptable salt thereof,
wherein:
each occurrence of $R^1$ is independently halo or $C_{1-3}$ alkyl, wherein said alkyl groups are optionally substituted with one to three halo;
$R^2$ is hydrogen, methyl or ethyl;
$R^3$ is hydrogen, methyl or ethyl;
$R^4$ is hydrogen, methyl or ethyl;
$R^5$ is hydrogen, $C_{1-3}$ alkyl, $(C_{1-3}$ alkyl$)OR^7$ or phenyl;

or R⁴ and R⁵ can be taken together with the carbon atom to which they are attached to form a 5- or 6-membered heterocyclyl group;

R⁶ is hydrogen, C$_{1-6}$ alkyl or (C$_{1-6}$ alkyl)OR⁷;

or R⁵ and R⁶ can be taken together with the atoms between them to form a 6-membered heterocyclyl group;

R⁷ is hydrogen or C$_{1-3}$ alkyl, which is optionally substituted with one to three halo;

n is an integer between one and three.

2. The compound of claim 1 wherein each R¹ is halo, or a pharmaceutically acceptable salt thereof.

3. The compound of claim 1 wherein R² is hydrogen, or a pharmaceutically acceptable salt thereof.

4. The compound of claim 1 wherein R³ is hydrogen, or a pharmaceutically acceptable salt thereof.

5. The compound of claim 1 wherein R⁴ is hydrogen or methyl, or a pharmaceutically acceptable salt thereof.

6. The compound of claim 1 wherein R⁴ is hydrogen, or a pharmaceutically acceptable salt thereof.

7. The compound of claim 1 wherein R⁵ is hydrogen, methyl, ethyl, CH₂OCH₃ or phenyl, or a pharmaceutically acceptable salt thereof.

8. The compound of claim 1 wherein R⁶ is methyl, ethyl or CH₂CH₂OCH₃, or a pharmaceutically acceptable salt thereof.

9. The compound of claim 1 wherein R⁴ and R⁵ can be taken together with the carbon atom to which they are attached to form a 5-membered heterocyclyl group, or a pharmaceutically acceptable salt thereof.

10. The compound of claim 1 wherein R⁴ and R⁵ can be taken together with the carbon atom to which they are attached to form a tetrahydrofuranyl group, or a pharmaceutically acceptable salt thereof.

11. The compound of claim 1 wherein R⁵ and R⁶ can be taken together with the atoms between them to form a morpholinyl group, or a pharmaceutically acceptable salt thereof.

12. The compound of claim 1 selected from:

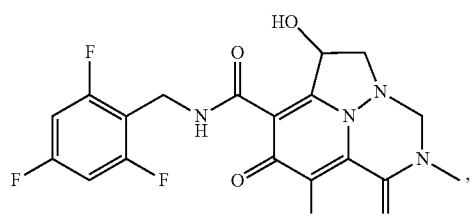

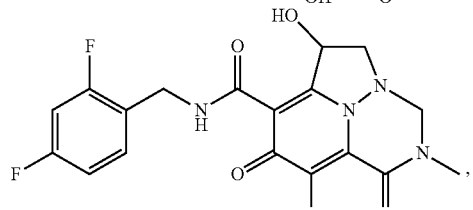

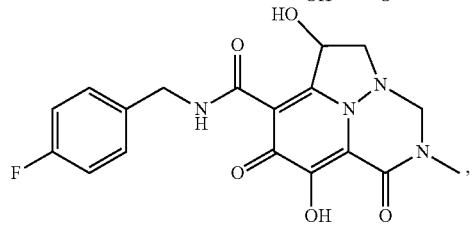

-continued

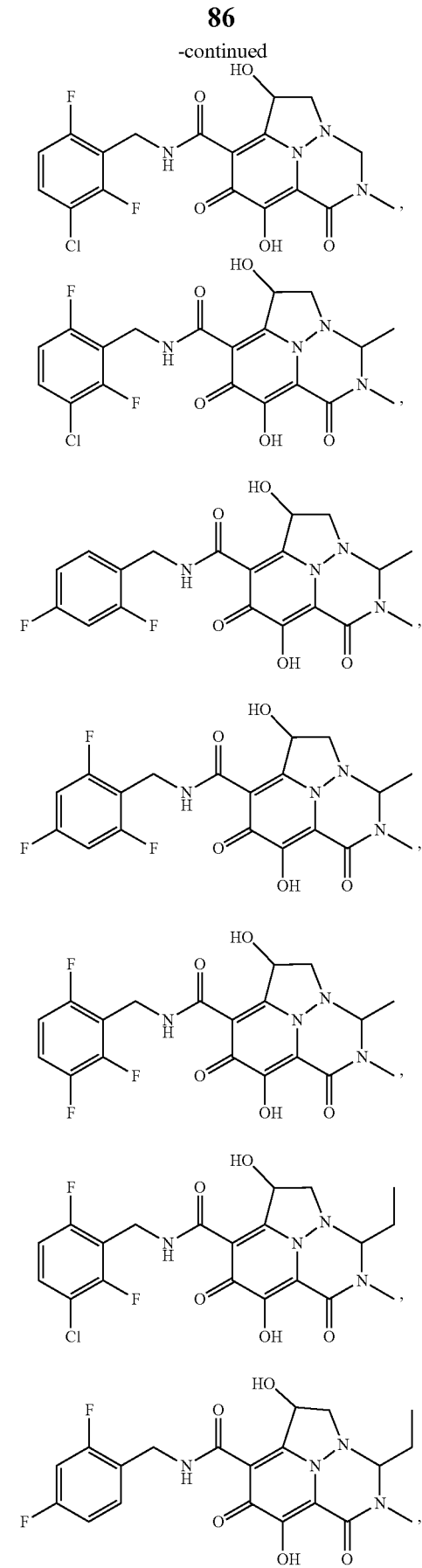

87
-continued
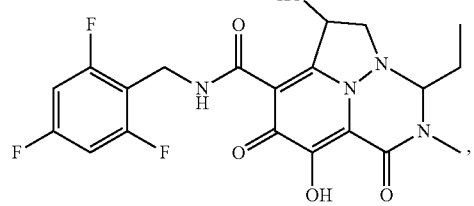
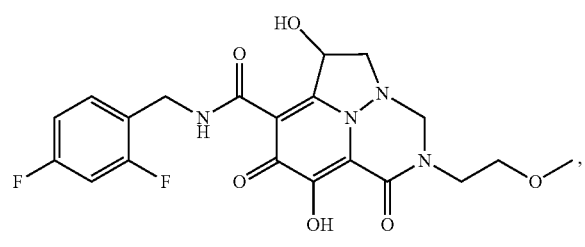
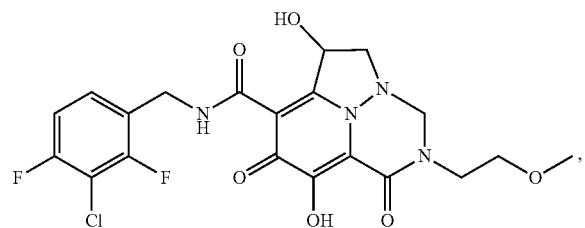
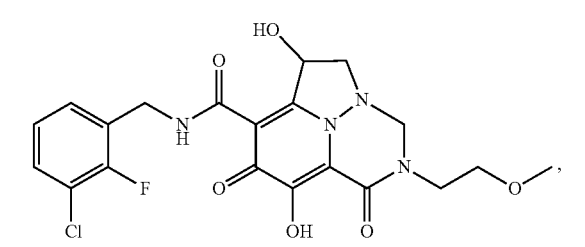
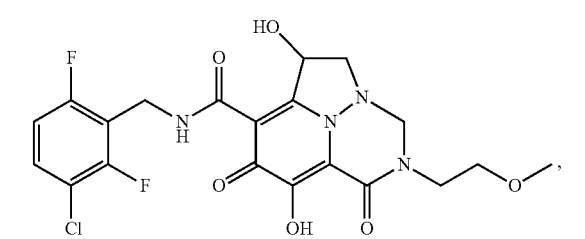
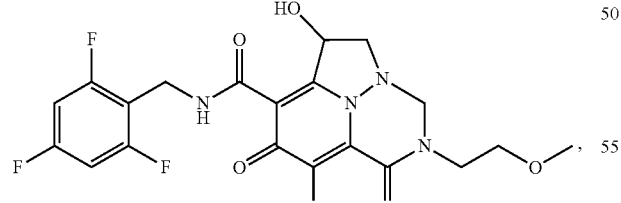
88
-continued
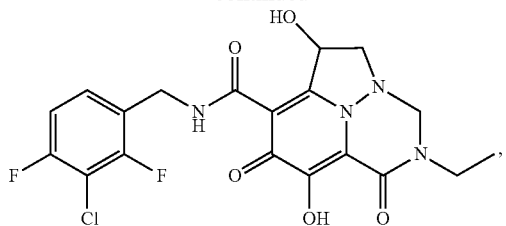
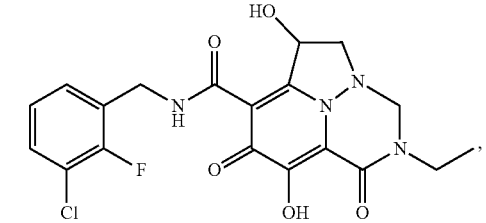
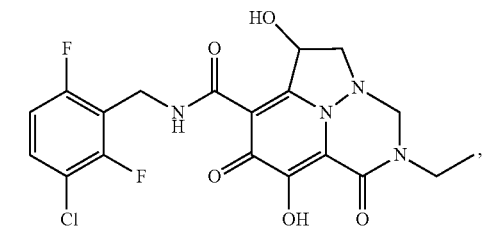
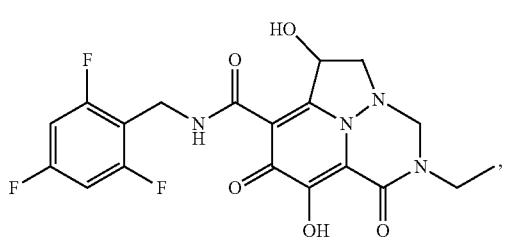
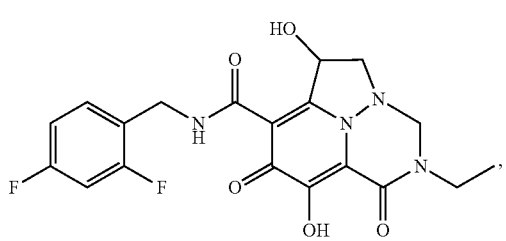
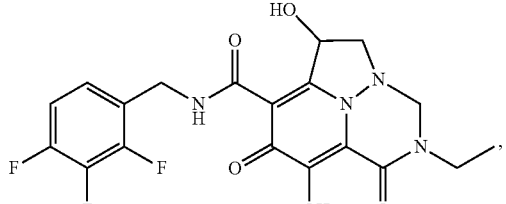
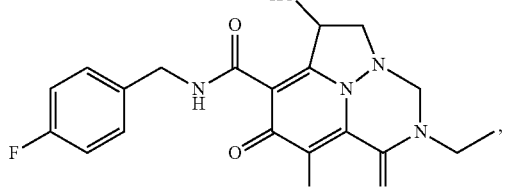

-continued

-continued

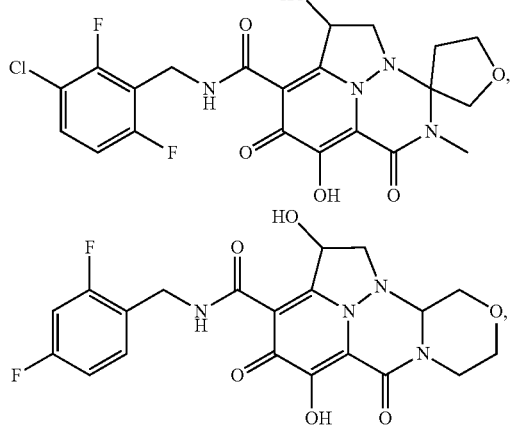

or a pharmaceutically acceptable salt thereof.

13. A pharmaceutical composition comprising an effective amount of a compound according to claim 1, or a pharmaceutically acceptable salt thereof, and a pharmaceutically acceptable carrier.

14. A method for the inhibition of HIV integrase in a subject in need thereof which comprises administering to the subject an effective amount of the compound according to claim 1, or a pharmaceutically acceptable salt thereof.

15. A method for the treatment of infection by HIV or for the treatment of AIDS in a subject in need thereof, which comprises administering to the subject an effective amount of the compound according to claim 1, or a pharmaceutically acceptable salt thereof.

16. The pharmaceutical composition of claim 13, further comprising one or more additional therapeutic agents selected from, raltegravir, lamivudine, abacavir, ritonavir, dolutegravir, arunavir, atazanavir, emtricitabine, tenofovir, elvitegravir, rilpivirine, EFdA, doravirine and lopinavir.

17. A method for the treatment of infection by HIV or for the treatment of AIDS in a subject in need thereof, which comprises administering to the subject an effective amount of the compound according to claim 1, or a pharmaceutically acceptable salt thereof, further comprising administering to the subject one or more additional therapeutic agents selected from raltegravir, lamivudine, abacavir, ritonavir, dolutegravir, arunavir, atazanavir, emtricitabine, tenofovir, elvitegravir, rilpivirin, EFdA, doravirine and lopinavir, wherein the amounts administered of the compound of claim 1 and the one or more additional therapeutic agents, are together effective to treat infection by HIV or to treat, prevent or delay the onset or progression of AIDS.

* * * * *